United States Patent
Gearing

(10) Patent No.: US 11,566,049 B2
(45) Date of Patent: Jan. 31, 2023

(54) CYCLIC PEPTIDES AND USES THEREOF

(71) Applicant: LATERAL IP PTY LTD, Melbourne (AU)

(72) Inventor: Andrew Gearing, Melbourne (AU)

(73) Assignee: LATERAL IP PTY LTD, Melbourne (AU)

( * ) Notice: Subject to any disclaimer, the term of this patent is extended or adjusted under 35 U.S.C. 154(b) by 0 days.

(21) Appl. No.: 17/041,916

(22) PCT Filed: Mar. 29, 2019

(86) PCT No.: PCT/AU2019/050285
§ 371 (c)(1),
(2) Date: Sep. 25, 2020

(87) PCT Pub. No.: WO2019/183686
PCT Pub. Date: Oct. 3, 2019

(65) Prior Publication Data
US 2021/0130410 A1    May 6, 2021

(30) Foreign Application Priority Data
Mar. 29, 2018    (AU) .................. 2018901063

(51) Int. Cl.
*C07K 7/64*    (2006.01)
*A61P 25/04*    (2006.01)
*A61K 38/00*    (2006.01)

(52) U.S. Cl.
CPC .............. *C07K 7/64* (2013.01); *A61P 25/04* (2018.01); *A61K 38/00* (2013.01)

(58) Field of Classification Search
None
See application file for complete search history.

(56) References Cited

U.S. PATENT DOCUMENTS 6,262,228 B1 * 7/2001 Cao .................. C07K 14/7056
                                                      435/7.1

FOREIGN PATENT DOCUMENTS

| JP | 2010-209035 A | 9/2010 |
| WO | WO-97/32895 | 9/1997 |
| WO | WO-00/15654 A1 | 3/2000 |
| WO | WO-2015/040089 A1 | 3/2015 |

OTHER PUBLICATIONS

Qvit et al. (Crit Rev Eukaryot Gene Expr. 2016; 26(3): 199-221) (Year: 2016).*
NCBI Accession No. WP_003698179 (hypothetical protein [Neisseria gonorrhoeae]) dated May 26, 2013.
Colangelo et al., "A New Nerve Growth Factor-Mimetic Peptide Active on Neuropathic Pain in Rats," The Journal of Neuroscience, vol. 28, No. 11, pp. 2698-2709 (Mar. 2008).

* cited by examiner

*Primary Examiner* — Sergio Coffa
(74) *Attorney, Agent, or Firm* — Foley & Lardner LLP

(57) ABSTRACT

The present disclosure is directed to a peptide of formula (I), or a pharmaceutically acceptable salt thereof, and uses thereof: $R^1-C-R-X^1-X^2-P-X^3-X^4-X^5-X^6-C-R^2$ (I) wherein $X^1$, $X^3$, $X^5$, and $X^6$ is an amino acid residue selected from the group consisting of serine, alanine, valine, leucine, isoleucine and glycine; $X^2$ is alanine, arginine or lysine; $X^4$ is glutamic acid or aspartic acid; $R^1$ is selected from the group consisting of S, HS, GHS, PGHS, APGHS, EAPGHS, SEAPGHS, SSEAPGHS, PSSEAPGHS, DPSSEAPGHS and IDPSSEAPGHS, or $R^1$ is absent; and $R^2$ is selected from the group consisting of S, SS, SSK, SSKF, SSKFS, SSKFSW, SSKFSWD, SSKFSWDE, SSKFSWDEY, SSKFSWDEYE, SSKFSWDEYEQ, SSKFSWDEYEQY, SSKFSWDEYEQYK, SSKFSWDEYEQYKK, SSKFSWDEYEQYKKE, or $R^2$ is absent; and wherein the peptide of formula (I), or the pharmaceutically acceptable salt thereof, is a cyclic peptide formed by a disulphide bond between the two cysteine residues.

8 Claims, 37 Drawing Sheets
Specification includes a Sequence Listing.

CYCLIC PEPTIDES AND USES THEREOF

CROSS-REFERENCE TO RELATED APPLICATIONS

The present application is the U.S. National Stage of International Application No. PCT/AU2019/050285, filed Mar. 29, 2019, and claims priority to Australian Patent Application No. 2018901063, filed Mar. 29, 2018.

SEQUENCE LISTING

The instant application contains a Sequence Listing which has been submitted electronically in ASCII format and is hereby incorporated by reference in its entirety. Said ASCII copy, created on Nov. 24, 2020, is named 35524645 ST25.txt and is 6,401 bytes in size.

FIELD OF THE INVENTION

The present invention relates generally to cyclic peptides and uses thereof in the treatment of various conditions, illustrative examples of which include pain, wasting disorders, obesity, osteoarthritis and metabolic disorders.

BACKGROUND

All references, including any patents or patent application, cited in this specification are hereby incorporated by reference to enable full understanding of the invention. Nevertheless, such references are not to be read as constituting an admission that any of these documents forms part of the common general knowledge in the art, in Australia or in any other country.

Neuropathic pain is caused by a primary lesion, malfunction or dysfunction in the peripheral or central nervous system. Unlike nociceptive pain, which serves a protective biological function by warning of ongoing tissue damage, neuropathic pain has no protective effect and can develop days or months after an injury or after resolution of a disease state, and is frequently long-lasting and chronic.

Neuropathic pain may result from nerve damage caused by a trauma such as a sporting injury, an accident, a fall or a penetrating injury or the nerve damage may result from a disease process such as stroke, viral infections, exposure to toxins, including chemotherapeutic agents, degenerative diseases and diabetes. The prevalence of disease states which may result in the development of neuropathic pain conditions such as diabetic neuropathy and post-herpetic neuralgia is increasing and therefore an increasing number of people are suffering chronic neuropathic pain symptoms.

Although there are effective remedies for treating nociceptive pain, neuropathic pain is often resistant to available analgesic drugs. In addition, current therapies such as tricyclic antidepressants, anticonvulsants, opioid and non-opioid analgesics have significant side effects such as sedation and sleepiness and in the case of opioid analgesics, the risk of drug tolerance and drug dependency or addiction. Thus, there is an urgent need for new and improved treatment options that are effective for alleviating neuropathic pain, including symptoms thereof, with limited or no side effects.

SUMMARY OF THE DISCLOSURE

In an aspect disclosed herein, there is provided a peptide of formula (I), or a pharmaceutically acceptable salt thereof:

$$R^1\text{-}C\text{-}R\text{-}X^1\text{-}X^2\text{-}P\text{-}X^3\text{-}X^4\text{-}X^5\text{-}X^6\text{-}C\text{-}R^2 \quad \text{(SEQ ID NO: 1)}$$

(I)

wherein
$X^1$, $X^3$, $X^5$, and $X^6$ is an amino acid residue selected from the group consisting of serine, alanine, valine, leucine, isoleucine and glycine;
$X^2$ is alanine, arginine or lysine;
$X^4$ is glutamic acid or aspartic acid;
$R^1$ is selected from the group consisting of:

S,

HS, (SEQ ID NO: 2)

GHS, (SEQ ID NO: 3)

PGHS, (SEQ ID NO: 4)

APGHS, (SEQ ID NO: 5)

EAPGHS, (SEQ ID NO: 6)

SEAPGHS, (SEQ ID NO: 7)

SSEAPGHS, (SEQ ID NO: 8)

PSSEAPGHS, (SEQ ID NO: 9)

DPSSEAPGHS, (SEQ ID NO: 10)
and

IDPSSEAPGHS, (SEQ ID NO: 11)

or $R^1$ is absent; and
$R^2$ is selected from the group consisting of:

S,

SS, (SEQ ID NO: 12)

SSK, (SEQ ID NO: 13)

SSKF, (SEQ ID NO: 14)

SSKFS, (SEQ ID NO: 15)

SSKFSW, (SEQ ID NO: 16)

SSKFSWD, (SEQ ID NO: 17)

SSKFSWDE, (SEQ ID NO: 18)

-continued

SSKFSWDEY, (SEQ ID NO: 19)

SSKFSWDEYE, (SEQ ID NO: 20)

SSKFSWDEYEQ, (SEQ ID NO: 21)

SSKFSWDEYEQY, (SEQ ID NO: 22)

SSKFSWDEYEQYK, (SEQ ID NO: 23)

SSKFSWDEYEQYKK, (SEQ ID NO: 24)
and

SSKFSWDEYEQYKKE, (SEQ ID NO: 25)

or $R^2$ is absent; and
wherein the peptide of formula (I), or the pharmaceutically acceptable salt thereof, is a cyclic peptide formed by a disulphide bond between the two cysteine residues.

In another aspect disclosed herein, there is provided a pharmaceutical composition comprising a peptide of formula (I), or a pharmaceutically acceptable salt thereof, and at least one pharmaceutically acceptable carrier.

In another aspect disclosed herein, there is provided a method of treating a condition in a subject, the method comprising administering to a subject a therapeutically effective amount of a peptide of formula (I), or a pharmaceutically acceptable salt thereof, as herein described, wherein the condition is selected from the group consisting of sarcopenia, impaired glucose tolerance, diabetes, obesity, metabolic disease and obesity-related conditions, osteoarthritis, a disorder of muscle, a wasting disorder, cachexia, anorexia, AIDS wasting syndrome, muscular dystrophy, neuromuscular disease, motor neuron disease, diseases of the neuromuscular junction, inflammatory myopathy, a burn, injury or trauma, a condition associated with elevated LDL cholesterol, a condition associated with impaired chondrocyte, proteoglycan or collagen production or quality, a condition associated with impaired cartilage tissue formation or quality, a condition that requires skin or wound repair, a condition associated with impaired muscle, ligament or tendon mass, form or function, a condition associated with inflammation, trauma or a genetic abnormality affecting muscle or connective tissue, a bone disorder, migraine and pain (e.g., neuropathic pain), in an embodiment disclosed herein, the condition is neuropathic pain.

In a further aspect disclosed herein, there is provided a use of a peptide of formula (I), or a pharmaceutically acceptable salt thereof, as herein described, in the manufacture of a medicament for treating a condition selected from the group consisting of sarcopenia, impaired glucose tolerance, diabetes, obesity, metabolic disease and obesity-related conditions, osteoarthritis, a disorder of muscle, a wasting disorder, cachexia, anorexia, AIDS wasting syndrome, muscular dystrophy, neuromuscular disease, motor neuron disease, diseases of the neuromuscular junction, inflammatory myopathy, a burn, injury or trauma, a condition associated with elevated LDL cholesterol, a condition associated with impaired chondrocyte, proteoglycan or collagen production or quality, a condition associated with impaired cartilage tissue formation or quality, a condition that requires skin or wound repair, a condition associated with impaired muscle, ligament or tendon mass, form or function, a condition associated with inflammation, trauma or a genetic abnormality affecting muscle or connective tissue, a bone disorder, migraine and pain (e.g., neuropathic pain). In an embodiment disclosed herein, the condition is neuropathic pain.

In another aspect disclosed herein, there is provided a peptide of formula (I), or a pharmaceutically acceptable salt thereof, as herein described, for use in treating a condition selected from the group consisting of sarcopenia, impaired glucose tolerance, diabetes, obesity, metabolic disease and obesity-related conditions, osteoarthritis, a disorder of muscle, a wasting disorder, cachexia, anorexia, AIDS wasting syndrome, muscular dystrophy, neuromuscular disease, motor neuron disease, diseases of the neuromuscular junction, inflammatory myopathy, a burn, injury or trauma, a condition associated with elevated LDL cholesterol, a condition associated with impaired chondrocyte, proteoglycan or collagen production or quality, a condition associated with impaired cartilage tissue formation or quality, a condition that requires skin or wound repair, a condition associated with impaired muscle, ligament or tendon mass, form or function, a condition associated with inflammation, trauma or a genetic abnormality affecting muscle or connective tissue, a bone disorder, migraine and pain (e.g., neuropathic pain). In an embodiment disclosed herein, the condition is neuropathic pain.

Figure 1:
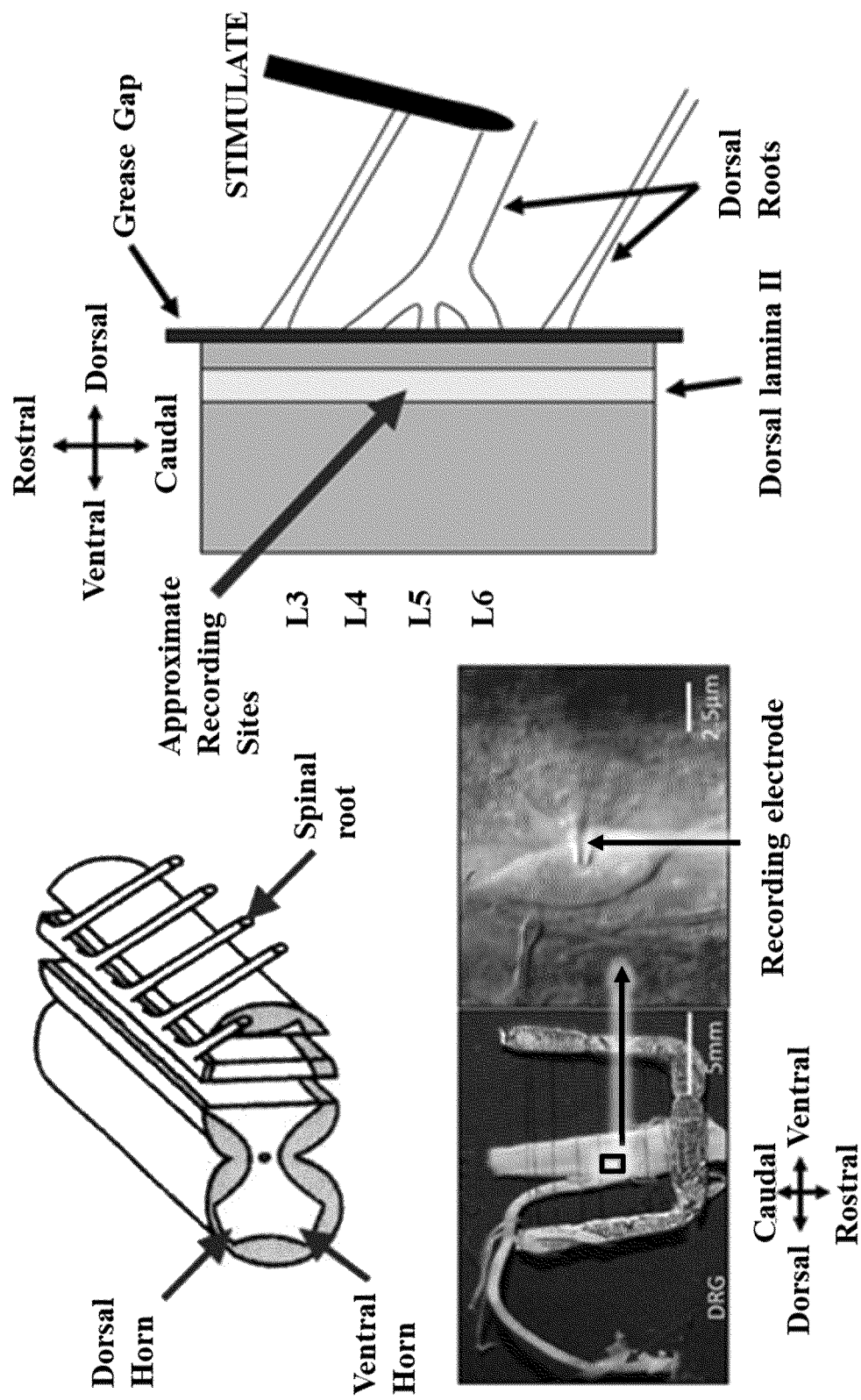
FIG. 1 is a schematic diagram showing the preparation of spinal cord slices and whole cell recording sites in models of neuropathic pain.

In an embodiment, $R^1$ is absent. In another embodiment, $R^2$ is absent. In yet another embodiment, $R^1$ and $R^2$ are absent.

In some embodiments, $R^1$ is capped with an N-terminal capping group. The term "N-terminal capping group" typically refers to a group that blocks the reactivity of the N-terminal amino group. Suitable N-terminal capping groups will be familiar to persons skilled in the art, illustrative examples of which include acyl groups that form amide groups with the N-terminal amino group, for example, the N-terminal capping group forms a —NHC(O)Ra, where the NH is from the N-terminal amino group and Ra is alkyl, alkenyl, alkynyl, cycloalkyl or aryl. In an embodiment, the N-terminal capping group is —C(O)CH$_3$ (acyl), forming —NHC(O)CH$_3$.

In an embodiment, $R^1$ is a serine residue (S).

In another embodiment, $R^2$ is capped with an C-terminal capping group. The term "C-terminal capping group" typically refers to a group that blocks the reactivity of the C-terminal carboxylic acid. Suitable C-terminal capping groups form amide groups or esters with the C-terminal carboxylic acid, for example, the C-terminal capping group forms a —C(O)NHR$^a$ or —C(O)OR$^b$ where the C(O) is from the C-terminal carboxylic acid group and R$^a$ is hydrogen, alkyl, alkenyl, alkynyl, cycloalkyl or aryl and is alkyl, alkenyl, alkynyl, cycloalkyl or aryl. In particular embodiments, the C-terminal capping group is —NH$_2$, forming —C(O)NH$_2$.

In an embodiment, $R^2$ is a serine residue (S).

In another embodiment, $R^1$ is a serine residue and $R^2$ is a serine residue.

In some embodiments, one or both of $R^1$ and $R^2$ further comprises polyethylene glycol (PEG). The PEG may have a molecular weight in the range of 220 to 5500 Da, preferably 220 to 2500 Da, or more preferably 570 to 1100 Da. In an embodiment, $R^1$ is S. In another embodiment, $R^1$ is HS. In an embodiment, $R^1$ is GHS. In an embodiment, $R^1$ is PGHS. In an embodiment, $R^1$ is APGHS. In an embodiment, $R^1$ is EAPGHS. In an embodiment, $R^1$ is SEAPGHS. In an embodiment, $R^1$ is SSEAPGHS. In an embodiment, $R^1$ is PSSEAPGHS. In an embodiment, $R^1$ is DPSSEAPGHS. In an embodiment, $R^1$ is IDPSSEAPGHS. In an embodiment, $R^1$ is absent. In an embodiment, $R^2$ is S. In an embodiment, $R^2$ is SS. In an embodiment, $R^2$ is SSK. In an embodiment, $R^2$ is SSKF. In an embodiment, $R^2$ is SSKFS. In an embodiment, $R^2$ is SSKFSW. In an embodiment, $R^2$ is SSKFSWD. In an embodiment, $R^2$ is SSKFSWDE. In an embodiment, $R^2$ is SSKFSWDEY. In an embodiment, $R^2$ is SSKFSWDEYE. In an embodiment, $R^2$ is SSKFSWDEYEQ. In an embodiment, $R^2$ is SSKFSWDEYEQY. In an embodiment, $R^2$ is SSKFSWDEYEQYK. In an embodiment, $R^2$ is SSKFSWDEYEQYKK. In an embodiment, $R^2$ is SSKFSWDEYEQYKKE. In an embodiment, $R^2$ is absent. In an embodiment, $X^5$ and $X^6$ is an amino acid residue selected from the group consisting of serine, valine, leucine, isoleucine and glycine.

The peptides of formula (I) can be from 10 to 50 amino acid residues in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues in length), preferably 10 to 40 in length, more preferably 10 to 30 in length, more preferably 10 to 25 in length, or more preferably 10 to 20 in length.

The peptide of the formula (I) may be made of naturally occurring amino acid residues, proteogenic or non-proteogenic. These amino acids have L-stereochemistry. Naturally occurring amino acids are set out in Table 1, below.

TABLE 1

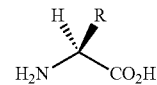

(1)

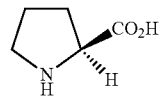

(2)

| Amino Acid | Three-letter Abbreviation | One-letter symbol | Structure of side chain (R) in (1) above |
|---|---|---|---|
| Alanine | Ala | A | —CH$_3$ |
| Arginine | Arg | R | —(CH$_2$)$_3$NHC(=N)NH$_2$ |
| Asparagine | Asn | N | —CH$_2$CONH$_2$ |
| Aspartic acid | Asp | D | —CH$_2$CO$_2$H |
| Cysteine | Cys | C | —CH$_2$SH |
| Glutamine | Gln | Q | —(CH$_2$)$_2$CONH$_2$ |
| Glutamic acid | Glu | E | —(CH$_2$)$_2$CO$_2$H |
| Glycine | Gly | G | —H |
| Histidine | His | H | —CH$_2$(4-imidazolyl) |
| Isoleucine | Ile | I | —CH(CH$_3$)CH$_2$CH$_3$ |
| Leucine | Leu | L | —CH$_2$CH(CH$_3$)$_2$ |
| Lysine | Lys | K | —(CH$_2$)$_4$NH$_2$ |
| Methionine | Met | M | —(CH$_2$)$_2$SCH$_3$ |
| Phenylalanine | Phe | F | —CH$_2$Ph |
| Ornithine | Orn | O | —(CH$_2$)$_3$NH$_2$ |
| Proline | Pro | P | see formula (2) above for structure of amino acid |
| Serine | Ser | S | —CH$_2$OH |
| Threonine | Thr | T | —CH(CH$_3$)OH |
| Tryptophan | Trp | W | —CH$_2$(3-indolyl) |
| Tyrosine | Tyr | Y | —CH$_2$(4-hydroxyphenyl) |
| Valine | Val | V | —CH(CH$_3$)$_2$ |

As used herein, the term "alkyl" refers to a straight chain or branched saturated hydrocarbon group having 1 to 10 carbon atoms. Where appropriate, the alkyl group may have a specified number of carbon atoms, for example, C$_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated and unsaturated (but not aromatic) cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclopentenyl, cyclohexyl, cyclohexenyl, cyclohexadienyl, cycloheptyl and cyclooctyl.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

In an embodiment disclosed herein, the peptide of formula (I) has an amino acid sequence selected from the group consisting of:

SCRSRPVESSC; (SEQ ID NO: 26)

CRSRPVESSC; (SEQ ID NO: 27)

CRSRPVESSCS; (SEQ ID NO: 28)
and

SCRSRPVESSCS. (SEQ ID NO: 29)

In an embodiment disclosed, the peptide of formula (I) has an amino acid sequence of SEQ ID NO:26. In an embodiment disclosed, the peptide of formula (I) has an amino acid sequence of SEQ ID NO:27. In an embodiment disclosed, the peptide of formula (I) has an amino acid sequence of SEQ ID NO:28. In an embodiment disclosed, the peptide of formula (I) has an amino acid sequence of SEQ ID NO:29. The peptides disclosed herein may be made by methods well known to persons skilled in the art, illustrative examples of which include by solution or solid phase synthesis using Fmoc or Boc protected amino acid residues and recombinant techniques as known in the art using standard microbial culture technology, genetically engineered microbes and recombinant DNA technology (Sambrook and Russell, Molecular Cloning: A Laboratory Manual ($3^{rd}$ Edition), 2001, CSHL Press).

The peptides of formula (I) may be in the form of a pharmaceutically acceptable salt. It will be appreciated that non-pharmaceutically acceptable salts also fall within the scope of the present disclosure. Such non-pharmaceutically acceptable salts may be useful as intermediates in the preparation of pharmaceutically acceptable salts or may be useful during storage or transport. Suitable pharmaceutically acceptable salts will be familiar to persons skilled in the art, illustrative examples of which include salts of pharmaceutically acceptable inorganic acids such as hydrochloric, sulphuric, phosphoric, nitric, carbonic, boric, sulfamic, and hydrobromic adds, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicylic sulphanilic, aspartic, glutamic, edetic, stearic, palmitic, oleic, lauric, pantothenic, tannic, ascorbic and valeric acids.

Base salts will also be familiar to persons skilled in the art, illustrative examples of which include those formed with pharmaceutically acceptable cations, such as sodium, potassium, lithium, calcium, magnesium, ammonium and alkylammonium. Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

In an embodiment disclosed herein, $X^1$ is alanine. In another embodiment, $X^3$ is alanine. In yet another embodiment, $X^1$ and $X^3$ are alanine residues. In another embodiment disclosed herein, the peptide of formula (I) has an amino acid sequence selected from the group consisting of:

SCRARPVESSC; (SEQ ID NO: 30; also referred to herein as LAT9993 SLoop A4)
and

SCRSRPAESSC. (SEQ ID NO: 31; also referred to herein as LAT9993 Sloop A7)

Methods of Treatment

As described elsewhere herein, the present invention is predicated, at least in part, on the inventors' surprising finding that peptides of formula (I) (SEQ ID NOT) may be used to treat a variety of conditions, including neuropathic pain.

Thus, disclosed herein is a method of treating a condition in a subject, the method comprising administering to a subject a therapeutically effective amount of a peptide of formula (I), or a pharmaceutically acceptable salt thereof, as herein described, and wherein the condition is selected from the group consisting of sarcopenia, impaired glucose tolerance, diabetes, obesity, metabolic disease and obesity-related conditions, osteoarthritis, a disorder of muscle, a wasting disorder, cachexia, anorexia, AIDS wasting syndrome, muscular dystrophy, neuromuscular disease, motor neuron disease, diseases of the neuromuscular junction, inflammatory myopathy, a burn, injury or trauma, a condition associated with elevated LDL cholesterol, a condition associated with impaired chondrocyte, proteoglycan or collagen production or quality, a condition associated with impaired cartilage tissue formation or quality, a condition that requires skin or wound repair, a condition associated with impaired muscle, ligament or tendon mass, form or function, a condition associated with inflammation, trauma or a genetic abnormality affecting muscle or connective tissue, a bone disorder, migraine and pain (e.g., neuropathic pain). In an embodiment, the condition is neuropathic pain.

By "neuropathic pain" is meant any pain syndrome initiated or caused by a primary lesion or dysfunction in the peripheral or central nervous system. Illustrative examples of neuropathic pain are described elsewhere herein.

The terms "treating", "treatment" and the like, are used interchangeably herein to mean relieving, reducing, alleviating, ameliorating or otherwise inhibiting the condition, including one or more symptoms thereof. In the context of neuropathic pain, exemplary symptoms include allodynia and hyperalgesia. The terms "treating", "treatment" and the like are also used interchangeably herein to mean preventing the condition from occurring or delaying the progression of the condition or delaying or preventing the onset of the condition in a subject that may be predisposed to, or at risk of, developing the condition, but has not yet been diagnosed as having the condition. In that context, the terms "treating", "treatment" and the like are used interchangeably with terms such as "prophylaxis", "prophylactic" and "preventative".

The terms "treating", "treatment" and the like also include relieving, reducing, alleviating, ameliorating or otherwise inhibiting the condition, or a symptom thereof, for at least a period of time. It is also to be understood that terms "treating", "treatment" and the like do not imply that the condition, or a symptom thereof, is permanently relieved, reduced, alleviated, ameliorated or otherwise inhibited and therefore also encompasses the temporary relief, reduction, alleviation, amelioration or otherwise inhibition of the condition, or a symptom thereof.

Without being bound by theory, or by a particular mode of application, neuropathic pain is typically characterised as pain which results from damage by injury or disease to nerve tissue or neurons per se or of dysfunction within nerve tissue. The pain may be peripheral, central or a combination thereof; in other words, the term "neuropathic pain" typically refers to any pain syndrome initiated or caused by a primary lesion or dysfunction in the peripheral or central nervous system. Neuropathic pain is also distinguishable in that it typically does not respond effectively to treatment by common pain medication such as opioids. By contrast, nociceptive pain is characterised as pain which results from stimulation of nociceptors by noxious or potentially harmful stimuli that may cause damage or injury to tissue. Nociceptive pain is typically responsive to common pain medication, such as opioids.

The term "analgesia" is used herein to describe states of reduced pain perception, including absence from pain sensations, as well as states of reduced or absent sensitivity to noxious stimuli. Such states of reduced or absent pain perception are typically induced by the administration of a pain-controlling agent or agents and occur without loss of consciousness, as is commonly understood in the art. Suitable methods for determining whether a compound is capable of providing an analgesic effect will be familiar to persons skilled in the art, illustrative examples of which include the use of animal models of neuropathic pain, such as chronic constriction injury, spinal nerve ligation and partial sciatic nerve ligation (see Bennett et al. (2003); Curr. Protoc. Neurosci., Chapter 9, Unit 9.14) and animal models of nociceptive pain, such as formalin-, carrageenan- or complete Freund's adjuvant (CFA)-induced inflammatory pain. Other suitable models of pain are discussed in Gregory et al (2013, J. Pain.; 14(11); "An overview of animal models of pain: disease models and outcome measures").

As persons skilled in the art will know, there are many possible causes of neuropathy and neuropathic pain. It is therefore to be understood that contemplated herein is the treatment or prevention of neuropathic pain regardless of cause. In some embodiments, neuropathic pain is a result of a disease or condition affecting the nerves (primary neuropathy) and/or neuropathy that is caused by systemic disease (secondary neuropathy), illustrative examples of which include diabetic neuropathy; Herpes Zoster (shingles)-related neuropathy; fibromyalgia; multiple sclerosis, stroke, spinal cord injury; chronic post-surgical pain, phantom limb pain, Parkinson's disease; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tomaculous neuropathy; neuropathy caused by nutritional deficiency, neuropathy caused by kidney failure and complex regional pain syndrome. Other illustrative examples of conditions that may cause neuropathic pain include repetitive activities such as typing or working on an assembly line, medications known to cause peripheral neuropathy such as several anti-retroviral drugs ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillain-Barre syndrome). Other illustrative examples of neuropathic pain include thermal or mechanical hyperalgesia, thermal or mechanical allodynia, diabetic pain, neuropathic pain affecting the oral cavity (e.g., trigeminal neuropathic pain, atypical odontalgia (phantom tooth pain), burning mouth syndrome), fibromyalgia and entrapment pain.

In an embodiment disclosed herein, the neuropathic pain is selected from the group consisting of diabetic neuropathy; Herpes Zoster (shingles)-related neuropathy; fibromyalgia; multiple sclerosis, stroke, spinal cord injury; chronic post-surgical pain, phantom limb pain, Parkinson's disease; uremia-associated neuropathy; amyloidosis neuropathy; HIV sensory neuropathy; hereditary motor and sensory neuropathy (HMSN); hereditary sensory neuropathy (HSN); hereditary sensory and autonomic neuropathy; hereditary neuropathy with ulcero-mutilation; nitrofurantoin neuropathy; tomaculous neuropathy; neuropathy caused by nutritional deficiency, neuropathy caused by kidney failure, trigeminal neuropathic pain, atypical odontalgia (phantom tooth pain), burning mouth syndrome, complex regional pain syndrome, repetitive strain injury, drug-induced peripheral neuropathy, peripheral neuropathy associated with infection, allodynia, hyperesthesia, hyperalgesia, burning pain and shooting pain.

In some embodiments, the neuropathic pain may be accompanied by numbness, weakness and loss of reflexes. The pain may be severe and disabling. By "hyperalgesia" is meant an increased response to a stimulus that is not normally painful. A hyperalgesia condition is one that is associated with pain caused by a stimulus that is not normally painful. The term "hyperesthesia" refers to an excessive physical sensitivity, especially of the skin. The term "allodynia" as used herein refers to the pain that results from a non-noxious stimulus; that is, pain due to a stimulus that does not normally provoke pain. Illustrative examples of allodynia include thermal allodynia (pain due to a cold or hot stimulus), tactile allodynia (pain due to light pressure or touch), mechanical allodynia (pain due to heavy pressure or pinprick) and the like.

Neuropathic pain may be acute or chronic and, in this context, it is to be understood that the time course of a neuropathy may vary, based on its underlying cause. For instance, with trauma, the onset of neuropathic pain or symptoms of neuropathic pain may be acute, or sudden; however, the most severe symptoms may develop over time and persist for years. A chronic time course over weeks to months usually indicates a toxic or metabolic neuropathy. A chronic, slowly progressive neuropathy, such as occurs with painful diabetic neuropathy or with most hereditary neuropathies or with a condition termed chronic inflammatory demyelinating polyradiculoneuropathy (CIDP), may have a time course over many years. Neuropathic conditions with symptoms that relapse and remit include Guillain-Barré syndrome.

In some embodiments, neuropathic pain results from a condition characterised by neuronal hypersensitivity, such as fibromyalgia or irritable bowel syndrome.

In other embodiments, neuropathic pain results from a disorder associated with aberrant nerve regeneration resulting in neuronal hypersensitivity. Such disorders include breast pain, interstitial cystitis, vulvodynia and cancer chemotherapy-induced neuropathy.

In some embodiments, the neuropathic pain is related to surgery, pre-operative pain and post-operative pain, particularly post-operative neuropathic pain.

The term "allodynia" as used herein refers to the pain that results from a non-noxious stimulus i.e., pain due to a stimulus that does not normally provoke pain. Examples of allodynia include, but are not limited to, cold allodynia, tactile allodynia (pain due to light pressure or touch), and the like.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

By "hyperalgesia" is meant an increased response to a stimulus that is not normally painful. A hyperalgesia condition is one that is associated with pain caused by a stimulus that is not normally painful.

The term "hyperesthesia" refers to an excessive physical sensitivity, especially of the skin.

The term "subject", as used herein, refers to a mammalian subject for whom treatment or prophylaxis is desired. Illustrative examples of suitable subjects include primates, especially humans, companion animals such as cats and dogs and the like, working animals such as horses, donkeys and the like, livestock animals such as sheep, cow's, goats, pigs and the like, laboratory test animals such as rabbits, mice, rats, guinea pigs, hamsters and the like and captive wild animals such as those in zoos and wildlife parks, deer, dingoes and the like. In an embodiment, the subject is a human. In another embodiment, the subject is selected from the group consisting of a canine, a feline and an equine.

It is to be understood that a reference to a subject herein does not imply that the subject has the condition, or a symptom thereof, but also includes a subject that is at risk of developing the condition, or a symptom thereof. In an embodiment, the subject has (i.e., is experiencing) the condition, or a symptom thereof, hi another embodiment, the subject does not have the condition, or a symptom thereof at the time of treatment, but is at risk of developing the condition, or a symptom thereof. In an illustrative example, the subject has a condition that puts the subject at risk of developing neuropathic pain, for example, poorly managed diabetes, which may lead to a diabetic neuropathy. In another embodiment, the subject has had a condition that has potential to result in neuropathic pain, such as herpes zoster (shingles), which may lead to post-herpetic neuralgia.

There are many possible causes of neuropathy and neuropathic pain and it will be understood that the present invention contemplates the treatment or prevention of neuropathic pain symptoms of any neuropathic condition regardless of the cause. In some embodiments, the neuropathic conditions are a result of diseases of the nerves (primary neuropathy) and neuropathy that is caused by systemic disease (secondary neuropathy) such as but not limited to: diabetic neuropathy; Herpes Zoster (shingles)-related neuropathy; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tomaculous neuropathy; neuropathy caused by nutritional deficiency, neuropathy caused by kidney failure and complex regional pain syndrome. Other causes include repetitive activities such as typing or working on an assembly line, medications known to cause peripheral neuropathy such as several anti-retroviral drugs ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillain-Barre syndrome).

As persons skilled in the art will know, there are many possible causes of neuropathy and neuropathic pain. It is therefore to be understood that contemplated herein is the treatment or prevention of neuropathic pain regardless of cause. In some embodiments, neuropathic pain is a result of a disease or condition affecting the nerves (primary neuropathy) and/or neuropathy that is caused by systemic disease (secondary neuropathy), illustrative examples of which include diabetic neuropathy; Herpes Zoster (shingles)-related neuropathy; fibromyalgia; multiple sclerosis, stroke, spinal cord injury; chronic post-surgical pain, phantom limb pain, Parkinson's disease; uremia-associated neuropathy; amyloidosis neuropathy: HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tomaculous neuropathy; neuropathy caused by nutritional deficiency, neuropathy caused by kidney failure and complex regional pain syndrome. Other illustrative examples of conditions that may cause neuropathic pain include repetitive activities such as typing or working on an assembly line, medications known to cause peripheral neuropathy such as several anti-retroviral drugs ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillain-Barre syndrome). Other illustrative examples of neuropathic pain include thermal or mechanical hyperalgesia, thermal or mechanical allodynia, diabetic pain, neuropathic pain affecting the oral cavity (e.g., trigeminal neuropathic pain, atypical odontalgia (phantom tooth pain), burning mouth syndrome), fibromyalgia and entrapment pain.

In an embodiment disclosed herein, the neuropathic pain is selected from the group consisting of diabetic neuropathy; Herpes Zoster (shingles)-related neuropathy; fibromyalgia; multiple sclerosis, stroke, spinal cord injury; chronic post-surgical pain, phantom limb pain, Parkinson's disease; uremia-associated neuropathy; amyloidosis neuropathy; HIV sensory neuropathy; hereditary motor and sensory neuropathy (HMSN); hereditary sensory neuropathy (HSN); hereditary sensory and autonomic neuropathy; hereditary neuropathy with ulcero-mutilation; nitrofurantoin neuropathy; tomaculous neuropathy; neuropathy caused by nutritional deficiency, neuropathy caused by kidney failure, trigeminal neuropathic pain, atypical odontalgia (phantom tooth pain), burning mouth syndrome, complex regional pain syndrome, repetitive strain injury, drug-induced peripheral neuropathy, peripheral neuropathy associated with infection, allodynia, hyperesthesia, hyperalgesia, burning pain and shooting pain.

The neuropathic condition may be acute or chronic and, in this connection, it will be understood by persons of skill in the art that the time course of a neuropathy will vary, based on its underlying cause. With trauma, the onset of symptoms may be acute, or sudden; however, the most severe symptoms may develop over time and persist for years. A chronic time coarse over weeks to months usually indicates a toxic or metabolic neuropathy. A chronic, slowly progressive neuropathy such as occurs with painful diabetic neuropathy or with most hereditary neuropathies or with a condition termed chronic inflammatory demyelinating polyradiculoneuropathy (CIDP) may have a time course over many years. Neuropathic conditions with symptoms that relapse and remit include the Guillain-Barré syndrome.

In some embodiments, the neuropathic pain results from a condition characterised by neuronal hypersensitivity, such as fibromyalgia or irritable bowel syndrome.

In other embodiments, the neuropathic pain results from a disorder associated with aberrant nerve regeneration resulting in neuronal hypersensitivity. Such disorders include breast pain, interstitial cystitis, vulvodynia and cancer chemotherapy-induced neuropathy.

In yet other embodiments, the neuropathic pain may occur together with other types of pain, such as inflammatory pain. For example, the neuropathic pain may be a symptom of osteoarthritis or rheumatoid arthritis. In other embodiments, pain symptoms related to inflammatory pain are excluded.

In some embodiments, the neuropathic pain is related to surgery, pre-operative pain and post-operative pain, particularly post-operative neuropathic pain.

The peptides of formula (I), or pharmaceutically acceptable salts thereof, are to be administered in a therapeutically effective amount. The phrase "therapeutically effective amount" typically means an amount necessary to attain the desired response, or to delay the onset or inhibit progression or halt altogether, the onset or progression of neuropathic pain being treated. It would be understood by persons skilled in the art that the therapeutically effective amount of peptide will vary depending upon several factors, illustrative examples of which include the health and physical condition of the subject to be treated, the taxonomic group of subject to be treated, the severity of the neuropathic pain to be treated, the formulation of the composition comprising a peptide of formula (I), or a pharmaceutically acceptable salt thereof, the route of administration, and combinations of any of the foregoing.

The therapeutically effective amount will typically fall within a relatively broad range that can be determined through routine trials by persons skilled in the art. Illustrative examples of a suitable therapeutically effective amount of the peptides of formula (I), or pharmaceutically acceptable salts thereof, for administration to a human subject include from about 0.001 mg per kg of body weight to about 1 g per kg of body weight, preferably from about 0.001 mg per kg of body weight to about 50 mg per kg of body weight, more preferably from about 0.01 mg per kg of body weight to about 1.0 mg per kg of body weight. In an embodiment disclosed herein, the therapeutically effective amount of the peptide of formula (I), or pharmaceutically acceptable salts thereof, is from about 0.001 mg per kg of body weight to about 1 g per kg of body weight per dose (e.g., 0.001 mg/kg, 0.005 mg/kg, 0.01 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 15.5 mg/kg, 16 mg/kg, 16.5 mg/kg, 17 mg/kg, 17.5 mg/kg, 18 mg kg, 18.5 mg/kg, 19 mg/kg, 19.5 mg/kg, 20 mg/kg, 20.5 mg/kg, 21 mg/kg, 21.5 mg/kg, 22 mg/kg, 22.5 mg/kg, 23 mg/kg, 23.5 mg/kg, 24 mg/kg, 24.5 mg/kg, 25 mg/kg, 25.5 mg/kg, 26 mg/kg, 26.5 mg/kg, 27 mg/kg, 27.5 mg/kg, 28 mg/kg, 28.5 mg/kg, 29 mg/kg, 29.5 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg of body weight, etc). In an embodiment, the therapeutically effective amount of the peptides of formula (I), or pharmaceutically acceptable salts thereof, is from about 0.001 mg to about 50 mg per kg of body weight. In an embodiment, the therapeutically effective amount of the peptides of formula (I), or pharmaceutically acceptable salts thereof, is from about 0.01 mg to about 1.0 mg per kg of body weight. Dosage regimes may be adjusted to provide the optimum therapeutic response, depending, for example, on the condition to be treated. For instance, several divided closes may be administered daily, weekly, monthly or other suitable time intervals, or the dose may be proportionally reduced as indicated by the exigencies of the situation.

In an embodiment disclosed herein, the peptide of formula (I), or the pharmaceutically acceptable salt thereof, is administered to the subject at a therapeutically effective amount that alleviates neuropathic pain in the subject in the absence of a therapeutically effective analgesic effect on nociceptive pain.

By "therapeutically effective analgesic effect on nociceptive pain" is meant a reduction, either partial or complete, of a subject's perception of nociceptive pain. Thus, the absence of a therapeutically effective analgesic effect on nociceptive pain can be characterised, in an embodiment, by the subject retaining the ability to perceive a stimulus of nociceptive pain, to the same or substantially the same degree as if the subject had not received the peptide of formula (I), or pharmaceutically acceptable salts thereof, despite a reduction of neuropathic pain. In an embodiment, the peptide of formula (I), or a pharmaceutically acceptable salt thereof, is not therapeutically effective for the treatment of nociceptive pain at a dosage suitable for treating neuropathic pain.

In other embodiments, the peptide of formula (I), or a pharmaceutically acceptable salt thereof, is administered to the subject at a therapeutically effective amount that alleviates neuropathic pain in the subject with some, but otherwise a therapeutically ineffective, analgesic effect on nociceptive pain. The term "therapeutically ineffective analgesic effect on nociceptive pain" means there is either no discernible analgesic effect on nociceptive pain or a partial analgesic effect on nociceptive pain, but that the subject is still capable of perceiving a stimulus of nociceptive pain.

In some embodiments, the peptides of formula (I), or pharmaceutically acceptable salts thereof, are administered together with another therapy to treat or alleviate neuropathic pain or the underlying condition that is causing the neuropathic pain. In some embodiments, the amount of the second drug may be reduced when administration is together with a peptide of formula (I) or a pharmaceutically acceptable salt thereof.

Suitable additional drugs to treat pain include opiates such as morphine, codeine, dihydrocodeine, hydrocodone, acetyldihydrocodeine, oxycodone, oxymorphone and buprenorphine, and non-steroidal anti-inflammatory drugs (NSAIDs) such as aspirin, ibuprofen, naproxen, acetaminophen, diflunisal, salsalate, phenacetin, fenoprofen, ketoprofen, flurbiprofen, oxaprozin, loxoprofen, indomethacin, sulindac, etodolac, ketorolac, diclofenac, nabumetone, mefenamic acid, meclofenamic acid, flufenamic acid, tolfenamic acid, celecoxib, parecoxib, lumaricoxib, etoricoxib, firocoxib, rimesulide and licofelone.

Examples of drugs to treat neuropathies include duloxetine, pregabalin, gabapentin, phenyloin, carbamazebine, levocarnitine, tricyclic antidepressants such as amitryptyline and sodium channel blockers such as lidocaine.

Routes of Administration

The peptides of formula (I), and pharmaceutically acceptable salts thereof, may be administered to the subject by any suitable route that allows for delivery of the peptides to the subject at a therapeutically effective amount, as herein described. Suitable routes of administration will be known to persons skilled in the art, illustrative examples of which include enteral routes of administration (e.g., oral and rectal), parenteral routes of administration, typically by injection or microinjection (e.g., intramuscular, subcutaneous, intravenous, epidural, intra-articular, intraperitoneal, intracisternal or intrathecal) and topical (transdermal or transmucosal) routes of administration (e.g., buccal, sublingual, vaginal, intranasal or by inhalation). The peptides of formula (I), and pharmaceutically acceptable salts thereof, may also suitably be administered to the subject as a controlled release dosage form to provide a controlled release of the active agent(s) over an extended period of time. The term "controlled release" typically means the release of the active agent(s) to provide a constant, or substantially constant, concentration of the active agent in the subject over a period of time (e.g., about eight hours up to about 12 hours, up to about 14 hours, up to about 16 hours, up to about 18 hours, up to about 20 hours, up to a day, up to a week, up to a month, or more than a month). Controlled release of the active agent(s) can begin within a few minutes after administration or after expiration of a delay period (lag time) after administration, as may be required. Suitable controlled release dosage forms will be known to persons skilled in the art, illustrative examples of which are described in Anal, A. K. (2010; Controlled-Release Dosage Forms. Pharmaceutical Sciences Encyclopedia. 11:1-46).

Without being bound by theory or by a particular mode of application, it may be desirable to elect a route of administration on the basis of whether the condition to be treated is localized or generalised. For example, where the neuropathic pain is localized, it may be desirable to administer the peptides to the affected area or to an area immediately adjacent thereto. For instance, where the neuropathic pain is in a joint (e.g., neck, knee, elbow, shoulder, hip, etc.), the peptides can be administered to the subject intra-articularly into the affected joint. Alternatively, or in addition, the peptide of formula (I), or pharmaceutically acceptable salts thereof, can be administered at, or substantially adjacent to, the affected joint. As another illustrative example, where the neuropathic pain is in the oral cavity (e.g., trigeminal neuropathic pain, atypical odontalgia (phantom tooth pain) or burning mouth syndrome), the peptides can be formulated for administration via the oral mucosa (e.g., by buccal and/or sublingual administration). Conversely, where the neuropathic pain is generalised or disseminated across multiple anatomical sites of a subject, the peptides may be administered topically, enterally and/or parenterally at any site with a view to distributing the active peptides across the multiple anatomical sites affected by neuropathic pain. In an embodiment disclosed herein, the peptides of formula (I), or pharmaceutically acceptable salts thereof, are administered to the subject enterally. In an embodiment disclosed herein, the peptides of formula (I), or pharmaceutically acceptable salts thereof, are administered to the subject orally. In an embodiment disclosed herein, the peptides of formula (I), or pharmaceutically acceptable salts thereof, are administered to the subject parenterally. In another embodiment disclosed herein, the peptides of formula (I), or pharmaceutically acceptable salts thereof, are administered to the subject topically. As described elsewhere herein, "topical" administration typically means application of the active agents to a surface of the body, such as the skin or mucous membranes, suitably in the form of a cream, lotion, foam, gel, ointment, nasal drop, eye drop, ear drop, transdermal patch, transdermal film (e.g., sublingual film) and the like. Topical administration also encompasses administration via the mucosal membrane of the respiratory tract by inhalation or insufflation. In an embodiment disclosed herein, the topical administration is selected from the group consisting of transdermal and transmucosal administration. In an embodiment, the peptides of formula (I), or pharmaceutically acceptable salts thereof, are administered to the subject transdermally.

In an embodiment, the methods comprise orally administering the peptide of formula (I), or a pharmaceutically acceptable salt thereof, to a human. In another embodiment, the methods comprise orally administering the peptide of formula (I), or pharmaceutically acceptable salts thereof, to a non-human, subject. In yet another embodiment, the methods comprise orally administering the peptide of formula (I), or a pharmaceutically acceptable salt thereof, to a non-human subject selected from the group consisting of a feline, a canine and an equine.

In an embodiment, the methods comprise administering the peptide of formula (I), or a pharmaceutically acceptable salt thereof, topically to a human. In another embodiment, the methods comprise administering the peptide of formula (I), or a pharmaceutically acceptable salt thereof, topically to a non-human, subject. In yet another embodiment, the methods comprise administering the peptide of formula (I), or a pharmaceutically acceptable salt thereof, topically to a non-human subject selected from the group consisting of a feline, a canine and an equine.

In an embodiment, the methods comprise administering a peptide selected from the group consisting of SEQ ID NOs:26 to 29 or a pharmaceutically acceptable salt thereof, orally to a human. In another embodiment, the methods comprise administering the peptide selected from the group consisting of SEQ ID NOs:26 to 29, or a pharmaceutically acceptable salt thereof, orally to a non-human, subject. In yet another embodiment, the methods comprise administering the peptide selected from the group consisting of SEQ ID NOs:26 to 29, or a pharmaceutically acceptable salt thereof, orally to a non-human subject selected from the group consisting of a feline, a canine and an equine. In an embodiment, the peptide has an amino acid sequence of SEQ ID NO:26. In an embodiment, the peptide has an amino acid sequence of SEQ ID NO:27. In an embodiment, the peptide has an amino acid sequence of SEQ ID NO:28. In an embodiment, the peptide has an amino acid sequence of SEQ ID NO:29.

In another embodiment, the methods comprise administering the peptide selected from the group consisting of SEQ ID NOs:26 to 29, or a pharmaceutically acceptable salt thereof, topically to a human. In another embodiment, the methods comprise administering the peptide selected from the group consisting of SEQ ID NOs:26 to 29, or a pharmaceutically acceptable salt thereof, topically to a non-human, subject. In yet another embodiment, the methods comprise administering the peptide selected from the group consisting of SEQ ID NOs:26 to 29, or a pharmaceutically acceptable salt thereof, topically to a non-human subject selected from the group consisting of a feline, a canine and an equine. In an embodiment, the peptide has an amino acid sequence of SEQ ID NO:26. In an embodiment, the peptide has an amino acid sequence of SEQ ID NO:27. In an embodiment, the peptide has an amino acid sequence of SEQ ID NO:28. In an embodiment, the peptide has an amino acid sequence of SEQ ID NO:29.

Illustrative examples of topical administration are described elsewhere herein. In an embodiment, the topical administration is transdermal.

In an embodiment disclosed herein, the peptides of formula (I), or pharmaceutically acceptable salts thereof, are administered to the subject as a controlled release dosage form, illustrative examples of which are described elsewhere herein. In an embodiment, the methods comprise administering the peptide of formula (I), or a pharmaceutically acceptable salt thereof, to a human as a controlled release dosage form. In another embodiment, the methods comprise administering the peptide of formula (I), or pharmaceutically acceptable salts thereof, to a non-human subject as a controlled release dosage form. In yet another embodiment, the methods comprise administering the peptide of formula (I), or a pharmaceutically acceptable salt thereof, as a controlled release dosage form to a non-human subject selected from the group consisting of a feline, a canine and an equine.

In another embodiment, the methods comprise administering the peptide selected from the group consisting of SEQ ID NOs:26 to 29, or a pharmaceutically acceptable salt thereof, to a human as a controlled release dosage form. In another embodiment, the methods comprise administering the peptide selected from the group consisting of SEQ ID NOs:26 to 29, or a pharmaceutically acceptable salt thereof, to a non-human subject as a controlled release dosage form. In yet another embodiment, the methods comprise administering the peptide selected from the group consisting of SEQ ID NOs:26 to 29, or a pharmaceutically acceptable salt thereof, as a controlled release dosage form to a non-human subject selected from the group consisting of a feline, a canine and an equine. In an embodiment, the peptide has an amino acid sequence of SEQ ID NO:26. In an embodiment, the peptide has an amino acid sequence of SEQ ID NO:27. In an embodiment, the peptide has an amino acid sequence of SEQ ID NO:28. In an embodiment, the peptide has an amino acid sequence of SEQ ID NO:29.

As noted elsewhere herein, several (i.e., multiple) divided doses may be administered daily, weekly, monthly or other suitable time intervals, or the dose may be proportionally reduced as indicated by the exigencies of the situation. Where a course of multiple doses is required or otherwise desired, it may be beneficial to administer the peptides, as herein disclosed, via more than one route. For example, where the condition to be treated is neuropathic pain, it may be desirable to administer a first dose parenterally (e.g., via intramuscular, intravenous; subcutaneous, epidural, intra-articular, intraperitoneal, intracisternal or intrathecal routes of administration) to induce a rapid or otherwise acute analgesic effect in a subject, followed by a subsequent (e.g., second, third, fourth, fifth, etc) dose administered enterally (e.g., orally or rectally) and/or topically (e.g., via transdermal or transmucosal routes of administration) to provide continuing availability of the active agent over an extended period subsequent to the acute phase of treatment. Alternatively, it may be desirable to administer a dose enterally (e.g., orally or rectally), followed by a subsequent (e.g., second, third, fourth, fifth, etc) dose administered parenterally (e.g., via intramuscular, intravenous; subcutaneous, epidural, intra-articular, intraperitoneal, intracisternal or intrathecal routes of administration) and/or topically (e.g., via transdermal or transmucosal routes of administration). Alternatively, it may be desirable to administer a dose topically (e.g., via transdermal or transmucosal routes of administration), followed by a subsequent (e.g., second, third, fourth, fifth, etc) dose administered parenterally (e.g., via intramuscular, intravenous; subcutaneous, epidural, intra-articular, intraperitoneal, intracisternal or intrathecal routes of administration) and/or enterally (e.g., orally or rectally).

The route of administration may suitably be selected on the basis of whether the condition to be treated (e.g., neuropathic pain) is localised or generalised, as discussed elsewhere herein. Alternatively, or in addition, the route of administration may suitably be selected having regard to factors such as the subject's general health, age, weight and tolerance (or a lack thereof) for given routes of administration (e.g., where there is a phobia of needles, an alternative route of administration may be selected, such as enteral and/or topical).

It is also to be understood that, where multiple routes of administration are desired, any combination of two or more routes of administration may be used in accordance with the methods disclosed herein. Illustrative examples of suitable combinations include, but are not limited to, (in order of administration), (a) parenteral-enteral; (b) parenteral-topical; (c) parenteral-enteral-topical: (d) parenteral-topical-enteral; (e) enteral-parenteral; (f) enteral-topical; (g) enteral-topical-parenteral; (h) enteral-parenteral-topical; (i) topical-parenteral; (j) topical-enteral; (k) topical-parenteral-enteral;

(1) topical-enteral-parenteral; (m) parenteral-enteral-topical-parenteral; (n) parenteral-enteral-topical-enteral; etc.

In an embodiment, the methods comprise (i) parenterally administering to the subject the peptides or compositions, as disclosed herein, and (ii) non-parenterally (i.e, enterally or topically) administering to the subject the peptides or compositions, as disclosed herein, wherein the non-parenteral (enteral or topical) administration is subsequent to the parenteral administration. In an embodiment, the parental administration is selected from the group consisting of intramuscular, subcutaneous and intravenous. In a further embodiment, the parental administration is subcutaneous. In an embodiment, the non-parental administration is oral.

In an embodiment, the methods disclosed herein comprise (i) parenterally administering to a human subject the peptide of formula (I), or a pharmaceutically acceptable salt thereof, and (ii) orally administering to the human subject the peptide of formula (I), or a pharmaceutically acceptable salt thereof, wherein the oral administration is subsequent to the parenteral administration. In another embodiment, the methods disclosed herein comprise (i) parenterally administering to a human subject the peptide selected from the group consisting of SEQ ID NOs:26 to 29, or a pharmaceutically acceptable salt thereof, and (ii) orally administering to the human subject the peptide selected from the group consisting of SEQ ID NOs:26 to 29, or a pharmaceutically acceptable salt thereof, wherein the oral administration is subsequent to the parenteral administration. In an embodiment, the parental administration is subcutaneous. In another embodiment, the parental administration is intrathecal. In an embodiment, the peptide has an amino acid sequence of SEQ ID NO:26. In an embodiment, the peptide has an amino acid sequence of SEQ ID NO:27. In an embodiment, the peptide has an amino acid sequence of SEQ ID NO:28. In an embodiment, the peptide has an amino acid sequence of SEQ ID NO:29.

In a further embodiment, the methods disclosed herein comprise (i) parenterally administering to a human subject the peptide of formula (I), or a pharmaceutically acceptable salt thereof, and (ii) topically administering to the human subject the peptide of formula (I), or a pharmaceutically acceptable salt thereof, wherein the topical administration is subsequent to the parenteral administration. In a further embodiment, the methods disclosed herein comprise (i) parenterally administering to a human subject the peptide selected from the group consisting of SEQ ID NOs:26 to 29, or a pharmaceutically acceptable salt thereof, and (ii) topically administering to the human subject the peptide selected from the group consisting of SEQ ID NOs:26 to 29, or a pharmaceutically acceptable salt thereof, wherein the topical administration is subsequent to the parenteral administration. In an embodiment, the peptide has an amino acid sequence of SEQ ID NO:26. In an embodiment, the peptide has an amino acid sequence of SEQ ID NO:27. In an embodiment, the peptide has an amino acid sequence of SEQ ID NO:28. In an embodiment, the peptide has an amino acid sequence of SEQ ID NO:29.

In an embodiment, the non-human subject is selected from the group consisting of a feline, a canine and an equine. In an embodiment, the parenteral route of administration is subcutaneous. In another embodiment, the topical route of administration is transdermal. In another embodiment, the parenteral administration is subcutaneous and the topical administration is transdermal.

Alternatively, or in addition, the peptides and compositions as herein described may suitably be administered as a controlled release dosage form. Thus, in an embodiment, the methods comprise (i) parenterally administering to the subject the peptides or compositions, as disclosed herein, and (ii) administering to the subject the peptides or compositions, as disclosed herein, as a controlled release dosage form, wherein the controlled release dosage form is administered subsequent to the parenteral administration. In another embodiment, the methods comprise (i) non-parenterally (enterally or topically) administering to the subject the peptides or compositions, as disclosed herein, and (ii) administering to the subject the peptides or compositions, as disclosed herein, as a controlled release dosage form, wherein the controlled release dosage form is administered to the subject subsequent to the non-parenteral administration. In yet another embodiment, the methods comprise (i) enterally administering to the subject the peptides or compositions, as disclosed herein, and (ii) administering to the subject the peptides or compositions, as disclosed herein, as a controlled release dosage form, wherein the controlled release dosage form is administered to the subject subsequent to the enteral administration. In yet another embodiment, the methods comprise (i) topically administering to the subject the peptides or compositions, as disclosed herein, and (ii) administering to the subject the peptides or compositions, as disclosed herein, as a controlled release dosage form, wherein the controlled release dosage form is administered to the subject subsequent to the topical administration. In a preferred embodiment, the controlled release dosage form is formulated for parenteral administration.

Adjunct Therapy

The peptides of formula (I), or pharmaceutically acceptable salts thereof, may suitably be administered together, either sequentially or in combination (e.g., as an admixture), with one or more another active agents. It will be understood by persons skilled in the art that the nature of the other active agents will depend on the condition to be treated or prevented. For example, where the subject has cancer, the peptides of formulae (I), or pharmaceutically acceptable salts thereof, may be administered to the subject together, either sequentially or in combination (e.g., as an admixture), with one or more chemotherapeutic agents, illustrative examples of which will be familiar to persons skilled in the art. Combination treatments of this nature can be advantageous by alleviating the neuropathic pain that is often associated with some chemotherapeutic agents, illustrative examples of which include cisplatin, carboplatin, oxaliplatin, vincristine, docetaxel, paclitaxel, izbepilone, bortezomib, thalidomide and lenalinomide. Thus, in an embodiment, the methods disclosed herein further comprise administering to the subject a therapeutically effective amount of a chemotherapeutic agent.

The peptides of formula (I), or pharmaceutically acceptable salts thereof, may also be suitably administered to the subject together, either sequentially or in combination (e.g., as an admixture), with one or more other analgesic agents capable of alleviating pain in the subject (i.e., other than the peptides of formula (I) and pharmaceutically acceptable salts thereof). Suitable analgesic agents will be familiar to persons skilled in the art, illustrative examples of which include analgesic agents capable of alleviating nociceptive pain, agents capable of alleviating neuropathic pain, or any combination thereof. Thus, in an embodiment, the methods disclosed herein further comprise administering to the subject a therapeutically effective amount of a second agent capable of alleviating pain in the subject, wherein the second agent is not the peptide of formula (I), or a pharmaceutically acceptable salt thereof.

In an embodiment, the second agent is capable of alleviating nociceptive pain in the subject. In another embodiment, the second agent is capable of alleviating neuropathic pain in the subject.

Suitable agents capable of alleviating nociceptive pain will be familiar to persons skilled in the art, illustrative examples of which include opiates such as morphine, codeine, dihydrocodeine, hydrocodone, acetyldihydrocodeine, oxycodone, oxymorphone and buprenorphine, and non-steroidal anti-inflammatory drugs (NSAIDs) such as aspirin, ibuprofen, naproxen, acetaminophen, diflunisal, salsalate, phenacetin, fenoprofen, ketoprofen, flurbiprofen, oxaprozin, loxoprofen, indomethacin, sulindac, etodolac, ketorolac, diclofenac, nabumetone, mefenamic acid, meclofenamic acid, flufenamic acid, tolfenamic acid, celecoxib, parecoxib, lumaricoxib, etoricoxib, firocoxib, rimesulide and licofelone. In an embodiment, the second agent capable of alleviating nociceptive pain is an opioid.

In other embodiments disclosed herein, the peptides of formula (I), or pharmaceutically acceptable salts thereof, are administered together, either sequentially or in combination (e.g., as an admixture), with another therapy to treat or alleviate neuropathic pain or the underlying condition that is causing the neuropathic pain. In some instances, the amount of the second neuropathic analgesic agent may be reduced when administration is together with a peptide of formula (I), or pharmaceutically acceptable salts thereof. Illustrative examples of suitable agents capable of treating neuropathic pain include duloxetine, pregabalin, gabapentin, phenytoin, melatonin, carbamazepine, levocarnitine, capsaicin, tricyclic antidepressants such as amitryptyline and sodium channel blockers such as lidocaine. The peptides of formula (I), or pharmaceutically acceptable salts thereof, may also be suitably administered to the subject together, either sequentially or in combination (e.g., as an admixture), with one or more other agents for treating an inflammatory condition, such as osteoarthritis (i.e., other than the peptides of formula (I) and pharmaceutically acceptable salts thereof). Suitable agents for treating inflammatory conditions such as osteoarthritis will be familiar to persons skilled in the art, illustrative examples of which include hyaluronic acid (HA), corticosteroids, non-steroidal anti-inflammatory agents (e.g., aspirin, ibuprofen, naproxen sodium), analgesics (e.g., acetaminophen, paracetamol, codeine, opioids) or any combination thereof. In an embodiment, the methods disclosed herein further comprise administering to the subject a therapeutically effective amount of hyaluronic acid.

Pharmaceutical Compositions

The peptides of formula (I), or pharmaceutically acceptable salts thereof, may be formulated for administration to a subject as a neat chemical. However, in certain embodiments, it may be preferable to formulate the peptides of formula (I), or pharmaceutically acceptable salts thereof, as pharmaceutical or veterinary compositions. Thus, in another aspect disclosed herein, there is provided a peptide of formula (I), or a pharmaceutically acceptable salt thereof, as herein described, for use in treating a condition selected from the group consisting of sarcopenia, impaired glucose tolerance, diabetes, obesity, metabolic disease and obesity-related conditions, osteoarthritis, a disorder of muscle, a wasting disorder, cachexia, anorexia, AIDS wasting syndrome, muscular dystrophy, neuromuscular disease, motor neuron disease, diseases of the neuromuscular junction, inflammatory myopathy, a burn, injury or trauma, a condition associated with elevated LDL cholesterol, a condition associated with impaired chondrocyte, proteoglycan or collagen production or quality, a condition associated with impaired cartilage tissue formation or quality, a condition that requires skin or wound repair, a condition associated with impaired muscle, ligament or tendon mass, form or function, a condition associated with inflammation, trauma or a genetic abnormality affecting muscle or connective tissue, a bone disorder, migraine and pain (e.g., neuropathic pain).

In an embodiment, the condition is neuropathic pain.

In an embodiment, the peptide of formula (I), or a pharmaceutically acceptable salt thereof, is present in a therapeutically effective amount that, when administered to a subject, alleviates neuropathic pain in the subject in the absence of a therapeutically effective analgesic effect on nociceptive pain, as described elsewhere herein.

In an embodiment, the composition further comprises a second agent capable of alleviating pain in the subject, wherein the second agent is not the peptide of formula (I) or a pharmaceutically acceptable salt thereof. In an embodiment, the second agent is capable of alleviating nociceptive pain in the subject, illustrative examples of which are described elsewhere herein. In another embodiment, the second agent is capable of alleviating neuropathic pain in the subject, illustrative examples of which are also described elsewhere herein. In an embodiment the second agent is an opioid.

In another aspect disclosed herein, there is provided a use of a peptide of formula (I), or a pharmaceutically acceptable salt thereof, as described herein, in the manufacture of a medicament for the treatment of a condition selected from the group consisting of sarcopenia, impaired glucose tolerance, diabetes, obesity, metabolic disease and obesity-related conditions, neuropathic pain, osteoarthritis, a disorder of muscle, a wasting disorder, cachexia, anorexia, AIDS wasting syndrome, muscular dystrophy, neuromuscular disease, motor neuron disease, diseases of the neuromuscular junction, inflammatory myopathy, a burn, injury or trauma, a condition associated with elevated LDL cholesterol, a condition associated with impaired chondrocyte, proteoglycan or collagen production or quality, a condition associated with impaired cartilage tissue formation or quality, a condition that requires skin or wound repair, a condition associated with impaired muscle, ligament or tendon mass, form or function, a condition associated with inflammation, trauma or a genetic abnormality affecting muscle or connective tissue, a bone disorder, migraine and neuropathic pain.

In an embodiment disclosed herein, the condition is neuropathic pain.

In an embodiment, the peptide of formula (I), or the pharmaceutically acceptable salt thereof, is formulated for administration to the subject in a therapeutically effective amount that alleviates neuropathic pain in the subject in the absence of a therapeutically effective analgesic effect on nociceptive pain, as described elsewhere herein.

In an embodiment, the peptide is formulated for administration sequentially, or in combination, with a second agent capable of alleviating pain in the subject, wherein the second agent is not the peptide of formula (I) or a pharmaceutically acceptable salt thereof, as described elsewhere herein. In an embodiment, the second agent is capable of alleviating nociceptive pain in the subject, illustrative examples of which are described elsewhere herein. In another embodiment, the second agent is capable of alleviating neuropathic pain in the subject, illustrative examples of which are also described elsewhere herein. In an embodiment, the second agent is an opioid.

In an embodiment, the peptide, or the pharmaceutically acceptable salt thereof, is present in a therapeutically effective amount that, when administered to a subject, alleviates neuropathic pain in the subject in the absence of a therapeutically effective analgesic effect on nociceptive pain, as described elsewhere herein.

As noted elsewhere herein, the peptides of formula (I), or pharmaceutically acceptable salts thereof, may be administered together, either sequentially or in combination (e.g., as an admixture), with one or more other active agents that will likely depend on the condition to be treated. For example, where the subject has cancer, the compositions disclosed herein may be formulated for administration together, either sequentially or in combination (e.g., as an admixture), with one or more chemotherapeutic agents, illustrative examples of which will be familiar to persons skilled in the art. Combination treatments of this nature can be advantageous by alleviating the neuropathic pain that is often associated with some chemotherapeutic agents, illustrative examples of which include cisplatin, carboplatin, oxaliplatin, vincristine, docetaxel, paclitaxel, izbepilone, bortezomib, thalidomide and lenalinomide. In another embodiment, the peptides of formula (I), or pharmaceutically acceptable salts thereof, are formulated for administration, either sequentially or in combination (e.g., as an admixture), with a therapeutically effective amount of one or more other agents suitable for treating an inflammatory condition, such as osteoarthritis (i.e., other than the peptides of formula (I) and pharmaceutically acceptable salts thereof). Suitable agents for treating inflammatory conditions such as osteoarthritis are noted elsewhere herein, illustrative examples of which include hyaluronic acid (HA), corticosteroids, non-steroidal anti-inflammatory agents (e.g., aspirin, ibuprofen, naproxen sodium), analgesics (e.g., acetaminophen, paracetamol, codeine, opioids) or any combination thereof. In an embodiment, the peptides of formula (I), or pharmaceutically acceptable salts thereof, are formulated for administration with a therapeutically effective amount of hyaluronic acid.

The compositions disclosed herein may also be suitably formulated for administration to the subject together, either sequentially or in combination (e.g., as an admixture), with one or more other analgesic agents capable of alleviating pain in the subject (i.e., other than the peptides of formula (I), and pharmaceutically acceptable salts thereof), as described elsewhere herein. In an embodiment, the compositions disclosed herein further comprise a second agent capable of alleviating pain in the subject, wherein the second agent is not the peptide of formula (I), or a pharmaceutically acceptable salt thereof.

In an embodiment, the second agent is capable of alleviating nociceptive pain in the subject. In another embodiment, the second agent is capable of alleviating neuropathic pain in the subject.

Suitable agents capable of alleviating nociceptive pain will be familiar to persons skilled in the art, illustrative examples of which include opiates such as morphine, codeine, dihydrocodeine, hydrocodone, acetyldihydrocodeine, oxycodone, oxymorphone and buprenorphine, and non-steroidal anti-inflammatory drugs (NSAIDs) such as aspirin, ibuprofen, naproxen, acetaminophen, diflunisal, salsalate, phenacetin, fenoprofen, ketoprofen, flurbiprofen, oxaprozin, loxoprofen, indomethacin, sulindac, etodolac, ketorolac, diclofenac, nabumetone, mefenamic acid, meclofenamic acid, flufenamic acid, tolfenamic acid, celecoxib, parecoxib, lumaricoxib, etoricoxib, firocoxib, rimesulide and licofelone. In an embodiment, the second agent capable of alleviating nociceptive pain is an opioid.

In other embodiments disclosed herein, the compositions disclosed herein are formulated for administration together, either sequentially or in combination (e.g., as an admixture), with another therapy to treat or alleviate neuropathic pain or the underlying condition that is causing the neuropathic pain. In some instances, the amount of the second neuropathic analgesic agent may be reduced when administration is together with a peptide of formula (I), or pharmaceutically acceptable salts thereof. Illustrative examples of suitable agents capable of treating neuropathic pain include duloxetine, pregabalin, gabapentin, phenytoin, melatonin, carbamazepine, levocarnitine, capsaicin, tricyclic antidepressants such as amitryptyline and sodium channel blockers such as lidocaine.

In an embodiment, the composition further comprises a pharmaceutically acceptable carrier, excipient or diluent, as described elsewhere herein. In an embodiment, the composition is formulated for oral administration.

Illustrative examples of suitable pharmaceutical formulations include those suitable for enteral or parenteral administration, illustrative examples of which are described elsewhere herein, including oral, rectal, buccal, sublingual, vaginal, nasal, topical (e.g., transdermal), intramuscular, subcutaneous, intravenous, epidural, intra-articular and intrathecal.

The peptides of formula (I), or pharmaceutically acceptable salts thereof, may suitably be placed into the form of pharmaceutical compositions and unit dosages thereof to be employed as solids (e.g., tablets or filled capsules) or liquids (e.g., solutions, suspensions, emulsions, elixirs, or capsules filled with the same) for oral use, in the form of ointments, suppositories or enemas for rectal administration, in the form of sterile injectable solutions for parenteral use (e.g., intramuscular, subcutaneous, intravenous, epidural, infra-articular and intrathecal administration); or in the form of ointments, lotions, creams, gels, patches, sublingual strips or films, and the like for parenteral (e.g., topical, buccal, sublingual, vaginal) administration. In an embodiment, the peptides of formula (I), or pharmaceutically acceptable salts thereof, are formulated for topical (e.g., transdermal) delivery. Suitable transdermal delivery systems will be familiar to persons skilled in the art, illustrative examples of which are described by Prausnitz and Langer (2008; *Nature Biotechnol.* 26(11): 1261-1268), the contents of which are incorporated herein by reference. In another embodiment, the peptides of formulae (I), or pharmaceutically acceptable salts thereof, are formulated for sublingual or buccal delivery. Suitable sublingual and buccal delivery systems will be familiar to persons skilled in the art, illustrative examples of which include dissolvable strips or films, as described by Bala et al. (2013; *Int. J. Pharm. Investig.* 3(2):67-76), the contents of which are incorporated herein by reference.

Suitable pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. The peptides of formula (I), or pharmaceutically acceptable salts thereof, as described herein, can be formulated for administration in a wide variety of enteral, topical and/or parenteral dosage forms. Suitable dosage forms may comprise, as the active component, either a peptide of formula (I), pharmaceutically acceptable salts thereof, or combinations of any of the foregoing, as herein described.

As noted elsewhere herein, it may be desirable to elect a route of administration on the basis of whether the neuropathic pain is localized or generalised. For example, where the neuropathic pain is localized, it may be desirable to formulate the compositions disclosed herein for administration to the affected area or to an area immediately adjacent thereto. For instance, where the neuropathic pain is in a joint (e.g., neck, knee, elbow, shoulder or hip), the composition can be formulated for intra-articular administration into the affected joint. Alternatively, or in addition, the composition can be formulated for administration at, or substantially adjacent to, the affected joint. As another illustrative example, where the neuropathic pain is in the oral cavity (e.g., trigeminal neuropathic pain, atypical odontalgia (phantom tooth pain) or burning mouth syndrome), the composition can be formulated for administration via the oral mucosa (e.g., by buccal and/or sublingual administration).

Conversely, where the neuropathic pain is generalised or disseminated across multiple anatomical sites of a subject, it may be convenient to formulate the composition for enteral, topical and/or parenteral route of administration, as described elsewhere herein, with a view to distributing the active agents across the multiple anatomical sites affected by neuropathic pain.

In an embodiment, the composition is formulated for oral administration to a human. In another embodiment, the composition is formulated for oral administration to a non-human subject. In yet another embodiment, the composition is formulated for oral administration to a non-human subject selected from the group consisting of a feline, a canine and an equine.

In another embodiment, the composition is formulated for parenteral administration to a human. In another embodiment, the composition is formulated for parenteral administration to a non-human subject. In yet another embodiment, the composition is formulated for parenteral administration to a non-human subject selected from the group consisting of a feline, a canine and an equine. In an embodiment, the parenteral administration is subcutaneous administration.

In another embodiment, the composition is formulated for topical administration to a human. In another embodiment, the composition is formulated for topical administration to a non-human subject. In yet another embodiment, the composition is formulated for topical administration to a non-human subject selected from the group consisting of a feline, a canine and an equine. In an embodiment, the topical administration is transdermal.

In another embodiment, the composition is formulated as a controlled release dosage form to be administered to a human. In another embodiment, the composition is formulated as a controlled release dosage form to be administered to a non-human subject. In yet another embodiment, the composition is formulated as a controlled release dosage form to be administered to a non-human subject selected from the group consisting of a feline, a canine and an equine. Illustrative examples of suitable controlled release dosage forms are described elsewhere herein.

For preparing pharmaceutical compositions of the peptides of formulae (I), or pharmaceutically acceptable salts thereof, pharmaceutically acceptable carriers can be either solid or liquid. Illustrative examples of solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material. In powders, the carrier may be a finely divided solid which is in a mixture with the finely divided active component. In tablets, the active component may be mixed with the carrier having the necessary binding capacity in suitable proportions and compacted in the shape and size desired.

In some embodiments, the powders and tablets contain from five or ten to about seventy percent of the active compound. Illustrative examples of suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material, providing a capsule in which the active component, with or without earners, is surrounded by a earner. Similarly, cachets and lozenges are also envisaged herein. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The peptides of formulae (I), or pharmaceutically acceptable salts thereof, as described herein, may be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active compound(s) may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also contemplated herein are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis, the peptides of formulae (I), or pharmaceutically acceptable salts thereof, as described herein, may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the peptides used in the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively, or in addition, the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently, the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the peptide will generally have a small particle size for example of the order of 1 to 10 microns or less. Such a particle size may be obtained by means known in the art, for example by micronization.

When desired, formulations adapted to give controlled or sustained release of the active ingredient may be employed, as described elsewhere herein.

In an embodiment, the pharmaceutical preparations, as herein described, are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In an embodiment, the compositions disclosed herein are formulated for oral administration to a human. In yet another embodiment, the compositions disclosed herein are formulated for oral administration to a non-human. In a further embodiment, the compositions disclosed herein are formulated for oral administration to a non-human selected from the group consisting of a feline, a canine and an equine.

In another embodiment, the peptide of formula (I), or a pharmaceutically acceptable salt thereof, as disclosed herein, is formulated for oral administration to a human, subject. In another embodiment, the peptide of formula (I), or a pharmaceutically acceptable salt thereof, as disclosed herein, is formulated for oral administration to a non-human, subject. In yet another embodiment, the peptide of formula (I), or a pharmaceutically acceptable salt thereof, as disclosed herein, is formulated for oral administration to a non-human subject selected from the group consisting of a feline, a canine and an equine.

In another embodiment, the peptide of formula (I), or a pharmaceutically acceptable salt thereof, as disclosed herein, is formulated for topical administration to a human, subject. In yet another embodiment, the peptide of formula (I), or a pharmaceutically acceptable salt thereof, as disclosed herein, is formulated for topical administration to a non-human subject. In another embodiment, the peptide of formula (I), or a pharmaceutically acceptable salt thereof, as disclosed herein, is formulated for topical administration to a non-human subject selected from the group consisting of a feline, a canine and an equine. In an embodiment, the topical administration is transdermal.

In another embodiment, the peptide of formula (I), or a pharmaceutically acceptable salt thereof, as disclosed herein, is formulated for administration to a human subject as a controlled release dosage form. In yet another embodiment, the peptide of formula (I), or a pharmaceutically acceptable salt thereof, as disclosed herein, is formulated for administration to a non-human subject as a controlled release dosage form. In another embodiment, the peptide of formula (I), or a pharmaceutically acceptable salt thereof, as disclosed herein, is formulated for administration to a non-human subject as a controlled release dosage form, wherein the non-human subject is selected from the group consisting of a feline, a canine and an equine. In an embodiment, the controlled release dosage form is formulated for parenteral administration.

In another embodiment, the peptide selected from the group consisting of SEQ ID NOs:26 to 29, or a pharmaceutically acceptable salt thereof, is formulated for oral administration to a human. In another embodiment, the peptide selected from the group consisting of SEQ ID NOs:26 to 29, or a pharmaceutically acceptable salt thereof, is formulated for oral administration to a non-human, subject. In yet another embodiment, the peptide selected from the group consisting of SEQ ID NOs:26 to 29, or a pharmaceutically acceptable salt thereof, is formulated for oral administration to a non-human subject selected from the group consisting of a feline, a canine and an equine. In an embodiment, the peptide has an amino acid sequence of SEQ ID NO:26. In an embodiment, the peptide has an amino acid sequence of SEQ ID NO:27. In an embodiment, the peptide has an amino acid sequence of SEQ ID NO:28. In an embodiment, the peptide has an amino acid sequence of SEQ ID NO:29.

In another embodiment, the peptide selected from the group consisting of SEQ ID NOs:26 to 29, or a pharmaceutically acceptable salt thereof, is formulated for topical administration to a human, subject. In yet another embodiment, the peptide selected from the group consisting of SEQ ID NOs:26 to 29, or a pharmaceutically acceptable salt thereof, is formulated for topical administration to a non-human subject. In another embodiment, the peptide selected from the group consisting of SEQ ID NOs:26 to 29, or a pharmaceutically acceptable salt thereof, as disclosed herein, is formulated for topical administration to a non-human subject selected from the group consisting of a feline, a canine and an equine. In an embodiment, the topical administration is transdermal. In an embodiment, the peptide has an amino acid sequence of SEQ ID NO:26. In an embodiment, the peptide has an amino acid sequence of SEQ ID NO:27. In an embodiment, the peptide has an amino acid sequence of SEQ ID NO:28. In an embodiment, the peptide has an amino acid sequence of SEQ ID NO:29.

In another embodiment, the peptide selected from the group consisting of SEQ ID NOs:26 to 29, or a pharmaceutically acceptable salt thereof, is formulated for administration to a human subject as a controlled release dosage form. In yet another embodiment, the peptide selected from the group consisting of SEQ ID NOs:26 to 29, or a pharmaceutically acceptable salt thereof, is formulated for administration to a non-human subject as a controlled release dosage form. In another embodiment, the peptide selected from the group consisting of SEQ ID NOs:26 to 29, or a pharmaceutically acceptable salt thereof, is formulated for administration to a non-human subject as a controlled release dosage form, wherein the non-human subject is selected from the group consisting of a feline, a canine and an equine. In an embodiment, the controlled release dosage form is formulated for parenteral administration. In an embodiment, the peptide has an amino acid sequence of SEQ ID NO:26. In an embodiment, the peptide has an amino acid sequence of SEQ ID NO:27. In an embodiment, the peptide has an amino acid sequence of SEQ ID NO:28. In an embodiment, the peptide has an amino acid sequence of SEQ ID NO:29.

As noted elsewhere herein, several (i.e., multiple) divided doses may be administered daily, weekly, monthly or other suitable time intervals, or the dose may be proportionally reduced as indicated by the exigencies of the situation. Where a course of multiple doses is required or otherwise desired, the compositions disclosed herein can be suitably formulated for administration via said multiple routes. For example, it may be desirable to administer a first dose parenterally (e.g., intramuscular, intravenously; subcutaneously, etc) to induce a rapid or otherwise acute analgesic effect in a subject, followed by a subsequent (e.g., second, third, fourth, fifth, etc) dose administered non-parenterally (e.g., enterally and/or topically) to provide continuing availability of the active agent over an extended period subsequent to the acute phase of treatment. Thus, in an embodiment, the peptides and compositions, as disclosed herein, are formulated for parenteral administration to the subject as a first dose (i.e., as a parenteral dosage form) and formulated for non-parenteral administration to the subject after the first dose (e.g., as an enteral and/or topical dosage form). In an embodiment, the parental administration is selected from the group consisting of intramuscular, subcutaneous and intravenous. In a further embodiment, the parental administration is subcutaneous.

In another embodiment, the enteral administration is oral administration. Thus, in an embodiment, the peptides and compositions, as disclosed herein, are formulated for parenteral administration to the subject as a first dose and formulated for oral administration to the subject after the first dose (i.e., as an oral dosage form).

In another embodiment, the enteral administration is topical administration. Thus, in an embodiment, the peptides and compositions, as disclosed herein, are formulated for parenteral administration to the subject as a first dose and formulated for topical administration to the subject after the first dose (i.e., as an oral dosage form). In an embodiment, the topical administration is transdermal administration.

In another embodiment, it may be desirable to administer a first dose parenterally (e.g., intramuscular, intravenously; subcutaneously, etc) to induce a rapid or otherwise acute analgesic effect in a subject, followed by a subsequent (e.g., second, third, fourth, fifth, etc) administration of a controlled release dosage form, as described elsewhere herein, to provide a controlled release of the active agent over an extended period subsequent to the acute phase of treatment. Thus, in another embodiment, the peptides and compositions, as disclosed herein, are formulated for parenteral administration to the subject as a first dose and formulated as a controlled release dosage form to be administered to the subject after the first dose. In an embodiment, the controlled release dosage form is formulated for parental administration.

It may also be desirable to administer a first dose enterally (e.g., orally or rectally), followed by a subsequent (e.g., second, third, fourth, fifth, etc) dose administered topically (e.g., transdermally). Thus, in an embodiment, the peptides and compositions, as disclosed herein, are formulated for enteral administration to the subject as a first dose (i.e., as an enteral dosage form; oral or rectal) and formulated for topical administration to the subject after the first dose (e.g., as a transdermal or transmucosal dosage form). In another embodiment, the peptides and compositions, as disclosed herein, are formulated for topical administration selected from the group consisting of transdermal and transmucosal administration. In a further embodiment, the peptides and compositions, as disclosed herein, are formulated for transdermal administration.

In yet another embodiment, it may be desirable to administer the peptides or compositions, as disclosed herein, enterally (e.g., orally or rectally) as a first dose, followed by a subsequent (e.g., second, third, fourth, fifth, etc) dose as a controlled release dosage form, as described elsewhere herein. Thus, in an embodiment, the peptides and compositions, as disclosed herein, are formulated for administration as a first dose enterally and formulated for administration as a controlled release dosage form, wherein the controlled release dosage form is formulated for administration subsequent to the first dose. In an embodiment, the enteral dose is formulated tor oral administration. In another embodiment, the controlled release dosage form is formulated for parenteral administration.

In an embodiment, it may be desirable to administer the peptides or compositions, as disclosed herein, topically (e.g., orally or rectally) as a first dose, followed by a subsequent (e.g., second, third, fourth, fifth, etc) dose as a controlled release dosage form, as described elsewhere herein. Thus, in an embodiment, the peptides and compositions, as disclosed herein, are formulated for topical administration as a first dose and formulated for administration as a controlled release dosage form, wherein the controlled release dosage form is formulated for administration subsequent to the first topical dose. In an embodiment, the topical dose is formulated for transdermal administration. In another embodiment, the controlled release dosage form is formulated for parenteral administration.

In a further aspect disclosed herein, there is provided a use of a peptide of formula (I), or a pharmaceutically acceptable salt thereof, as herein described, in the manufacture of a medicament for treating a condition selected from the group consisting of sarcopenia, impaired glucose tolerance, diabetes, obesity, metabolic disease and obesity-related conditions, neuropathic pain, osteoarthritis, a disorder of muscle, a wasting disorder, cachexia, anorexia, AIDS wasting syndrome, muscular dystrophy, neuromuscular disease, motor neuron disease, diseases of the neuromuscular junction, inflammatory myopathy, a burn, injury or trauma, a condition associated with elevated LDL cholesterol, a condition associated with impaired chondrocyte, proteoglycan or collagen production or quality, a condition associated with impaired cartilage tissue formation or quality, a condition that requires skin or wound repair, a condition associated with impaired muscle, ligament or tendon mass, form or function, a condition associated with inflammation, trauma or a genetic abnormality affecting muscle or connective tissue, a bone disorder, migraine and neuropathic pain.

In another aspect disclosed herein, there is provided a peptide of formula (I), or a pharmaceutically acceptable salt thereof, as herein described, for use in treating neuropathic pain in a subject, or a symptom thereof.

The invention will now be described with reference to the following Examples which illustrate some preferred aspects of the present invention. However, it is to be understood that the particularity of the following description of the invention is not to supersede the generality of the preceding description of the invention.

EXAMPLES

The peptide of SEQ ID NO:26 was synthesized by Auspep (Victoria, Australia) using solid phase synthesis and Fmoc protection strategy.

Example 1: In Vitro Electrophysiological Properties of SEQ ID NO:26

An in vitro spinal cord slice with intact dorsal root afferents combined with single-cell whole-cell patch claim electrophysiological recording techniques was used to assess the electrophysiological properties of SEQ ID NO:26 (SCRSRPVESSC; also referred to herein as LAT9993). A schematic diagram of the experimental preparation is shown in FIG. 1.

Spinal cord slices were prepared from models of neuropathic pain (Chung models; as previously described in Chung et al., *Methods Mol Med.* 2004; 99:35-45, the contents of which are incorporated herein by reference) and tested against the peptide of SEQ ID NO:26. Chung model rats, aged 8 to 12 weeks, were housed in an air-conditioned room on a 12 hour light/dark cycle with food and water available ad libitum. The rats were terminally anaesthetized using isofluorane and decapitated. The vertebral column, rib cage and surrounding tissues were rapidly removed and pinned under ice-cold (<4° C.), high sucrose-containing aCSF of the following composition (mM): sucrose 127, KCl 1.9, $KH_2PO_4$ 1.2, $CaCl_2$) 0.24, $MgCl_2$ 3.9, $NaHCO_3$ 26, D-glucose 10, ascorbic acid 0.5. A laminectomy was performed and the spinal cord and associated roots gently dissected and teased out of the spinal column and surrounding tissues. Dura and pia mater and ventral roots were subsequently removed with fine forceps and the spinal cord hemisected. Care was taken to ensure dorsal root inputs to the spinal cord are maintained. The hemisected spinal cord-dorsal root preparations were secured to a tissue sheer and spinal cord slices (400 to 450 µm thick) with dorsal roots attached were cut in chilled (<4° C.) high sucrose aCSF using a Leica VT1000s microtome. Slices were transferred to a small beaker containing ice cold aCSF containing (mM): NaCl 127, KCl 1.9, $KH_2PO_4$ 1.2, $MgCl_2$ 1.3, $CaCl_2$) 2.4, $NaHCO_3$ 26, D-glucose 10, and rapidly warmed to 35° C.±1° C. in a temperature-controlled water bath over a 20 minute period, then subsequently removed and maintained at room temperature (22° C.±2° C.) prior to electrophysiological recording. Electrophysiological recording was performed in aCSF containing (mM): NaCl 127, KCl 1.9, $KH_2PO_4$ 1.2, $MgCl_2$ 1.3, $CaCl_2$) 2.4, $NaHCO_3$ 26, D-glucose 10.

Whole-cell recordings were performed at 34-35° C. from Lamina I or II neurons in the dorsal horm of the spinal cord slices using Axopatch 1D and/or Multiclamp 700B amplifies and using the "blind" version of the patch-clamp technique. Patch pipettes were pulled from thin-walled borosilicate glass with resistances of between 3 and 8 MΩ when filled with intracellular solution. Biocytin was included in the patch solution to allow post-recording identification of the recorded neurons. The peptide of SEQ ID NO:26 was applied to the recorded tissue in the tissue bath at concentrations between 0.5 µM and 5 µM.

Figure 2:
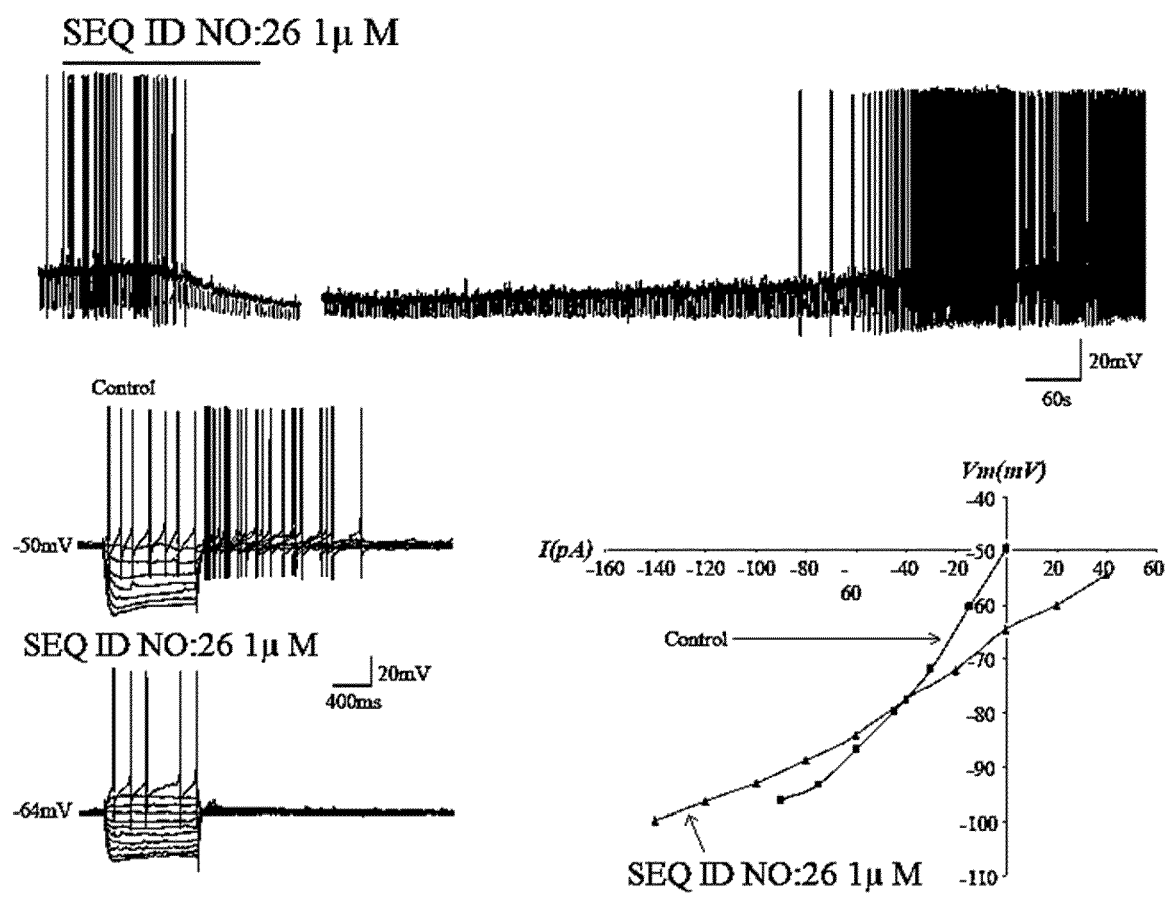
FIG. 2 provides electrophysiological plots from a single cell showing a fall in amplitude of electronic potentials induced by SEQ ID NO:26 (1 µM) and re-establishment of amplitude upon wash out of SEQ ID NO:26 (Top panel). The voltage-current relations for control and SEQ ID NO:26 (bottom left panel) are also depicted in the graph at bottom right hand panel.

The reduction in neuronal input resistance is shown in FIG. 2, by the fall in amplitude of the electronic potentials evoked in response to rectangular wave current pulses, (FIG. 2; top panel). The effect was reversible on washout of SEQ ID NO:26.

The panel on the bottom left shows voltage-current relations for both control and SEQ ID NO:26. The voltage-current relation is also shown in the graph at bottom right. The reduction in slope between the control and SEQ ID NO:26 indicates a reduction in neuronal input resistance.

Figure 3:
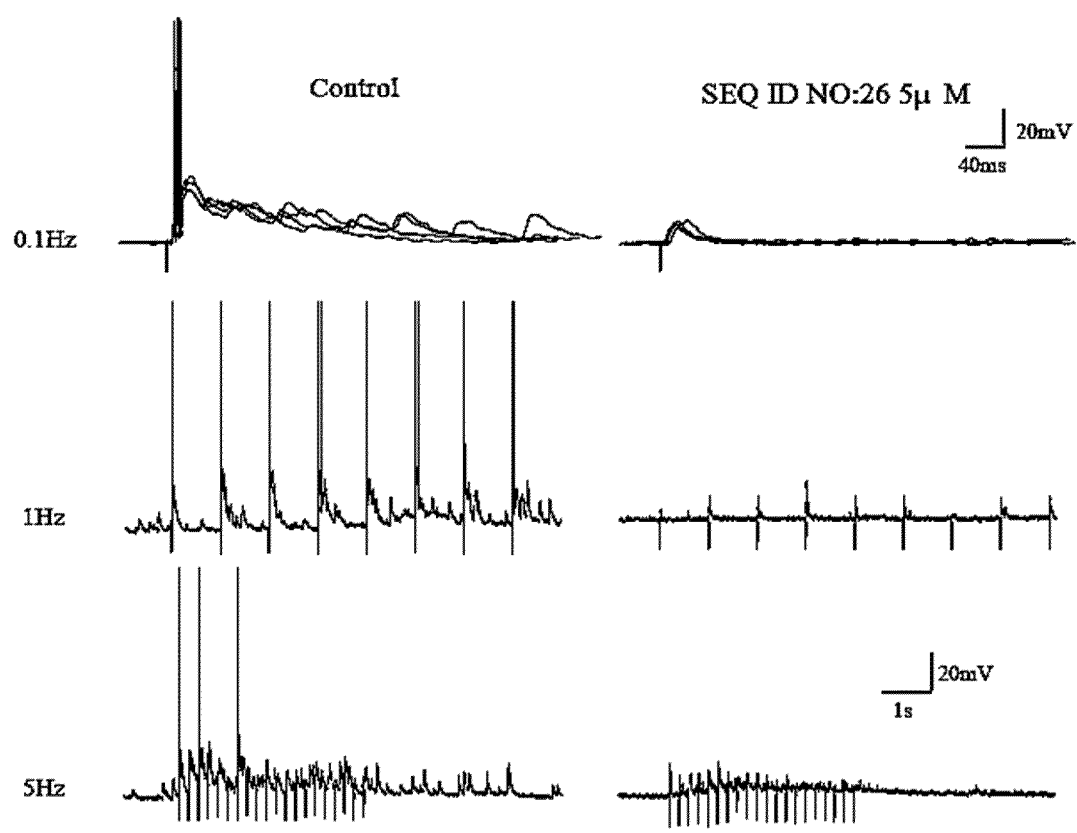
FIG. 3 shows continuous recording of excitatory postsynaptic potentials for control (left) and SEQ ID NO:26 (5 µM)

Continuous recording of excitatory postsynaptic potentials (EPSPs) is shown in FIG. 3. EPSPs were suppressed at 0.1 Hz (top), 1 Hz (middle) and Hz (bottom) in the presence of SEQ ID NO:26.

Example 2: In Vivo Properties of SEQ ID NO:26

Figure 4:
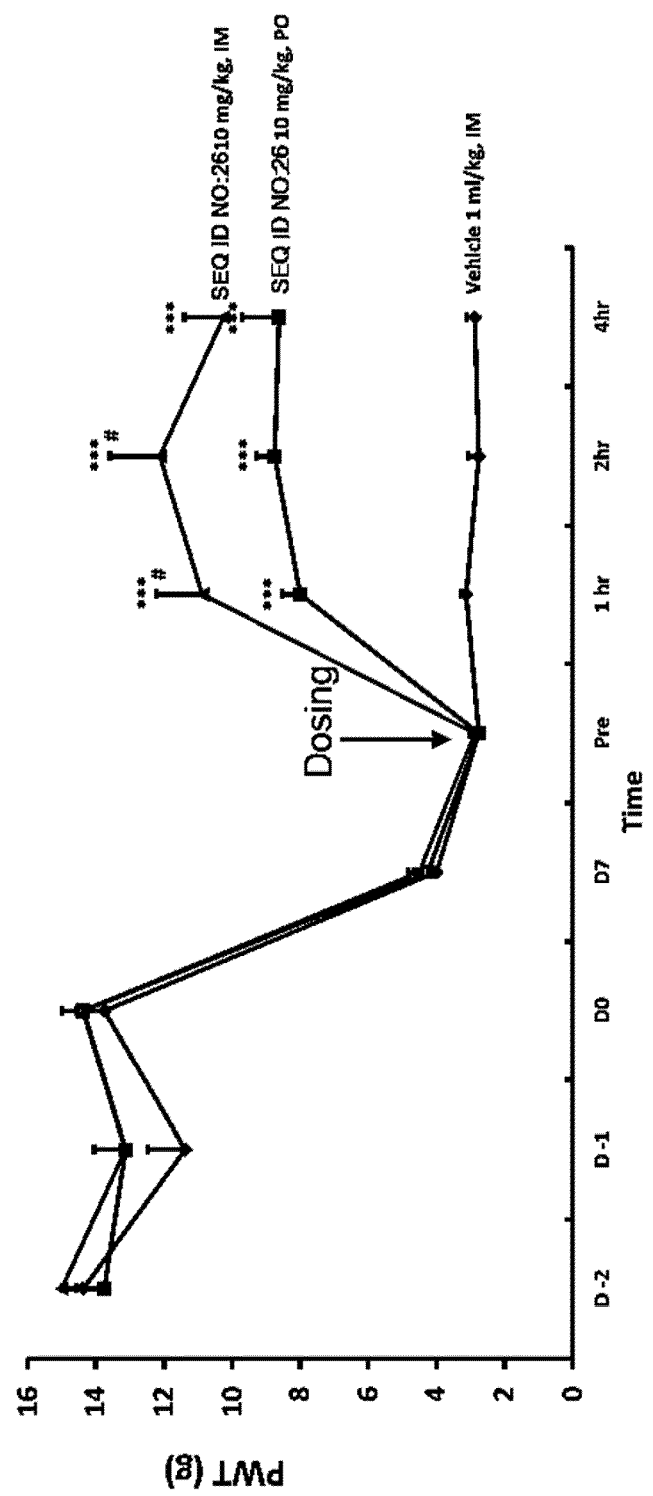
FIG. 4 shows the effect of SEQ ID NO:26 on the paw withdrawal threshold (PWT) of the ipsilateral paws in Chung model rats (Chung et al., *Methods Mol. Med.* 2004; 99:35-45). The peptide of SEQ ID NO:26 was administered at 10 mg/kg either orally (PQ) or by intramuscular (IM) injection to Chung model rats and pain was assessed by paw withdrawal. Pre-dosing control; Vehicle: 5% DMSO in PBS. *** $p<0.001$, compared to the same time points in the Vehicle control group; # $p<0.05$, compared to SEQ ID NO:26 PO group at the same time point. n=8 for each group.

An in vitro Chung model of chronic nerve constriction in rats (Chung et al., *Methods Mol. Med.* 2004; 99:35-45) was used to assess the effect of SEQ ID NO:26 on neuropathic pain. SEQ ID NO:26 was administered at 10 mg/kg either orally or by intramuscular injection to Chung model rats and pain was assessed by paw withdrawal. As shown in FIG. 4, SEQ ID NO:26 significantly reduced pain as measured by the increase in paw withdrawal threshold at 1, 2 and 4 hours post-dosing.

Example 3: Effect of LAT9993 Loop (SEQ ID NO:27) and LAT9993 LoopS (SEQ ID NO:28; Also Referred to Herein as LAT9993S) on Dorsal Horn Neurons and Dorsal Root Afferent-Mediated Synaptic Transmission in a Rat Model of Neuropathic Pain Materials and Methods Spinal nerve ligation (Chung model; as described in Examples 1 and 2, above) was performed by a single tight ligation on the L5 spinal nerve. This model shows typical neuropathic pain symptoms/signs, such as mechanical allodynia, mechanical and thermal hyperalgesia and spontaneous pain mimicking the symptoms observed in human patients. This animal model is often used as the "gold standard" for neuropathic pain.

A. Animals

Adult male Sprague-Dawley rats, weighing 220-250 g (aged 7 weeks and older) at the time of surgery, were used in this study. They were housed in groups of 4, in an air-conditioned room, on a 12-hour light/dark cycle with food and water available ad libitum. All experiments were performed in accordance with the U. K. Animals (Scientific Procedures) Act (1986).

The animals were housed in groups of 4 in an air-conditioned room on a 12-hour light/dark cycle. Food and water were available ad libitum. Animals were allowed to acclimatise to the environment for experiments for three days by leaving them on a raised metal mesh for at least 40 min. The baseline paw withdrawal threshold (PWT) was examined using a series of graduated von Frey hairs (see below) for 3 consecutive days before surgery and re-assessed on the $6^{th}$ to $8^{th}$ day after surgery and on the $12^{th}$ to $14^{th}$ day-after surgery before drag dosing.

Each rat was anaesthetized with 5% isoflurane mixed with oxygen (2 L per min) followed by an intramuscular (i.m.) injection of ketamine 90 mg/kg plus xylazine 10 mg/kg. The back was shaved and sterilized with povidone-iodine. The animal was placed in a prone position and a para-medial incision was made on the skin covering the L4-6 level. The L5 spinal nerve was carefully isolated and tightly ligated with 6/0 silk suture. The wound was then closed in layers after a complete haemostasis. A single dose of antibiotics (Amoxipen, 15 mg/rat, i.p.) was routinely given for prevention of infection after surgery. The animals were placed in a temperature-controlled recovery chamber until fully awake before being returned to their home cages.

B. Formulation and Administration of Test Compounds

The peptides of SEQ ID NO:27 (also referred to herein as LAT9993 Loop) and SEQ ID NO:28 (also referred to herein as LAT9993S or LAT9993 LoopS), were solubilised in distilled water and made up as concentrated stocks and stored frozen until the day of experiment when they were diluted to the required test concentrations in artificial cerebrospinal fluid (aCSF). The aCSF comprised (mM): NaCl, 127; KCl, 1.9; $KH_2PO_4$, 1.2; $CaCl_2$, 2.4; $MgCl_2$, 1.3; $NaHCO_3$, 26; D-glucose, 10; equilibrated with 95% $O_2$-5% $CO_2$.

C. Study Procedures

Figure 5:
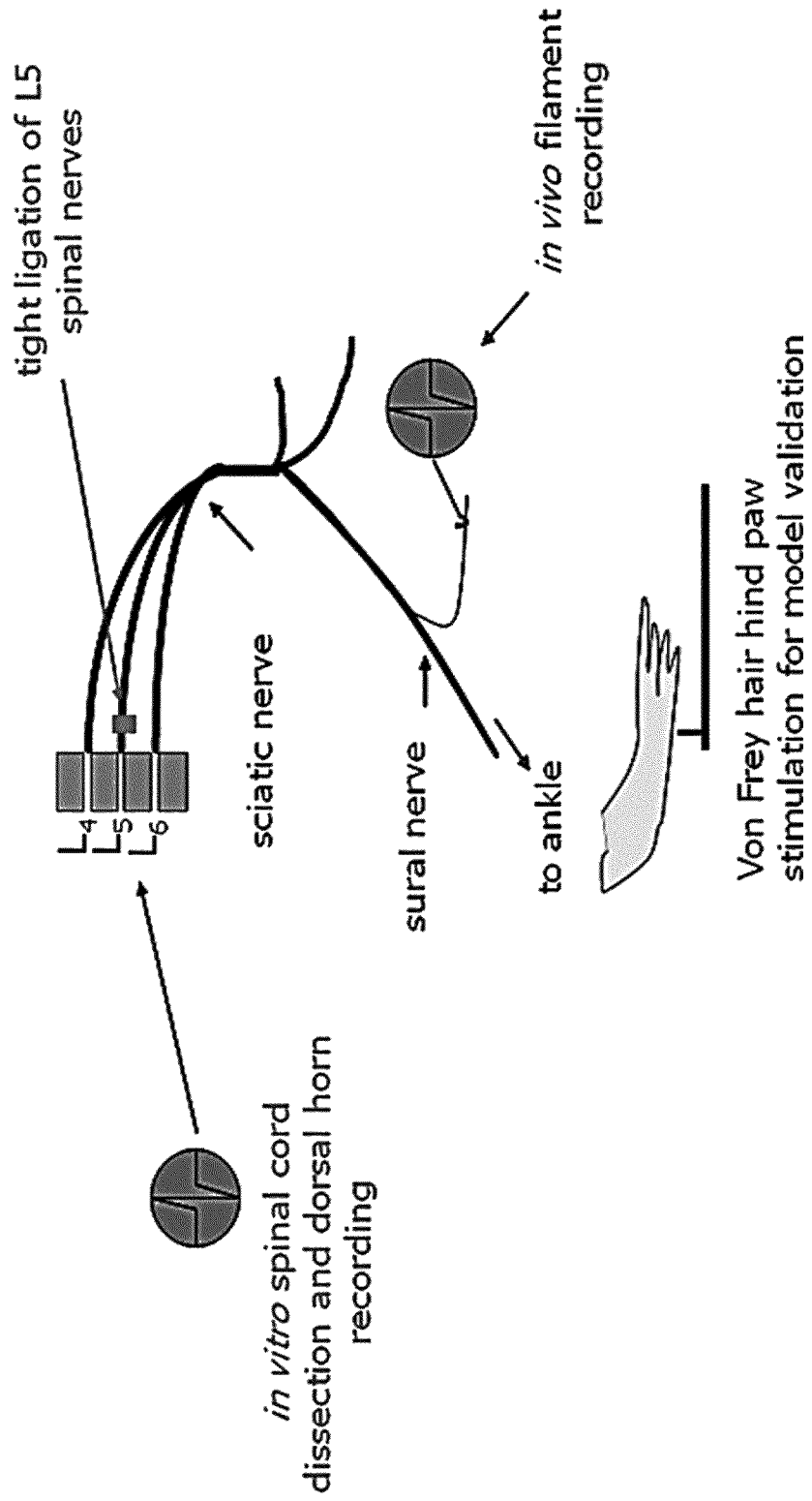
FIG. 5: Outline schematic of the methodology for preparation of Chung models of neuropathic pain.

Ten to fourteen days after surgery, animals were placed in individual Perspex boxes on a raised metal mesh for at least 40 minutes prior to PWT testing. Starting with the filament of lowest force (1 g), each filament was applied perpendicularly to the centre of the ventral surface of the paw until slightly bent for 6 seconds. If the animal withdrew or lifted its paw upon stimulation, a von Frey hair with force immediately lower than that tested was subsequently used. If no response was observed, then a hair with force immediately higher was tested. The lowest amount of force required to induce reliable responses (positive in 2 out of 3 trials) was recorded as the value of PWT. Only animals showing significant mechanical allodynia (PWT≤3.5 g) were selected for subsequent electrophysiological experiments (see FIG. 5).

D. Spinal Cord Slice Preparation

Once validation of a neuropathic state had been confirmed, animals were terminally anesthetized using isoflurane (Norvartis Animal Health UK Ltd.), cervically dislocated and decapitated. A laminectomy was performed and the spinal cord, with spinal roots and DRG attached, removed and cut into 250-450 μm thick slices using a Leica VT1000S vibrating microtome (Leica Microsystems UK, Milton Keynes, United Kingdom). Slices were maintained in artificial cerebrospinal fluid (aCSF) at room temperature for 1 hr after slicing before recording. For recording, individual slices were held between two grids in a custom-built chamber continuously perfused with aCSF at a rate of 4-10 $ml.min^{-1}$, illuminated from below, and viewed under a dissection microscope.

E. Electrophysiological Recording

Whole cell recordings were performed at 35±1° C. from neurons in the dorsal horn of spinal cord slices using a Multiclamp 700B amplifier, and the 'blind' version of the patch-clamp technique. Patch pipettes were pulled from thin-walled borosilicate glass with resistances of between 3 and 8 MΩ when filled with intracellular solution of the following composition (mM): potassium gluconate, 140, KCl, 10, EGTA-Na, 1, HEPES, 10, $Na_2ATP$, 4, Na-GTP, 0.3.

Figure 6:
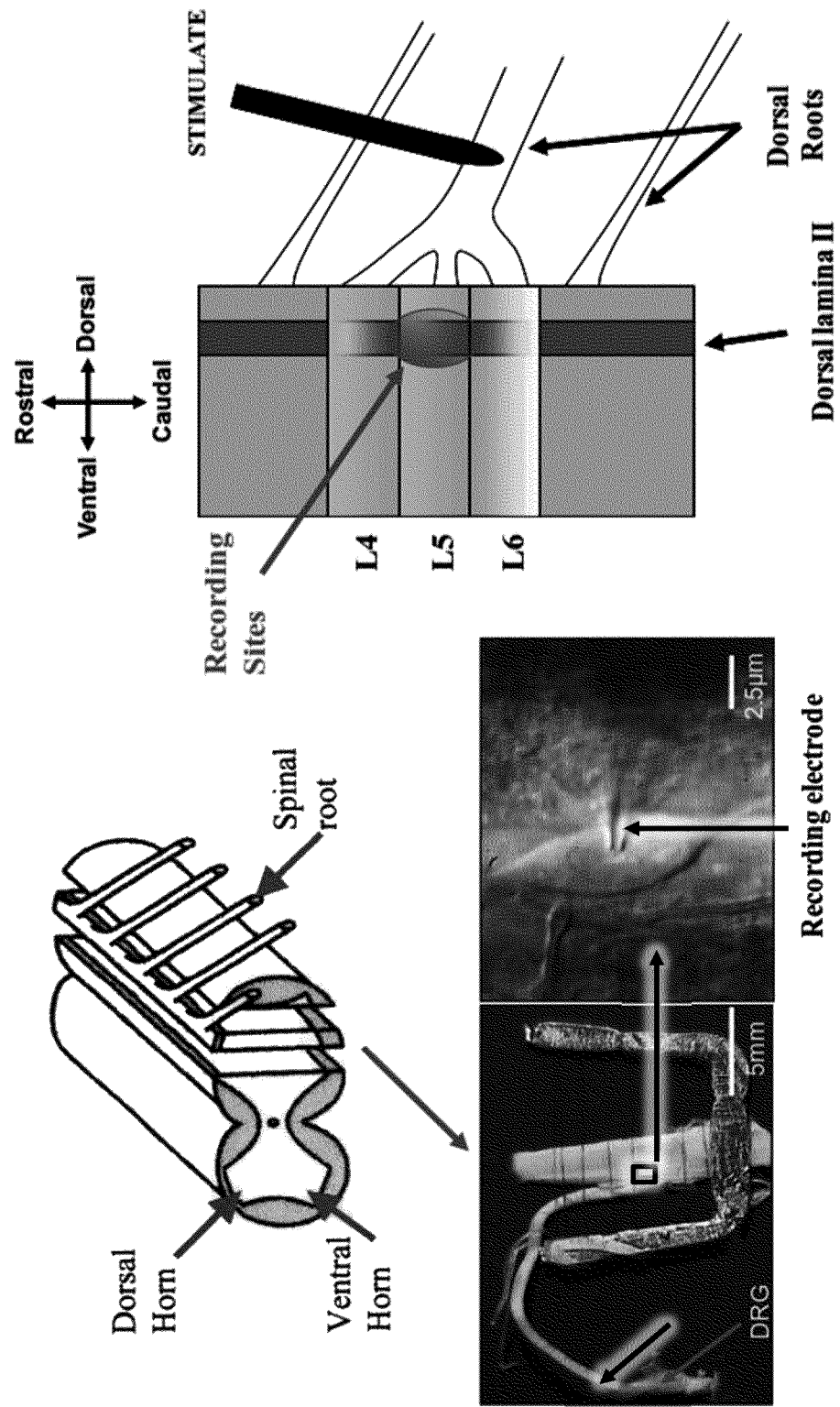
FIG. 6: Schematic diagrams and photographs outlining spinal cord slice preparation and whole-cell recording set up.

Recordings were monitored on an oscilloscope and stored on digital audio tapes for later off-line analysis. In addition, data were low-pass filtered at 2-5 kHz, (1 kHz for voltage-clamp data), digitized at 2-10 kHz and stored on a PC running pCLAMP 10 data acquisition software (Axon Instruments). Analysis of electrophysiological data was earned out using Clampfit 10 software. See FIG. 6.

F. Statistical Methods

Statistical analysis was performed using Student's paired t-test where appropriate, with probability values of less than 0.05 considered to indicate statistical significance, unless otherwise stated.

Results

Rats recovered well after surgery. Body weight gained 30-50 grams the first week after surgery, and 50-70 grams over the second week. Animals showed some degree of disuse of the affected paws or limping. However, the general appearance of the animals was not remarkably different from their naïve counterparts.

The principal aim of this aspect of the study was to investigate the effects of SEQ ID NO:27 (LAT9993 Loop) and SEQ ID NO:28 (LAT9993 LoopS) on spinal cord dorsal horn neurons.

A. The Effects of LAT9993 Loop on Dorsal Horn Neurons

The effects of LAT9993 Loop (5 μM) were investigated on 6 dorsal horn neurons in spinal cord slices prepared from Chung models of neuropathic pain, recorded ipsilateral to the site of injury. In these neurons, LAT9993 induced a marked membrane hyperpolarisation and inhibition of activity in 4 neurons, ranging between 2 and 7 mV, and had little effect on a further 2 dorsal horn neurons.

Figure 7:
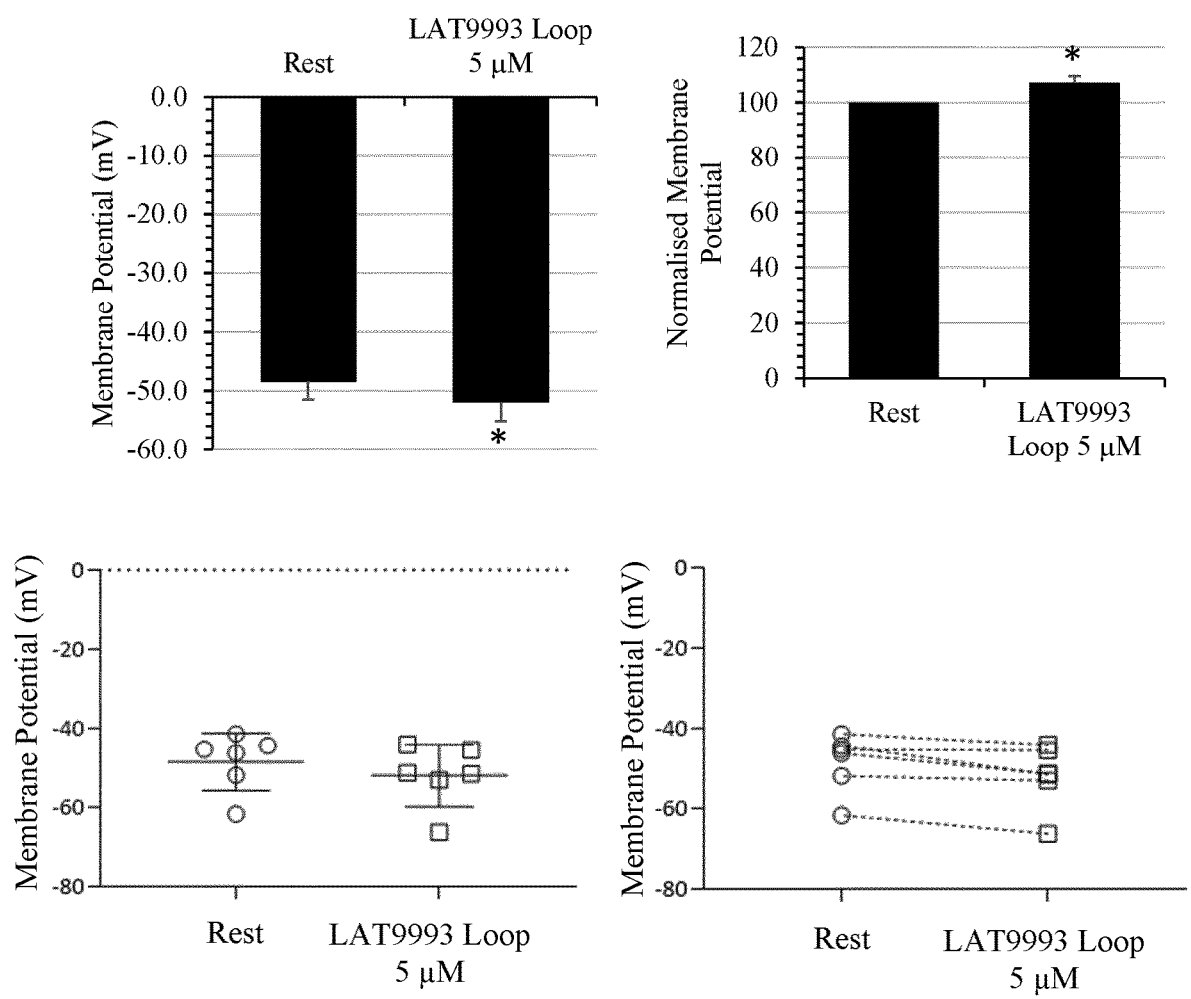
FIG. 7. Summary data showing changes in membrane potential associated with LAT9993 Loop-induced responses in dorsal horn neurons from Chung models of neuropathic pain. (n=6, * $P<0.05$ vs rest, Student's paired t-test).
Figure 8:
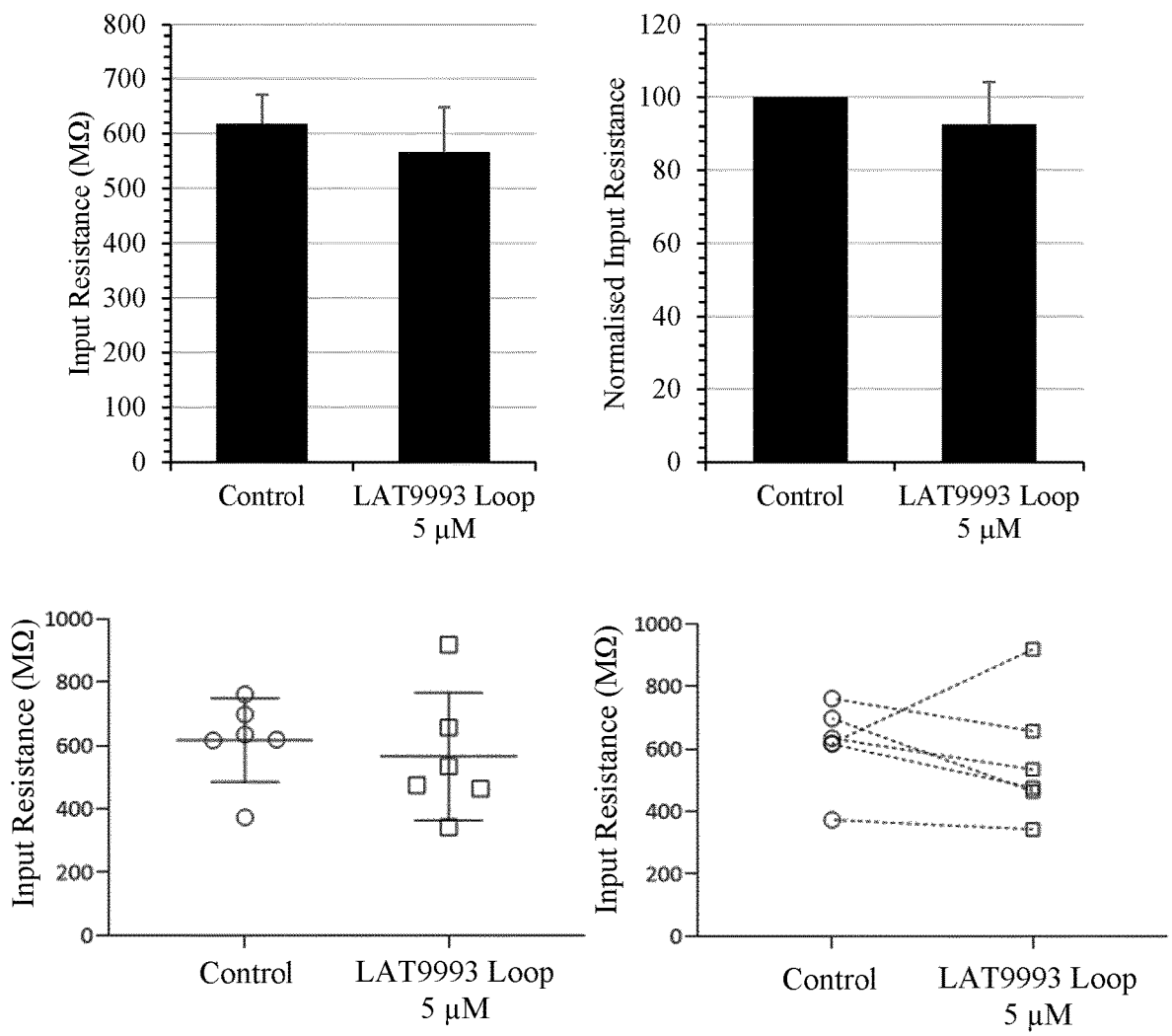
FIG. 8. Summary data showing changes in neuronal input resistance associated with LAT9993 Loop-induced responses in dorsal horn neurons from Chung models of neuropathic pain, (n=6).
Figure 9:
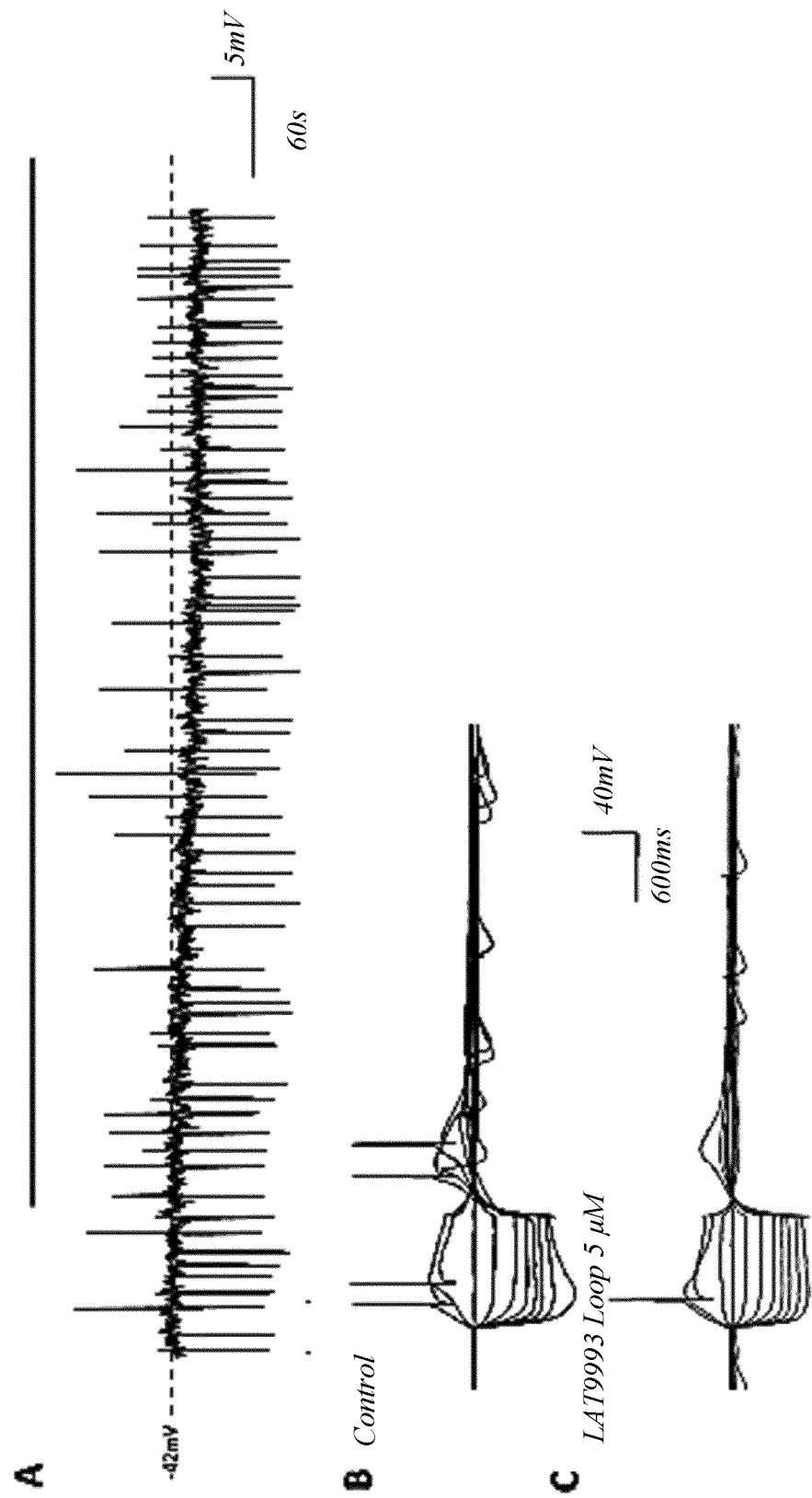
FIG. 9. A: LAT9993 Loop-induced hyperpolarisation associated with a reduction in neuronal input resistance B: Voltage-current (VI) relations of the same cell as shown in A. Voltage responses to current injection are shown superimposed. C show's a plot of the data from the same cell as B in the presence of LAT9993 Loop. D show's a plot of the VI relations of the same cell as shown in B and C. Note the reduction in the slope indicating a reduction in neuronal input resistance indicating ion channel opening. The plots intersect around −60 mV (approaching the reversal potential for chloride ions under our recording conditions). Note also the decrease in slope of the plot at more negative membrane potentials in LAT9993 Loop indicating enhanced inward rectification in the presence of the compound, FIG. 10. A and B: VI relations showing LAT9993 Loop induced hyperpolarisation, associated with enhanced activation of inward rectification, C and D: Plot of the VI relations of the same cell as shown in A and B (peak response and steady-state). Note the reduction in the slope indicating a reduction in neuronal input resistance indicating ion channel opening. The plots intersect around −55 mV (approaching the reversal potential for chloride ions under our recording conditions). Note also the enhanced inward rectification at negative membrane potentials (reduced slope in the plots beyond membrane potentials more negative than −80 mV.
Figure 9:
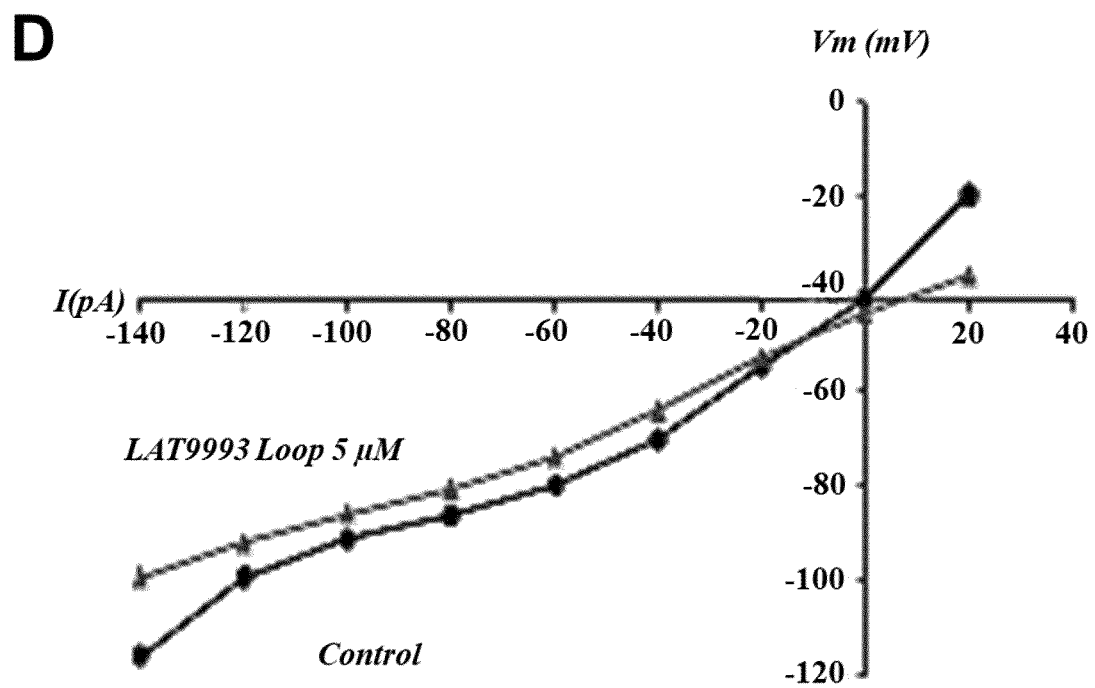
Figure 10:
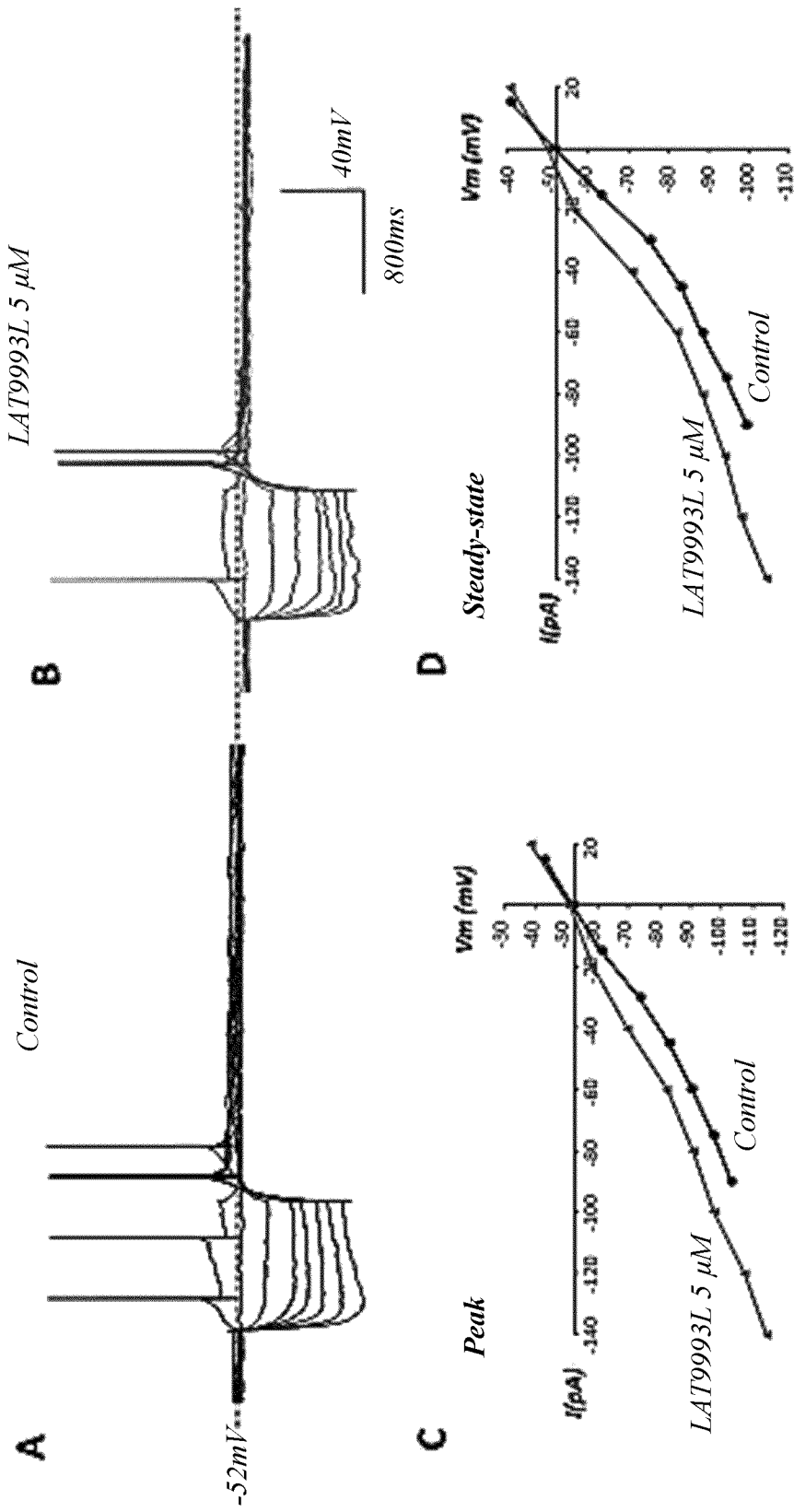
Figure 11:
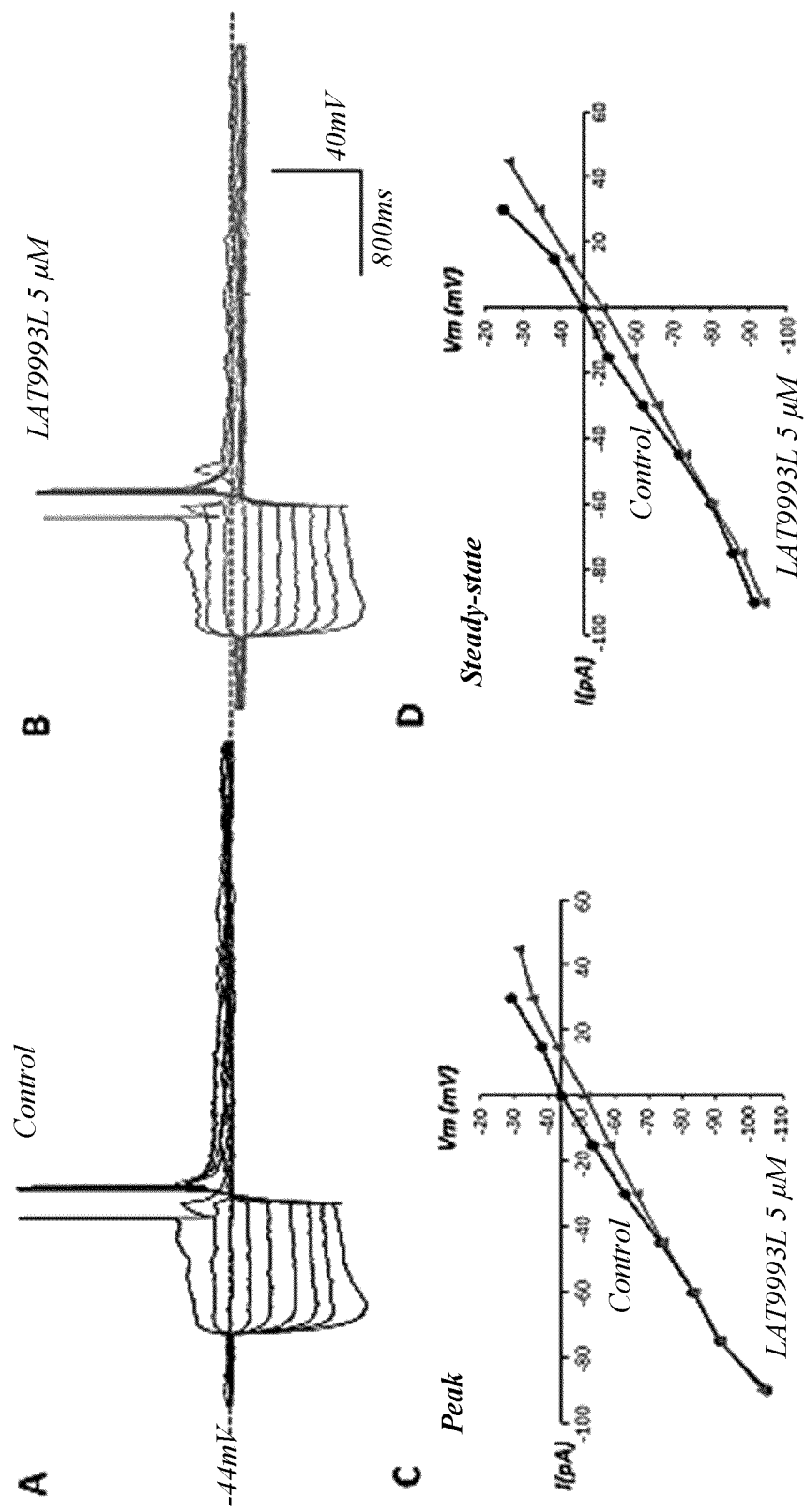
FIG. 11. LAT9993 Loop-induced hyperpolarisation mediated via activation of a potassium conductance. A and B: VI relations of the same cell in the absence (A) and presence (B) of LAT9993 Loop, C and D shows a plot of the data shown in A and B (peak response and steady-state). Note the reduction in the slope indicating a reduction in neuronal input resistance consistent with ion channel opening. The plots intersect around −80 mV (approaching the reversal potential for potassium ions), FIG. 12. A: LAT9993 Loop-induced a suppression of dorsal root afferent-mediated EPSPs. A: Samples of a continuous record showing the effects of LAT9993 Loop on membrane potential. B and C show superimposed dorsal root afferent-stimulated synaptic responses in the same cell. Note the mix of EPSPs (upward deflections) and IPSPs (downward deflections) evoked by electrical stimulation of dorsal root afferents in control (B) but the lack of EPSPs in the presence of LAT9993 Loop (C), suggesting this compound suppressed dorsal root afferent mediated excitatory synaptic transmission.

Data for all cells (n=6) showed LAT9993 Loop induced membrane hyperpolarisation from a mean resting membrane potential of −48.5±3 mV to a new steady-state resting potential of −51.9±3.9 mV, amounting to a 3.5±1.1 mV change in membrane potential (n=6, P<0.05, Table 2). LAT9993 Loop-induced responses were associated overall with a reduction in neuronal input resistance, indicated by the fall in amplitude of electrotonic potentials evoked in response to constant amplitude rectangular-wave current pulses (0.1 Hz; 10-600 pA; 0.5 to 1 s duration) and from the reduction in slope of plots of VI relations. Neuronal input resistance was reduced from a mean control resting level of 617.9±53.8 MΩ to 566.3±82.0 MΩ (n=6, P=0.523) in the presence of LAT9993 Loop, amounting to a 51.6±75.3 MΩ reduction in neuronal input resistance. FIG. 7A summarises the effects of LAT9993 Loop on membrane properties of dorsal horn neurons (see also Table 2).

As LAT9993 Loop induced a range of effects within a small sample size, we closer inspected those cells where clear responses were observed. In four neurons, LAT9993 loop induced a clear membrane hyperpolarisation and inhibition of spontaneous activity, an effect that was partly reversible in one cell but persisted in others (see FIGS. 8, 9, 10 and 11). The reversal potential associated with LAT9993 loop-induced responses was also variable: in one cell the reversal potential was around −55 mV whereas in another it amounted to around −85 mV, close to the reversal potentials for chloride and potassium ions, respectively.

Figure 12:
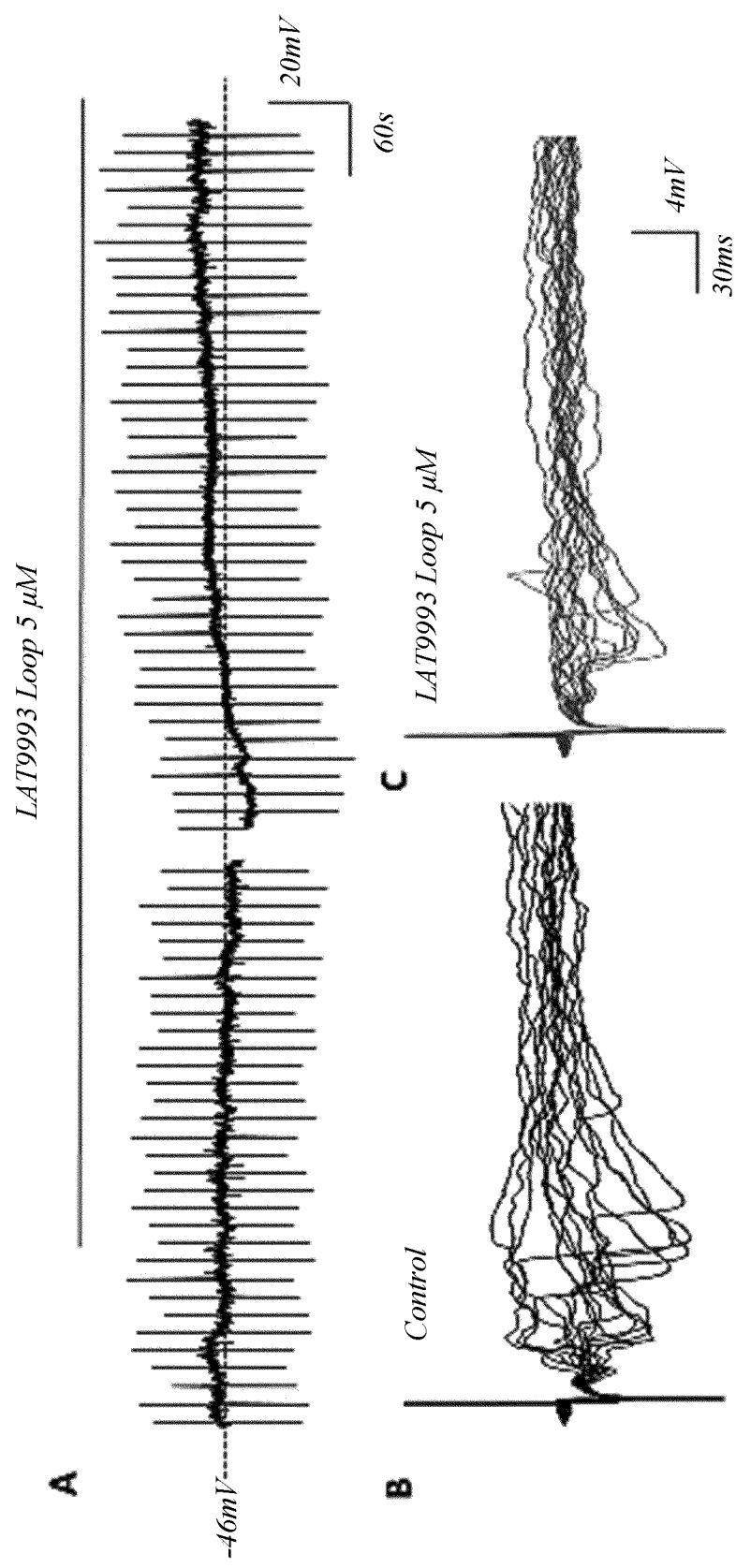

Wherever possible, the effects of LAT9993 Loop were tested on dorsal root afferent-mediated synaptic inputs. LAT9993 Loop suppressed dorsal root-evoked excitatory posts-synaptic potentials (EPSPs) with little effect on evoked inhibitory post-synaptic potentials (FIG. 12).

TABLE 2

Summary data of changes in membrane potential and input resistance associated with LAT9993 Loop-induced responses in dorsal horn neurons from Chung models of neuropathic pain.

|  | Rest | LAT9993 Loop 5 µM | ΔVm |
|---|---|---|---|
| Membrane Potential (mV) | | | |
| Mean | −48.5 | −51.9 | 3.5 |
| SEM | 3.0 | 3.2 | 1.1 |
| n | 6 | 6 | 6 |
| P | | 0.022 | |
| Normalised Membrane Potential | | | |
| Mean | 100 | 107.2 | −7.2 |
| SEM | | 2.3 | 2.3 |
| n | 6 | 6 | 6 |
| P | | 0.026 | |
|  | Control | LAT9993 Loop 5 µM | ΔIR |
| Input Resistance (MΩ) | | | |
| Mean | 617.9 | 566.3 | 51.6 |
| SEM | 53.8 | 82.0 | 75.3 |
| n | 6 | 6 | 6 |
| P | | 0.523 | |
| Normalised Input Resistance | | | |
| Mean | 100 | 92.4 | 7.6 |
| SEM | | 11.7 | 11.7 |
| n | 6 | 6 | 6 |
| P | | 0.547 | |

B. The Effects of LAT9993 LoopS on Dorsal Horn Neurons

The effects of LAT9993 LoopS (SEQ ID NO:28; 5 µM) were investigated on 5 dorsal horn neurons in spinal cord slices prepared from Chung models of neuropathic pain, recorded ipsilateral to the site of injury. In these neurons, LAT9993 LoopS induced a membrane hyperpolarisation and inhibition of activity in 3 neurons and had little effect on a further 2 dorsal horn neurons.

Figure 13:
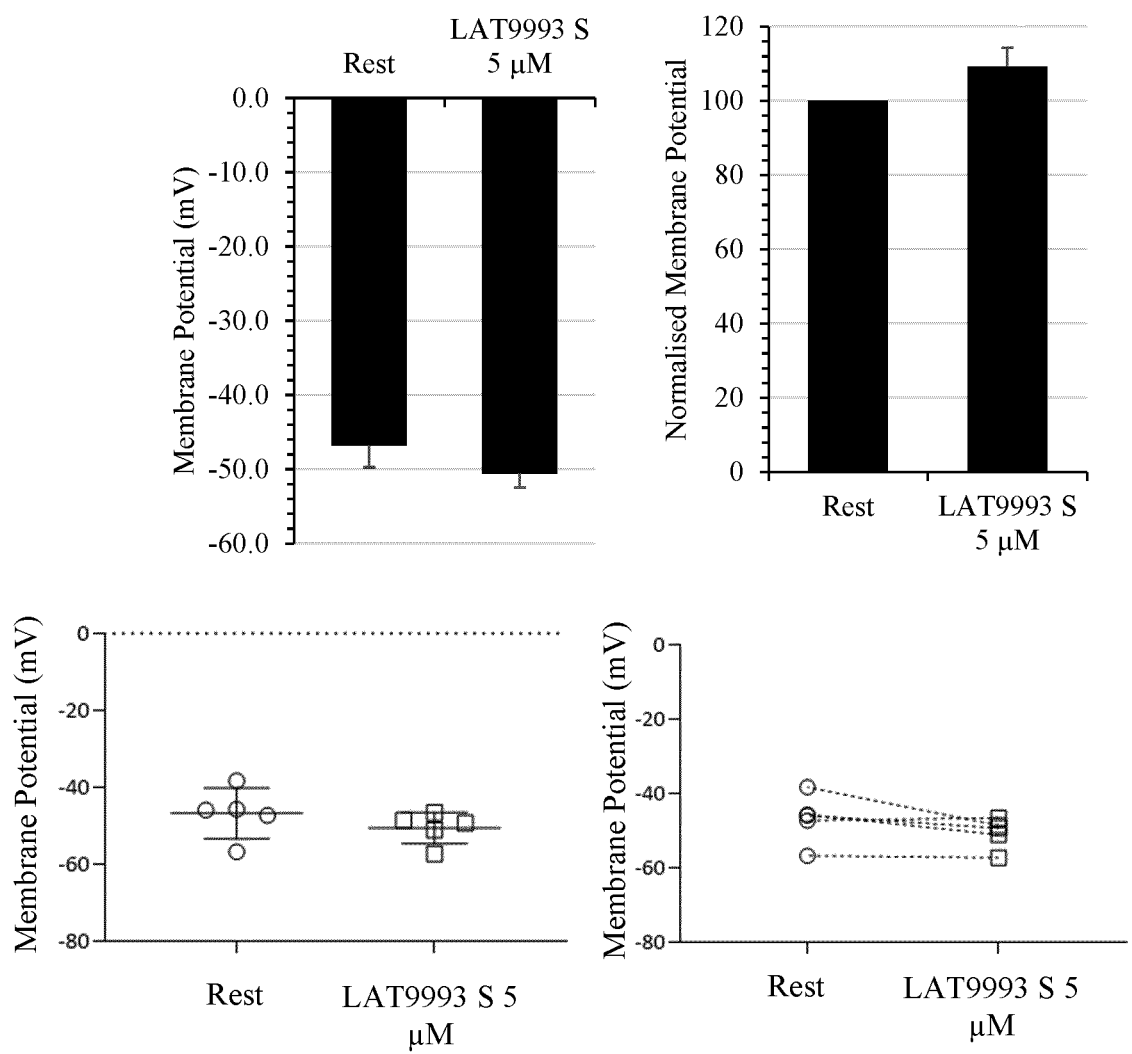
FIG. 13. Summary data showing changes in membrane potential associated with LAT9993S-induced responses in dorsal horn neurons from Chung models of neuropathic pain (n=5).
Figure 14:
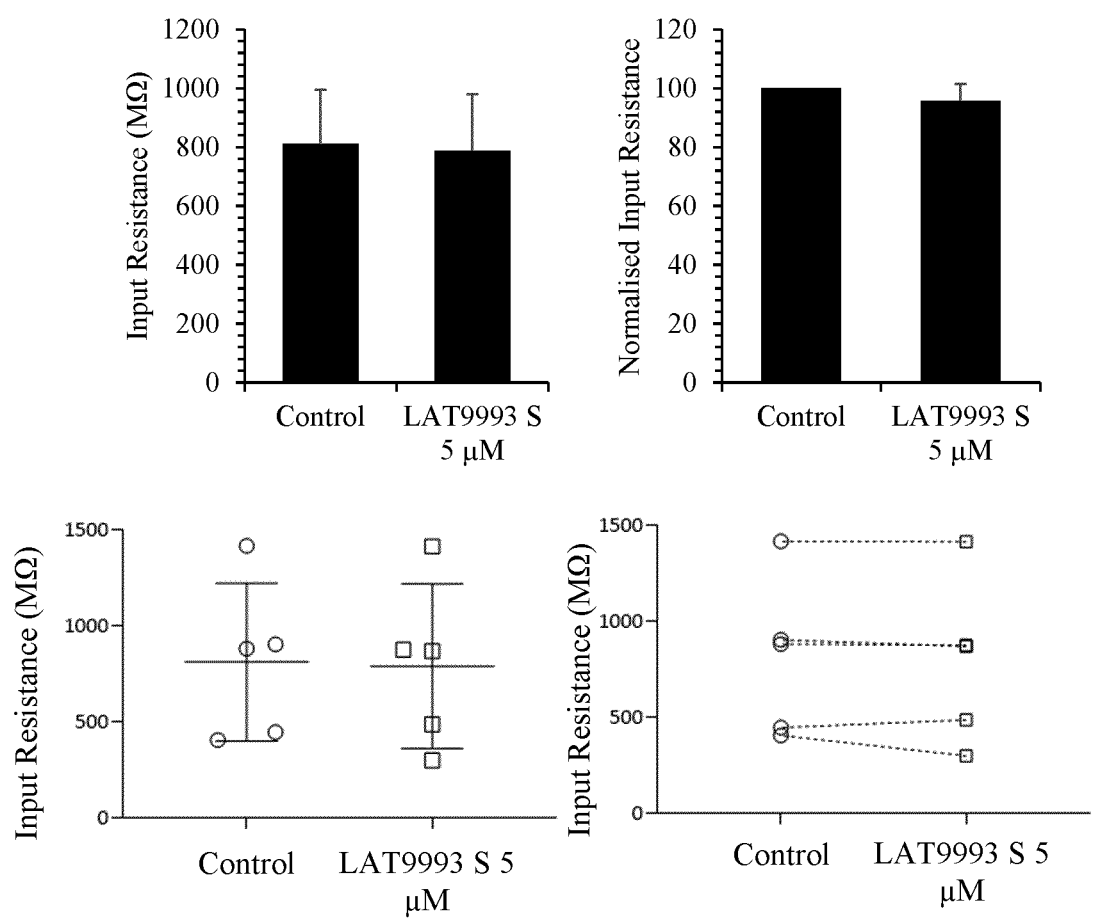
FIG. 14. Summary data showing changes in neuronal input resistance associated with LAT9993S-induced responses in dorsal horn neurons from Chung models of neuropathic pain (n=5).

Data for all cells (n=5) showed LAT9993 LoopS induced membrane hyperpolarisation from a mean resting membrane potential of −46.8±3 mV to a new steady-state resting potential of −50.6±1.8 mV, amounting to a 3.8±2 mV change in membrane potential (n=5, ns, P=0.124, Table 3). LAT9993 LoopS-induced responses were associated overall with a reduction in neuronal input resistance, indicated by the fall in amplitude of electrotonic potentials evoked in response to constant amplitude rectangular-wave current pulses (0.1 Hz; 10-600 pA; 0.5 to 1 s duration) and from the reduction in slope of plots of VI relations. Neuronal input resistance was reduced from a mean control resting level of 810±184.2 MΩ to 788±191.9 MΩ (n=5, ns, P=0413) in the presence of LAT9993 LoopS, amounting to a 22.1±24.2 MΩ reduction in neuronal input resistance. FIGS. 13 and 14 summarise the effects of LAT9993 LoopS on membrane properties of dorsal horn neurons (see also Table 3).

Figure 15:
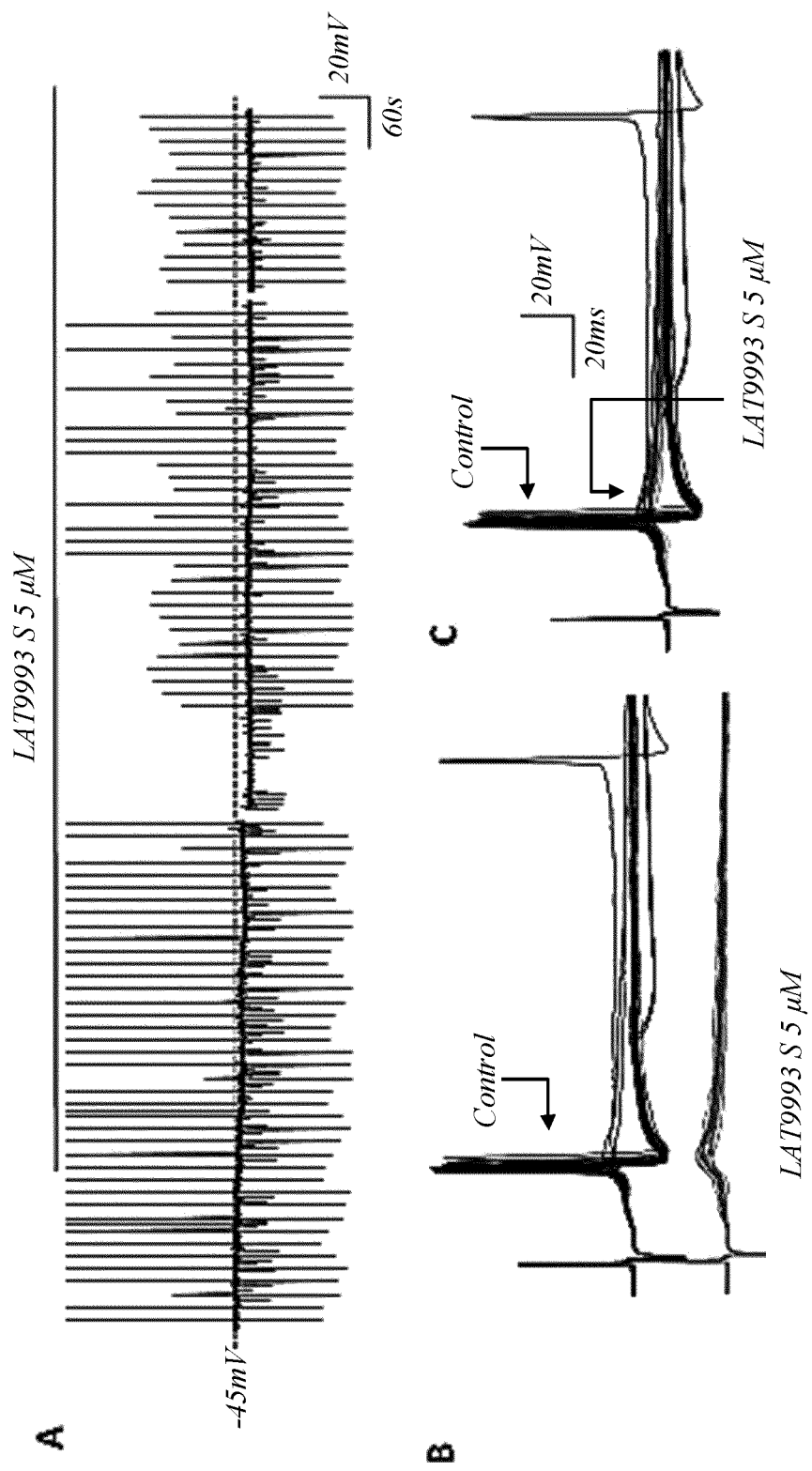
FIG. 15. A: LAT9993S-induced membrane hyperpolarisation and a suppression of dorsal root afferent-mediated EPSPs. A. Samples of a continuous record showing the effects of LAT9993S on membrane potential. K and C show superimposed dorsal root afferent-stimulated synaptic responses in the same cell. Note the suppression of EPSPs evoked by electrical stimulation of dorsal root afferents in the presence of LAT9993S (shown superimposed in C), suggesting this compound suppressed dorsal root afferent mediated excitatory synaptic transmission.
Figure 16:
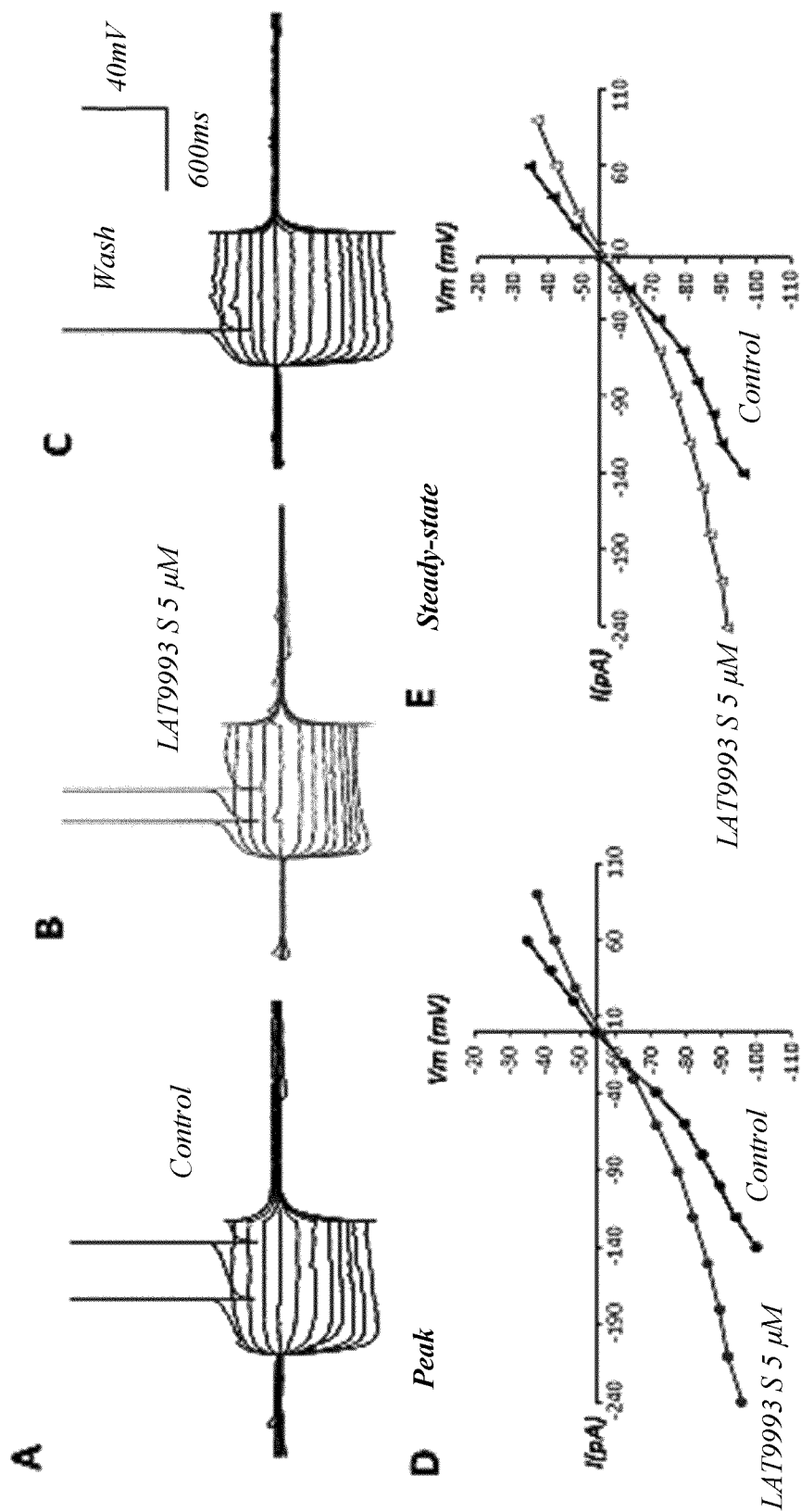
FIG. 16. LAT9993S-induced hyperpolarisation mediated via activation of a chloride conductance and enhanced inward rectification. A, B and C: VI relations of the same cell in the absence (A) and presence (B) of LAT9993S and subsequently after washout of the compound (C). D and E show a plot of the data in A and B (peak response and steady-state). Note the reduction in the slope indicating a reduction in neuronal input resistance consistent with ion channel opening. The plots intersect around −65 mV (approaching the reversal potential for chloride ions) and the reduced slope at negative membrane potentials suggesting increased activation of inward rectification (see also IV in B).
Figure 17:
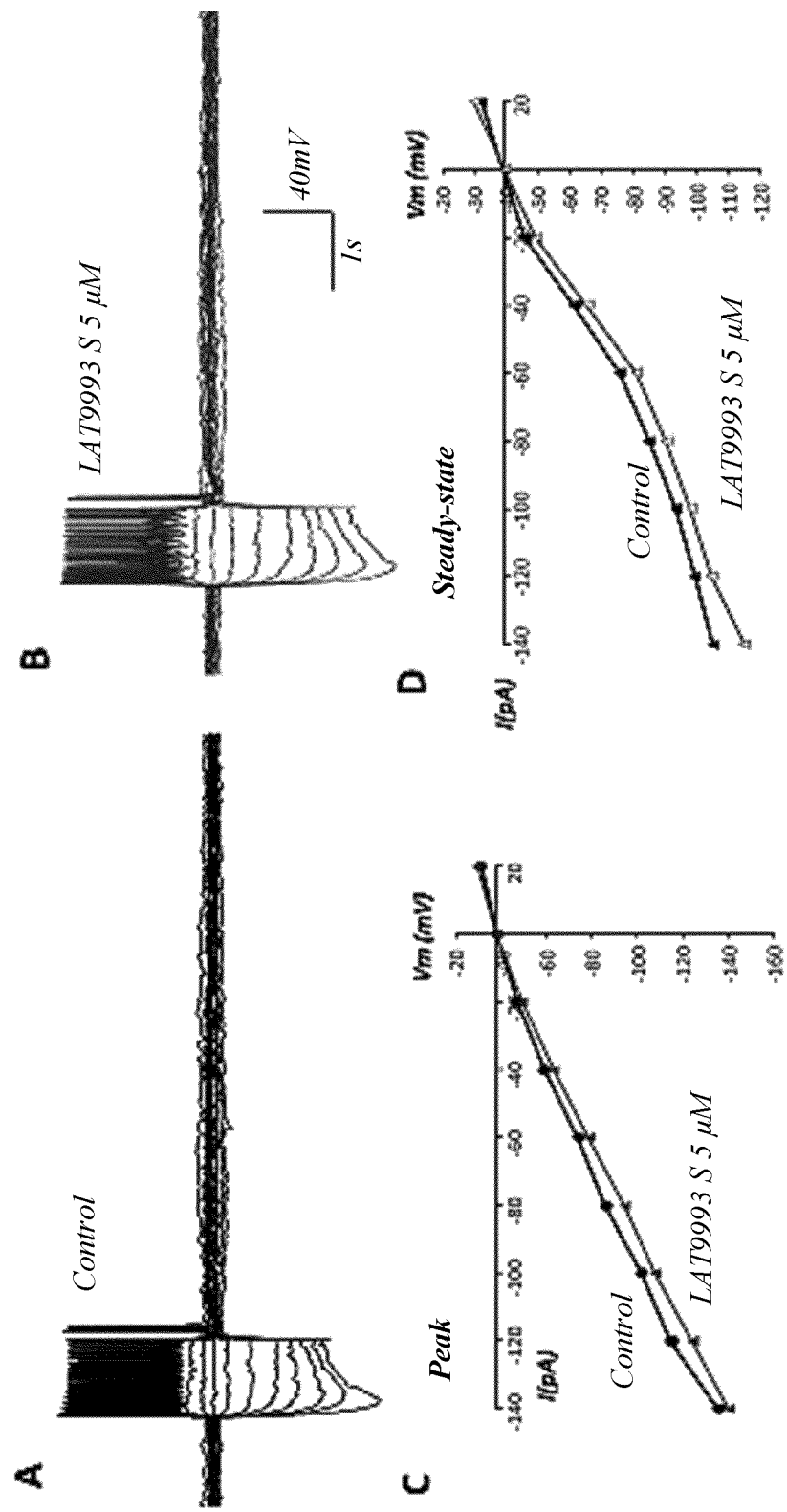
FIG. 17. LAT9993S induced hyperpolarisation mediated via activation of a chloride conductance. A and B: VI relations of the same cell in the absence (A) and presence (B) of LAT9993S. C and 1) show a plot of the data shown in A and B (peak response and steady-state). Note the reduction in the slope indicating a reduction in neuronal input resistance consistent with ion channel opening. Both plots intersect around −55 mV (approaching the reversal potential for chloride ions).

As LAT9993S induced a range of effects within a small sample size, we closer inspected those cells where clear responses were observed. In three neurons, LAT9993 LoopS induced a clear membrane hyperpolarisation and inhibition of spontaneous activity (see FIGS. 13, 14 and 15). The reversal potential associated with LAT9993 Loop-induced responses was also variable: in one cell the reversal potential was around −55 mV. In two other cells, a clear enhancement in inward rectification was also apparent indicated by the decrease in slope of VI plots at negative membrane potentials (beyond around −75 mV); See FIGS. 16 and 17.

Figure 18:
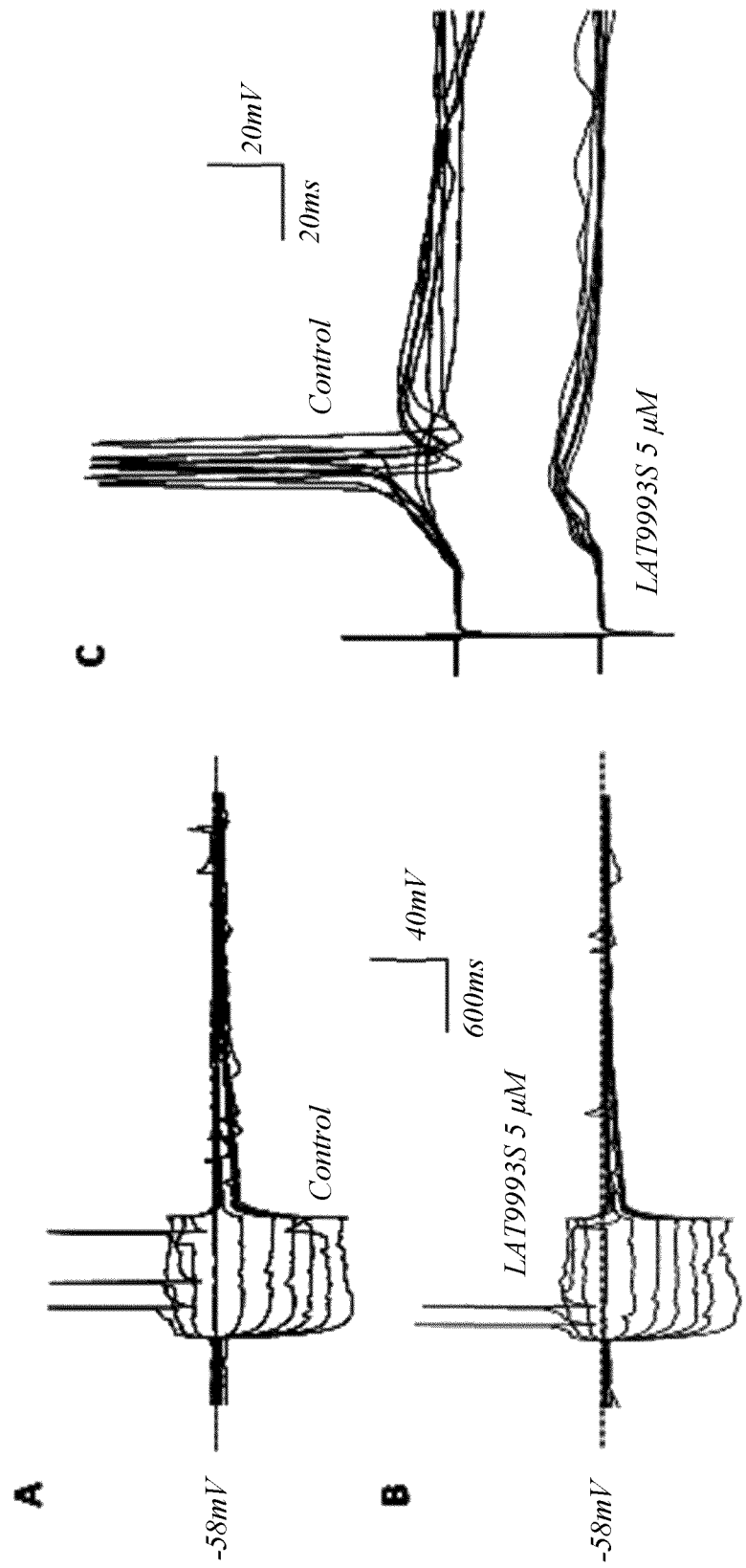
FIG. 18. A: LAT9993S selectively suppressed dorsal root afferent-mediated EPSPs. A and B. Samples of a continuous record showing the effects of LAT9993S on VI relations. Note the lack of effect of LAT9993S on postsynaptic membrane properties in this cell. C shows superimposed dorsal root afferent-stimulated synaptic responses in the same cell. Note the suppression of EPSPs evoked by electrical stimulation of dorsal root afferents in the presence of LAT9993S, suggesting this compound suppressed dorsal root afferent mediated excitatory synaptic transmission selectively without effects on the membrane properties of the cell FIG. 19. Summary data showing changes in membrane potential and neuronal input resistance associated with LAT9993 Loop S-induced responses in dorsal horn neurons from Chung models of neuropathic pain, (n=3).

Wherever possible, the effects of LAT9993 Loops were tested on dorsal root afferent-mediated synaptic inputs. LAT999 LoopS suppressed dorsal root-evoked excitatory posts-synaptic potentials (EPSPs) in two neurons (see FIGS. 15 and 18).

TABLE 3

Summary data of changes in membrane potential and input resistance associated with LAT9993 LoopS -induced responses in dorsal horn neurons from Chung models of neuropathic pain.

|  | Rest | LAT9993 LoopS 5 µM | ΔVm |
|---|---|---|---|
| Membrane Potential (mV) | | | |
| Mean | −46.8 | −50.6 | 3.8 |
| SEM | 3.0 | 1.8 | 2.0 |
| n | 5 | 5 | 5 |
| P | | 0.124 | |
| Normalised Membrane Potential | | | |
|  | Rest | LAT9993 S 5 µM | ΔVm |
| Mean | 100 | 109.2 | −9.2 |
| SEM | | 5.1 | 5.1 |
| n | 5 | 5 | 5 |
| P | | 0.144 | |
|  | Control | LAT9993 LoopS 5 µM | ΔIR |
| Input Resistance (MΩ) | | | |
| Mean | 810.0 | 788.0 | 22.1 |
| SEM | 184.2 | 191.9 | 24.2 |
| n | 5 | 5 | 5 |
| P | | 0.413 | |
| Normalised Input Resistance | | | |
| Mean | 100 | 95.6 | 4.4 |
| SEM | | 5.9 | 5.9 |
| n | 5 | 5 | 5 |
| P | | 0.493 | |

Discussion

This study investigated the effects of LAT9993 Loop and LAT9993 Loops on neuropathic pain using an in vitro spinal cord slice with intact dorsal root afferents combined with single-cell whole-cell patch clamp electrophysiological recording technique. The effects of LAT9993 Loop and LAT9993 LoopS (5 µM) were investigated on dorsal horn neurons in spinal cord slices prepared from Chung models of neuropathic pain. LAT9993 Loop induced a suppression of dorsal root afferent-mediated EPSPs.

The effects of LAT9993 Loop closely resemble those observed with SEQ ID NO:26 (also referred to herein as LAT9993), suggesting common mechanisms mediate the effects of these compounds on dorsal horn neurons.

LAT9993 LoopS principally induced inhibition of dorsal horn neurons or was without significant effect. LAT9993 Loops induced a suppression of dorsal root afferent-mediated EPSPs, in one neurone selectively.

Example 4: Comparative Analysis of the Effects of Peptides of Formula (I) (SEQ ID NO:1; Also Referred to Herein as LAT9993 Variants) on Dorsal Horn Neurons and Dorsal Root Afferent-Mediated Synaptic Transmission in a Rat Model of Neuropathic Pain Material and Methods
A. Animals Adult male Sprague-Dawley rats, weighing 220-250 g (aged/weeks and older) at the time of surgery, were used in this study. They were housed in groups of 4, in an air-conditioned room, on a 12-hour light/dark cycle with food and water available ad libitum. All experiments were performed in accordance with the U.K. Animals (Scientific Procedures) Act (1986).

The animals were housed in groups of 4 in an air-conditioned room on a 12-hour light/dark cycle. Food and water were available ad libitum. They were allowed to acclimatise to the environment for experiments for three days by leaving them on a raised metal mesh for at least 40 min. The baseline paw withdrawal threshold (PWT) was examined using a series of graduated von Frey hairs (see below) for 3 consecutive days before surgery and re-assessed on the $6^{th}$ to $8^{th}$ day after surgery and on the $12^{th}$ to $14^{th}$ day after surgery before drug dosing.

Each rat was anaesthetized with 5% isoflurane mixed with oxygen (2 L per min) followed by an intramuscular (i.m.) injection of ketamine 90 mg/kg plus xylazine 10 mg/kg. The back was shaved and sterilized with povidone-iodine. The animal was placed in a prone position and a para-medial incision was made on the skin covering the L4-6 level. The L5 spinal nerve was carefully isolated and tightly ligated with 6/0 silk suture. The wound was then closed in layers after a complete haemostasis. A single dose of antibiotics (Amoxipen, 15 mg/rat, i.p.) was routinely given for prevention of infection after surgery. The animals were placed in a temperature-controlled recovery chamber until fully awake before being returned to their home cages.

B. Formulation and Administration of the Test Compounds

LAT9993 LoopS (SEQ ID NO:28), SEQ11+LAT9993 Loop (SEQ ID NO:32; IDPSSEAPGHSCRSRPVESSC), SEQ25+LAT9993 Loop (SEQ ID NO:33; CRSRPVESS-CSSKFSWDEYEQYKKE), LAT9993 SLoop A4 (SEQ ID NO:30), LAT9993 SLoop A7 (SEQ ID NO:31), LAT9993 SLoop A9 (SEQ ID NO:34; SCRSRPVEASC) and LAT9993 SLoop A10 (SEQ ID NO:35; SCRSRPVESAC), were solubilised in distilled water and made up as concentrated stocks and stored frozen until the day of experiment when they were diluted to the required test concentrations in artificial cerebrospinal fluid (aCSF), as described in Example 3, above.

C. Study Procedures

Ten to fourteen days after surgery, animals were placed in individual Perspex boxes on a raised metal mesh for at least 40 minutes prior to PWT testing. Starting with the filament of lowest force (1 g), each filament was applied perpendicularly to the centre of the ventral surface of the paw until slightly bent for 6 seconds. If the animal withdrew or lifted its paw upon stimulation, a von Frey hair with force immediately lower than that tested was subsequently used. If no response was observed, then a hair with force immediately higher was tested. The lowest amount of force required to induce reliable responses (positive in 2 out of 3 trials) was recorded as the value of PWT. Only animals showing significant mechanical allodynia (PWT≤3.5 g) were selected for subsequent electrophysiological experiments (see FIG. 5).

D. Spinal Cord Slice Preparation

Once validation of a neuropathic state had been confirmed, animals were terminally anesthetized using isoflurane (Norvartis Animal Health UK Ltd.), cervically dislocated and decapitated. A laminectomy was performed and the spinal cord, with spinal roots and DRG attached, removed and cut into 250-450 μm thick slices using a Leica VT1000S vibrating microtome (Leica Microsystems UK, Milton Keynes, United Kingdom). Slices were maintained in artificial cerebrospinal fluid (aCSF) at room temperature for 1 hr after slicing before recording. For recording, individual slices were held between two grids in a custom-built chamber continuously perfused with aCSF at a rate of 4-10 ml.min$^{-1}$, illuminated from below, and viewed under a dissection microscope. The aCSF was of the following composition (mM): NaCl, 127; KCl, 1.9; $KH_2PO_4$, 1.2; $CaCl_2$, 2.4; $MgCl_2$, 1.3; $NaHCO_3$, 26; D-glucose, 10; equilibrated with 95% $O_2$-5% $CO_2$.

E. Electrophysiological Recording

Whole cell recordings were performed at 35±1° C. from neurons in the dorsal horn of spinal cord slices using a Multiclamp 700B amplifier, and the 'blind' version of the patch-clamp technique. Patch pipettes were pulled from thin-walled borosilicate glass with resistances of between 3 and 8 MΩ when filled with intracellular solution of the following composition (mM): potassium gluconate, 140, KCl, 10, EGTA-Na, 1, HEPES, 10, $Na_2ATP$, 4, Na-GTP, 0.3.

Recordings were monitored on an oscilloscope and stored on digital audio tapes for later off-line analysis. In addition, data were low-pass filtered at 2-5 kHz, (1 kHz for voltage-clamp data), digitized at 2-10 kHz and stored on a PC running pCLAMP 10 data acquisition software (Axon Instruments). Analysis of electrophysiological data was carried out using Clampfit 10 software.

F. Statistical Methods

Statistical analysis was performed using Student's paired t-test where appropriate, with probability values of less than 0.05 considered to indicate statistical significance, unless otherwise stated.

Results
A. Animal Health and Weight

Rats recovered well after surgery. Body weight gained 30-50 grams the first week after surgery, and 50-70 grams over the second week. Animals showed some degree of disuse of the affected paws or limping. However, the general appearance of the animals was not remarkably different from their naïve counterparts.

The aim of this study was to investigate the effects of seven peptide variants of formula (I) on spinal cord dorsal horn neurons—LAT9993 LoopS (SEQ ID NO:28), SEQ ID NO: 11+LAT9993 Loop (SEQ ID NO:32; SEQ11+LAT9993 Loop; IDPSSEAPGHSCRSRPVESSC), LAT9993 Loop+ SEQ ID NO:25 (SEQ ID NO:33; SEQ25+LAT9993 Loop; CRSRPVESSCSSKFSWDEYEQYKKE), LAT9993 SLoop A4 (SEQ ID NO:30; SCRARPVESSC), LAT9993 SLoop A7 (SEQ ID NO:31; SCRSRPAESSC), LAT9993 SLoop A9 (SEQ ID NO:34; SCRSRPVEASC) and LAT9993 SLoop A10 (SEQ ID NO:35; SCRSRPVESAC).

B. The Effects of LAT9993 Loops on Dorsal Horn Neurons

The effects of LAT9993 LoopS (1 μM) were investigated on 3 dorsal horn neurons in spinal cord slices prepared from Chung models of neuropathic pain, recorded ipsilateral to the site of injury. In these neurons, LAT9993 LoopS induced a membrane hyperpolarisation and inhibition of activity in 1 neurone and induced membrane depolarisation in the other two neurons.

Figure 19:
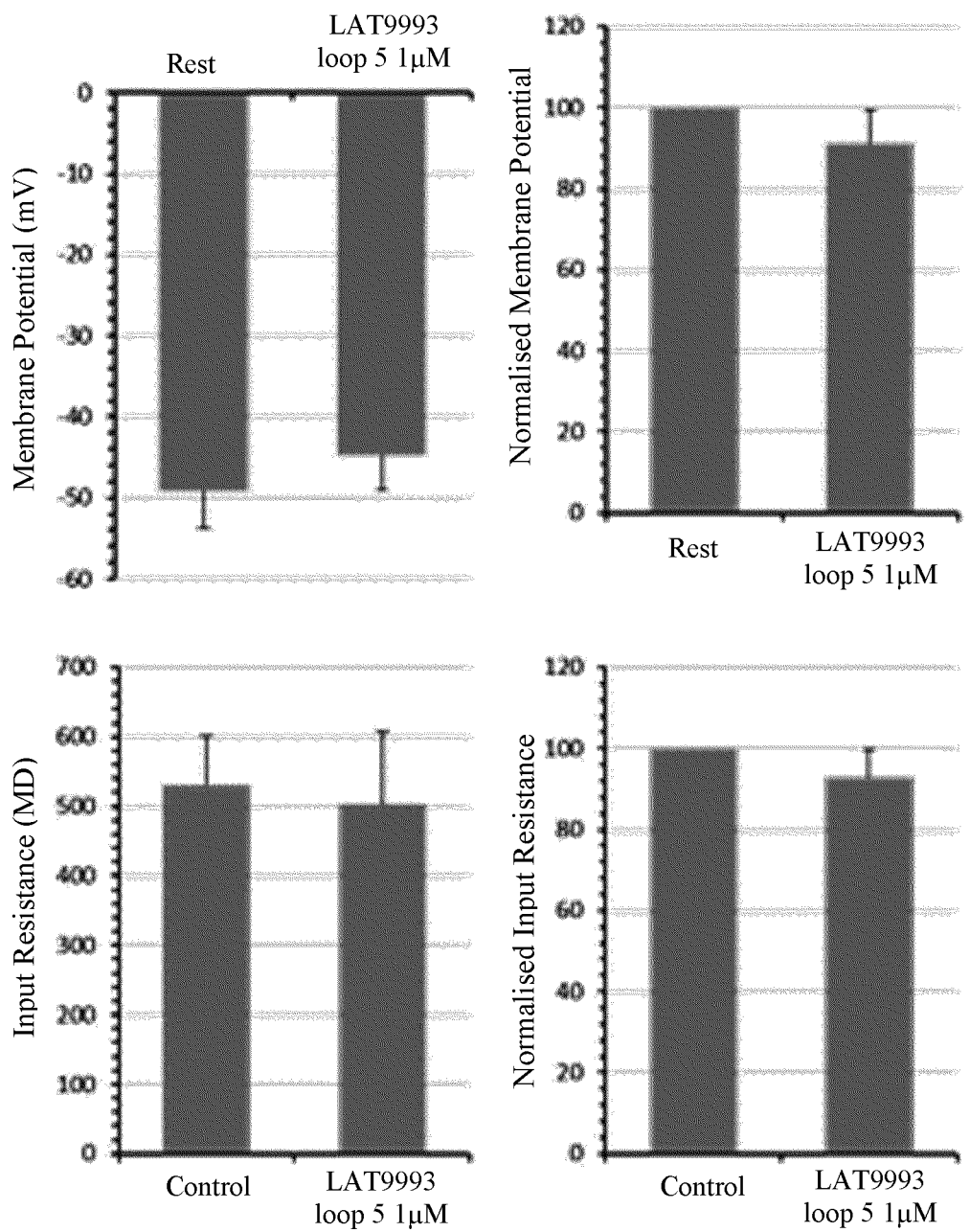

Data for all cells (n=3) showed LAT9993 LoopS induced membrane depolarisation from a mean resting membrane potential of −49.2±4.6 mV to a new steady-state resting potential of −44.7±4.3 mV, amounting to a 4.5±3.7 mV change in membrane potential (n=3, P=0352, Table 4). LAT9993 LoopS-induced responses were associated overall with a reduction in neuronal input resistance, indicated by the fall in amplitude of electrotonic potentials evoked in response to constant amplitude rectangular-wave current pulses (0.1 Hz; 10-600 pA; 0.5 to 1 s duration) and from the reduction in slope of plots of VI relations. Neuronal input resistance was reduced from a mean control resting level of 531.3±69.5 MΩ to 502.6±104.1 MΩ (n=3, P=0.498) in the presence of LAT9993 LoopS, amounting to a 28.7±34.9 MΩ reduction in neuronal input resistance. However, in one cell LAT9993-induced excitation was associated with a reduction in inward rectification and membrane depolarisation (see FIG. 20). FIG. 19 summarises the effects of LAT9993 LoopS on membrane properties of dorsal horn neurons (see also Table 4).

Figure 20:
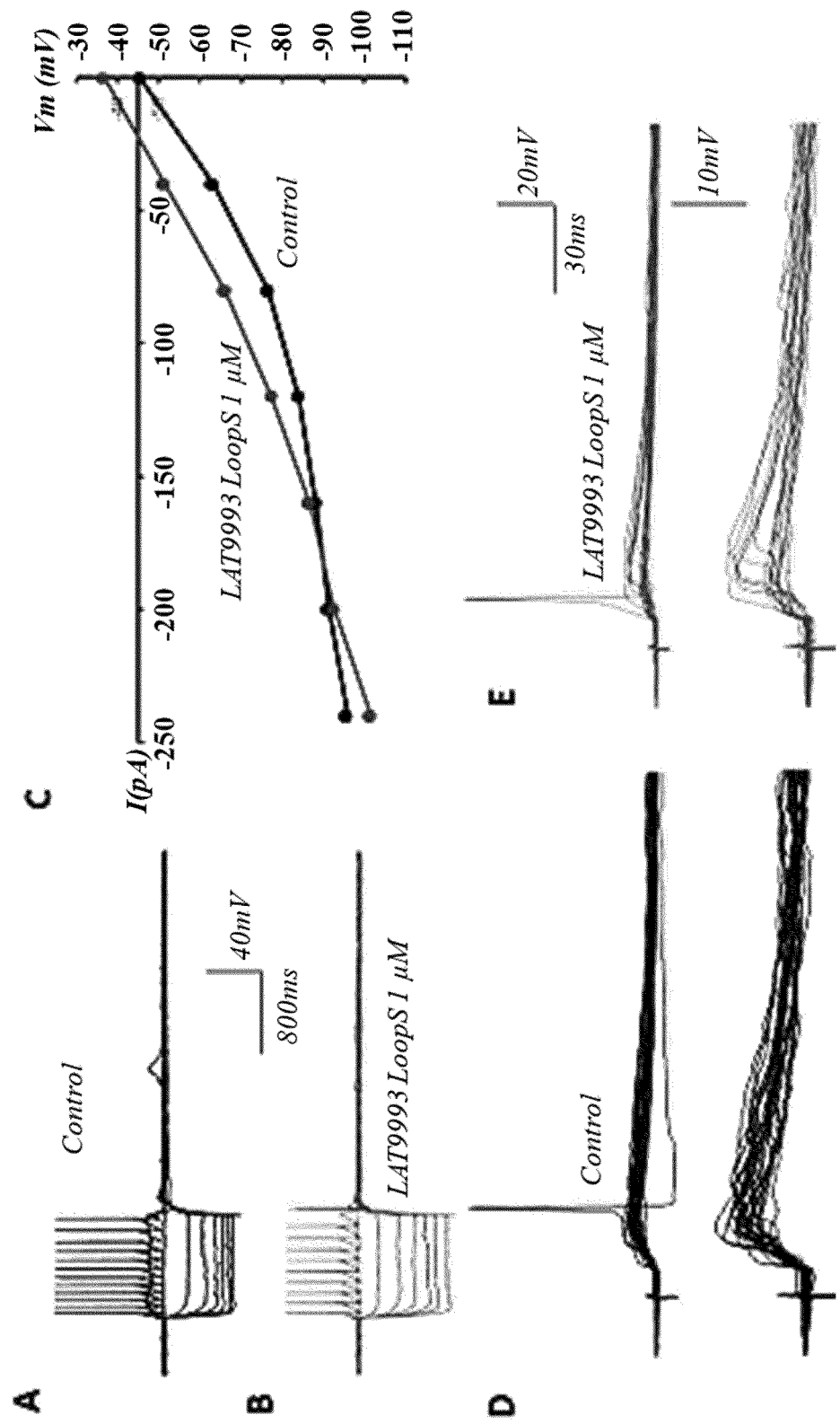
FIG. 20. A and B: LAT9993 Loop S-induced membrane depolarisation associated with an increase in neuronal input resistance. Voltage-current (VI) relations of the cell are shown. Voltage responses to current injection are shown superimposed. C shows a plot of the data from the same cell as in A and B in the presence of LAT9993 Loop S. Note the increase in the slope indicating an increase in neuronal input resistance indicating ion channels closing. The plots intersect around −85 mV (approaching the reversal potential for potassium ions under our recording conditions). Note also the increase in slope of the plot at more negative membrane potentials in LAT9993 Loop S indicating reduced inward rectification in the presence of the compound. D and E show superimposed excitatory postsynaptic potentials (EPSPs) evoked by dorsal root afferent stimulation. Subthreshold EPSPs are shown on a higher gain below. LAT9993 Loop S had little effect on dorsal root afferent-mediated EPSPs.

Wherever possible, the effects of LAT9993 LoopS were tested on dorsal root afferent-mediated synaptic inputs. LAT9993 LoopS either slightly suppressed dorsal root-evoked excitatory post-synaptic potentials (EPSPs) or had little effect (FIG. 20).

TABLE 4

Summary data of changes in membrane potential and input resistance associated with LAT9993 LoopS-induced responses in dorsal horn neurons from Chung models of neuropathic pain.

|  | Rest | LAT9993 LoopS 1 μM | ΔVm |
| --- | --- | --- | --- |
| | | Membrane Potential (mV) | |
| Mean | −49.2 | −44.7 | −4.5 |
| SEM | 4.6 | 4.3 | 3.7 |
| n | 3 | 3 | 3 |
| P | | 0.352 | |
| | | Normalised Membrane Potential | |
| Mean | 100 | 91.5 | 8.5 |
| SEM | | 7.8 | 7.8 |
| n | 3 | 3 | 3 |
| P | | 0.389 | |
|  | Control | LAT9993 LoopS 1 μM | ΔIR |
| | | Input Resistance (MΩ) | |
| Mean | 531.3 | 502.6 | 28.7 |
| SEM | 69.5 | 104.1 | 34.9 |
| n | 3 | 3 | 3 |
| P | | 0.498 | |
| | | Normalised Input Resistance | |
| Mean | 100 | 92.8 | 7.2 |
| SEM | | 6.9 | 6.9 |
| n | 3 | 3 | 3 |
| P | | 0.408 | |

C. The Effects of SEQ11+LAT9993 Loop on Dorsal Horn Neurons

The effects of SEQ11+LAT9993 Loop (1 μM) were investigated on 3 dorsal horn neurons in spinal cord slices prepared from Chung models of neuropathic pain, recorded ipsilateral to the site of injury. In these neurons, SEQ11+LAT9993 loop induced a membrane hyperpolarisation and inhibition of activity in 2 neurons and induced membrane depolarisation in the other neurone.

Figure 21:
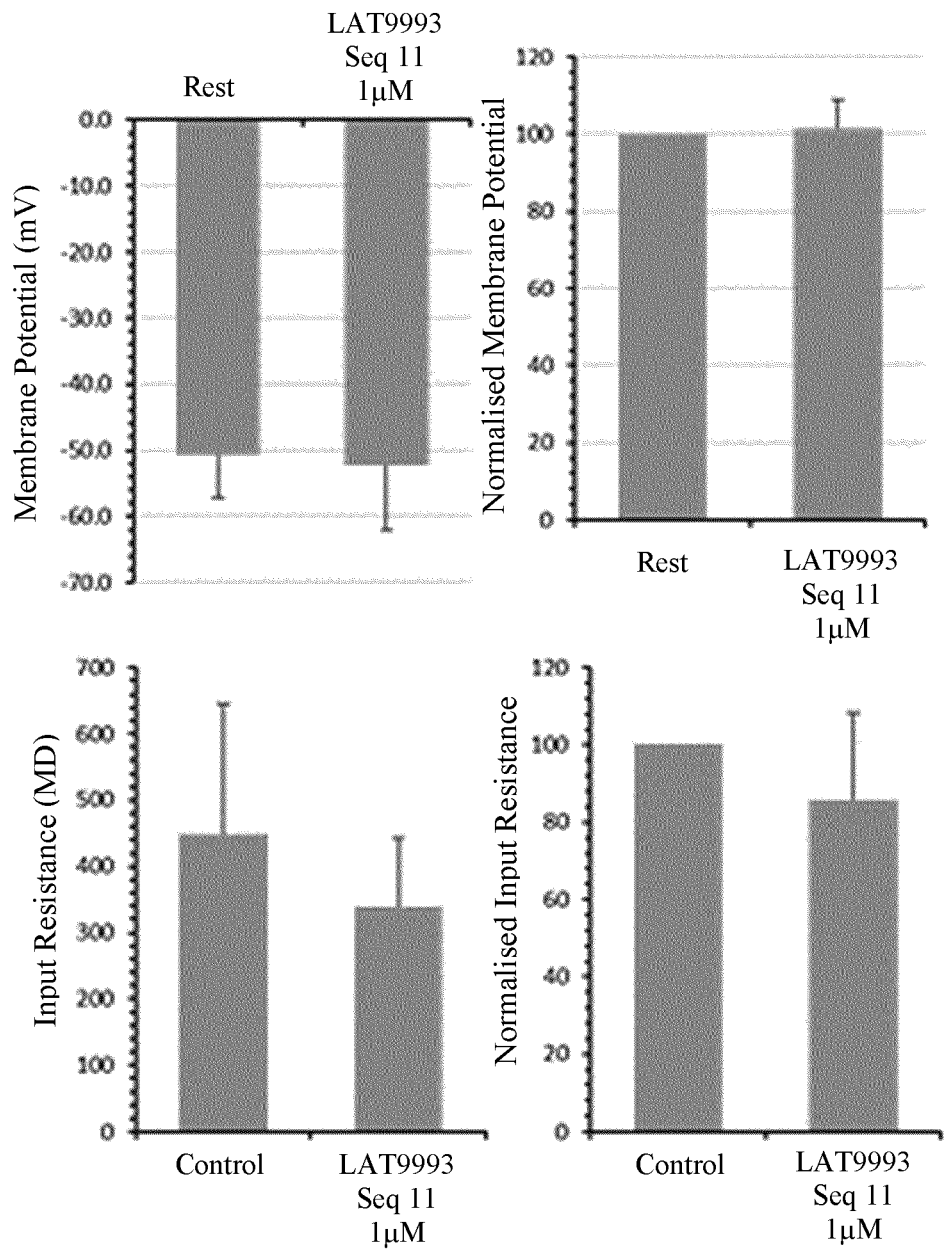
FIG. 21. Summary data showing changes in membrane potential and neuronal input resistance associated with SEQ11+LAT9993 Loop (SEQ ID NO:32)-induced responses in dorsal horn neurons from Chung models of neuropathic pain, (n=3).

Data for all cells (n=3) showed SEQ1.1+LAT9993 loop induced membrane hyperpolarisation from a mean resting membrane potential of −50.7±6.5 mV to a new steady-state resting potential of −52.3±9.8 mV, amounting to a 1.6±3.4 mV change in membrane potential (n=3, P=0.679, Table 5). SEQ11+LAT9993 Loop-induced responses were associated overall with a reduction in neuronal input resistance, indicated by the fall in amplitude of electrotonic potentials evoked in response to constant amplitude rectangular-wave current pulses (0.1 Hz; 10-600 pA; 0.5 to 1 s duration) and from the reduction in slope of plots of VI relations. Neuronal input resistance was reduced from a mean control resting level of 447.6±196.9 MΩ to 338.1±103.7 MΩ (n=3, P=0.517) in the presence of SEQ1.1+LAT9993 Loop, amounting to a 109.5±140.2 MΩ reduction in neuronal input resistance. FIG. 21 summarises the effects of SEQ11+LAT9993 loop on membrane properties of dorsal horn neurons (see also Table 5). Estimates of the reversal potentials for these responses, wherever possible, indicated activation of a chloride conductance (see FIG. 22).

Figure 22:
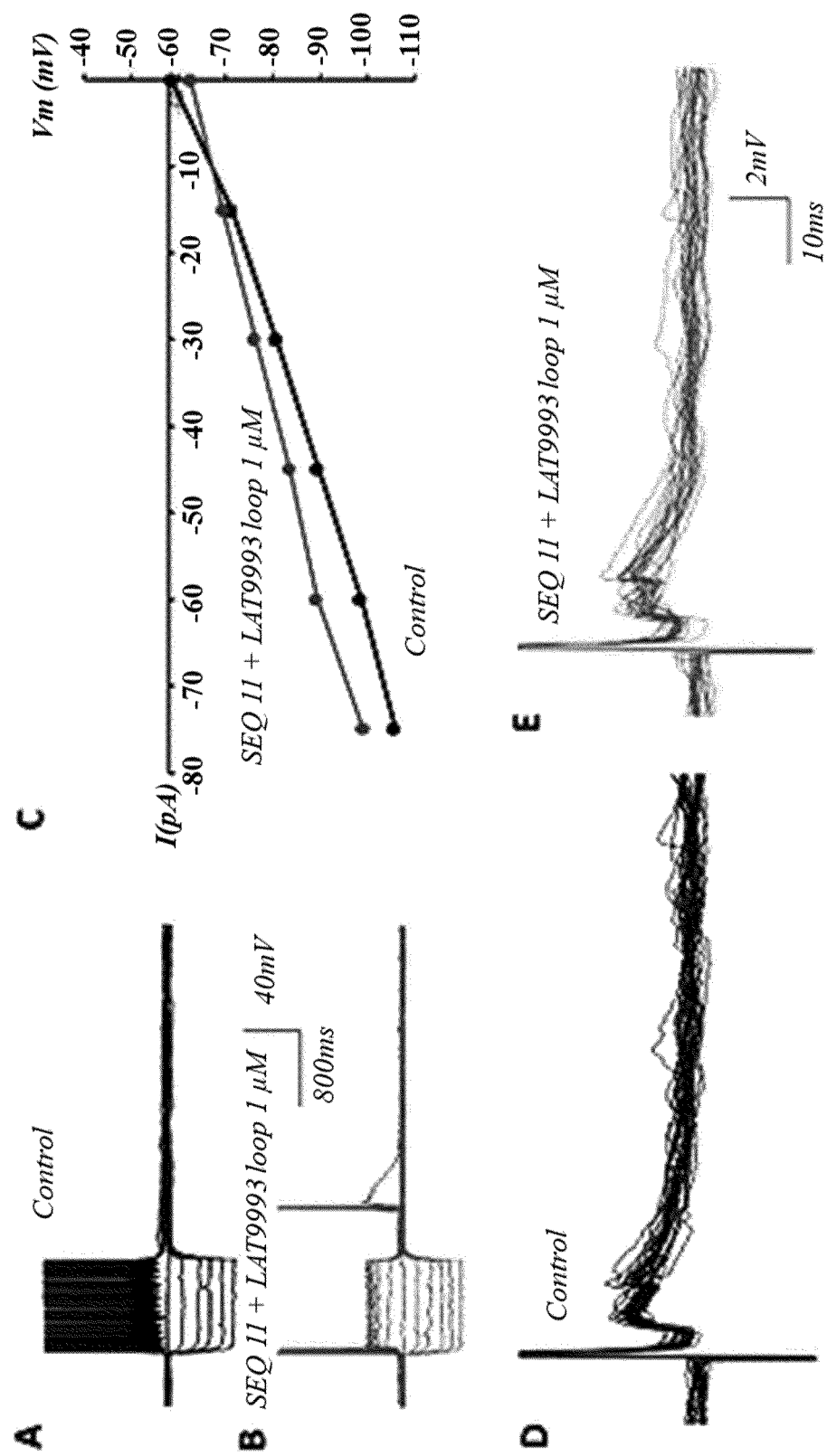
FIG. 22. A: SEQ11+LAT9993 Loop-induced hyperpolarisation associated with a reduction in neuronal input resistance. A and B: Voltage-current (VI) relations of the cell are shown. Voltage responses to current injection are shown superimposed. C shows a plot of the data from the same cell as in A and B in the presence of SEQ11+LAT9993 loop. Note the reduction in the slope indicating a reduction in neuronal input resistance indicating ion channel opening. The plots intersect around −65 mV (approaching the reversal potential for chloride ions under our recording conditions). D and E show superimposed excitatory postsynaptic potentials (EPSPs) evoked by dorsal root afferent stimulation. SEQ11+LAT9993 Loop (SEQ ID NO:32) had little effect on dorsal root afferent-mediated EPSPs.

Wherever possible, the effects of SEQ11+LAT9993 loop were tested on dorsal root afferent-mediated synaptic inputs. SEQ11+LAT9993 Loop had little effect on evoked post-synaptic potentials (FIG. 22).

TABLE 5

Summary data of changes in membrane potential and input resistance associated with SEQ11 + LAT9993 Loop-induced responses in dorsal horn neurons from Chung models of neuropathic pain.

|  | Rest | SEQ 11 + LAT9993 Loop 1 μM | ΔVm |
| --- | --- | --- | --- |
| | | Membrane Potential (mV) | |
| Mean | −50.7 | −52.3 | 1.6 |
| SEM | 6.5 | 9.8 | 3.4 |
| n | 3 | 3 | 3 |
| P | | 0.679 | |
| | | Normalised Membrane Potential | |
| Mean | 100 | 101.4 | −1.4 |
| SEM | | 7.5 | 7.5 |
| n | 3 | 3 | 3 |
| P | | 0.871 | |
|  | Control | SEQ 11 + LAT9993 Loop 1 μM | ΔIR |
| | | Input Resistance (MΩ) | |
| Mean | 447.6 | 338.1 | 109.5 |
| SEM | 196.9 | 103.7 | 140.2 |
| n | 3 | 3 | 3 |
| P | | 0.517 | |
| | | Normalised Input Resistance | |
| Mean | 100 | 85.6 | 14.4 |
| SEM | | 22.8 | 22.8 |
| n | 3 | 3 | 3 |
| P | | 0.592 | |

D. The Effects of SEQ25+LAT9993 Loop on Dorsal Horn Neurons

The effects of SEQ25+LAT9993 Loop (1 μM) were investigated on 3 dorsal horn neurons in spinal cord slices prepared from Chung models of neuropathic pain, recorded ipsilateral to the site of injury.

Figure 23:
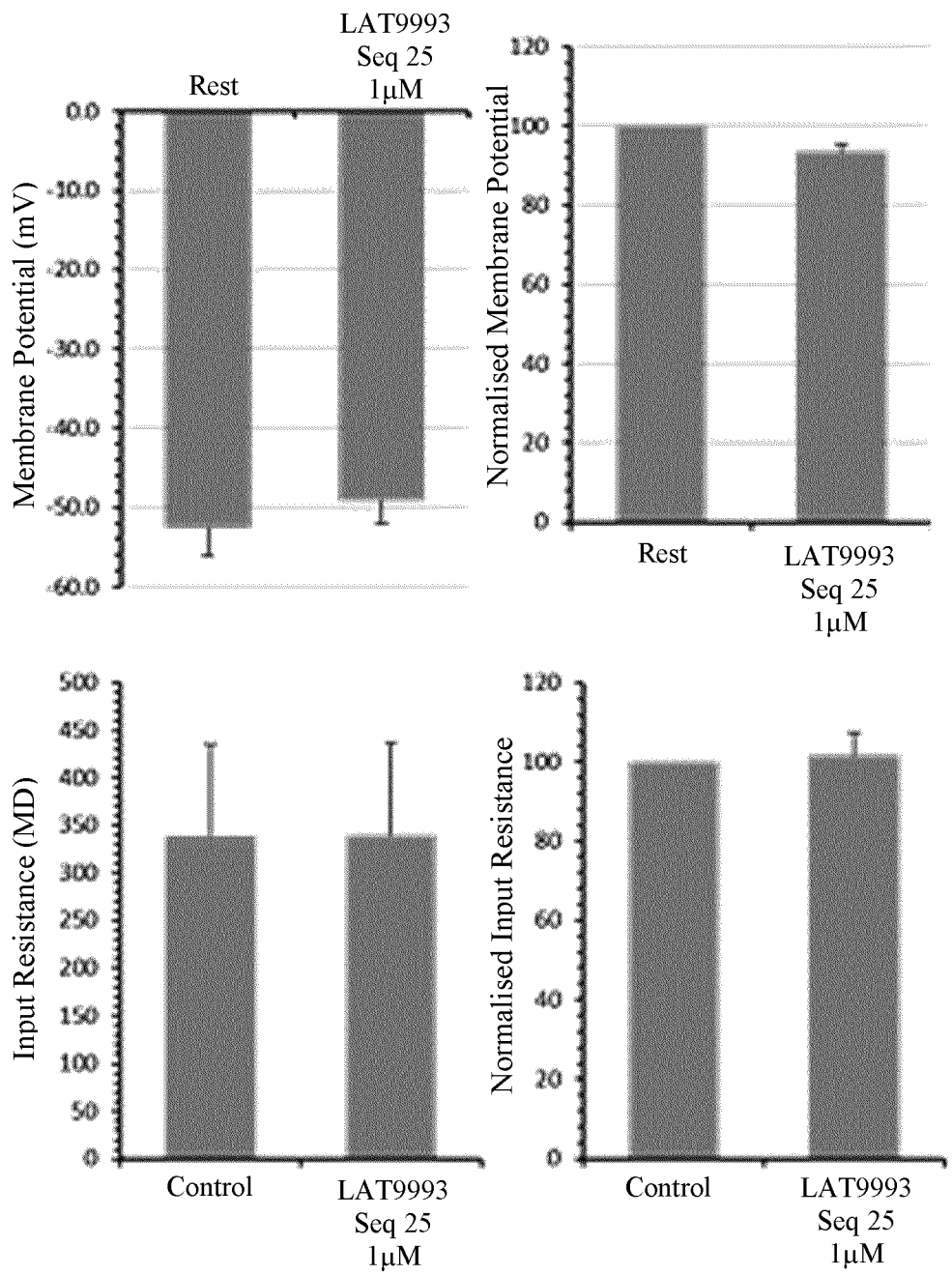
FIG. 23. Summary data showing changes in membrane potential and neuronal input resistance associated with SEQ25+LAT9993 Loop (SEQ ID NO:33)-induced responses in dorsal horn neurons from Chung models of neuropathic pain, (n=3).
Figure 24:
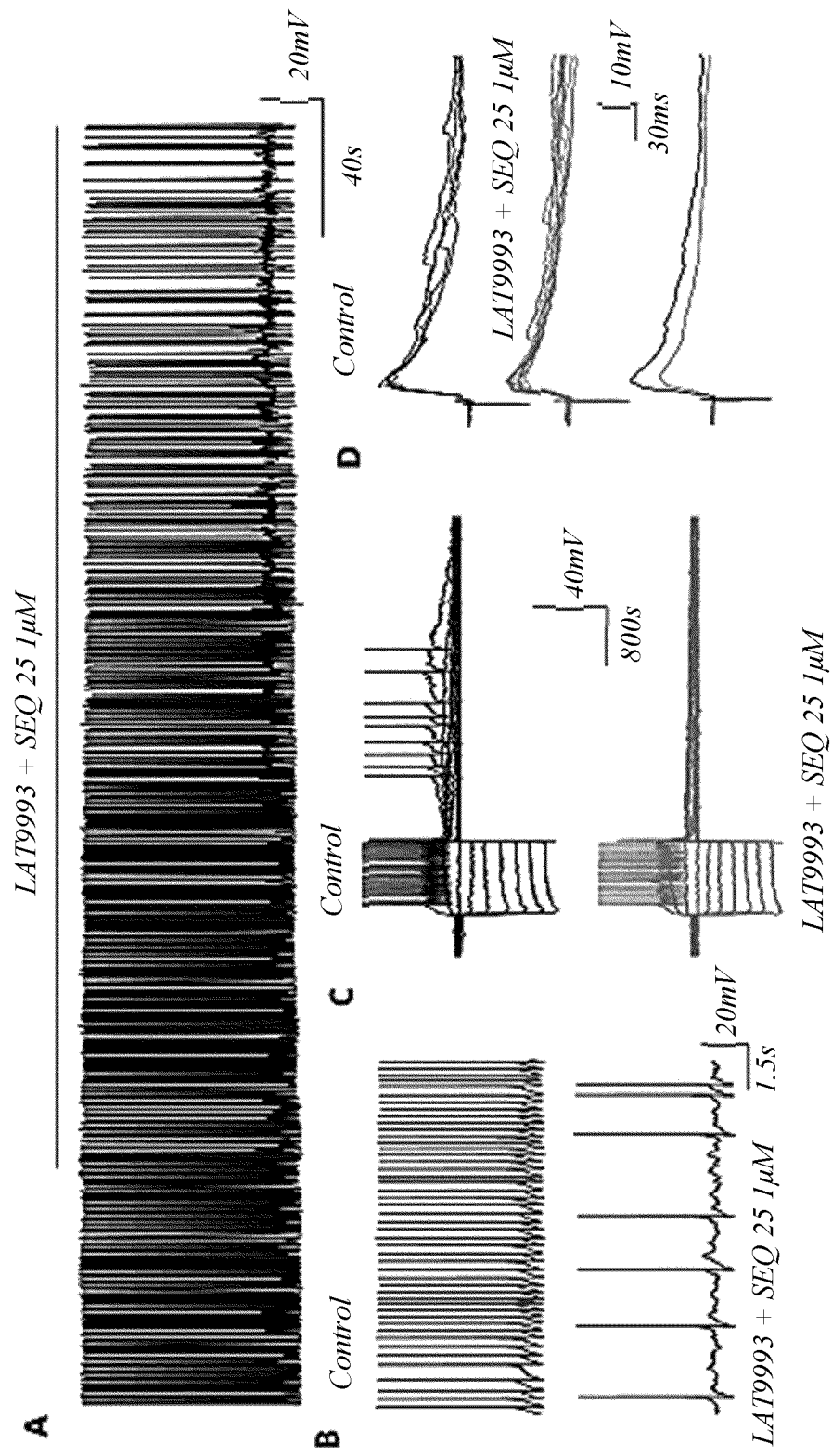
FIG. 24. SEQ25+LAT9993 Loop-induced hyperpolarisation mediated via activation of a potassium conductance. A. Samples of a continuous record showing SEQ25+LAT9993 Loop induced inhibition of spontaneous activity. B. Samples of the record shown in A. Note the decreased action potential discharge in SEQ25+LAT9993 Loop. C. VI relations of a cell in the absence (top) and presence of SEQ25+LAT9993 Loop. Note the reduction in the depolarising potential following current pulse termination and its absence in the presence of SEQ25+LAT9993 Loop. D show's superimposed exc wherein
$X^1$, $X^3$, $X^5$, and $X^6$ is an amino acid residue selected from the group consisting of serine, alanine, valine, leucine, isoleucine and glycine;
$X^2$ is alanine, arginine or lysine;
$X^4$ is glutamic acid or aspartic acid;
$R^1$ is selected from the group consisting of S, HS, GHS, PGHS, APGHS, EAPGHS, SEAPGHS, SSEAPGHS, PSSEAPGHS, DPSSEAPGHS and IDPSSEAPGHS, or $R^1$ is absent; and
$R^2$ is selected from the group consisting of S, SS, SSK, SSKF, SSKFS, SSKFSW, SSKFSWD, SSKFSWDE, SSKFSWDEY, SSKFSWDEYE, SSKFSWDEYEQ, SSKFSWDEYEQY, SSKFSWDEYEQYK, SSKFSWDEYEQYKK and SSKFSWDEYEQYKKE, or $R^2$ is absent; and
wherein the peptide of formula (I), or the pharmaceutically acceptable salt thereof, is a cyclic peptide formed by a disulphide bond between the two cysteine residues.

Data for all cells (n=3) showed SEQ25+LAT9993 Loop induced membrane depolarisation from a mean resting membrane potential of −52.5±3.6 mV to a new steady-state resting potential of −49.1±3.0 mV, amounting to a 3.4±0.9 mV change in membrane potential (n=3, P=0.069, Table 6). SEQ25+LAT9993 Loop-induced responses were associated overall with little change in neuronal input resistance. Neuronal input resistance was unaltered from a mean control resting level of 338.2±96.7 MΩ to 339.6±97.6 MΩ (n=3, P=0.944) in the presence of SEQ25+LAT9993 Loop, amounting to a 1.4±18.2 MΩ increase in neuronal input resistance. FIG. 23 summarises the effects of SEQ25+LAT9993 Loop on membrane properties of dorsal horn neurons (see also Table 6). In one cell SEQ25+LAT9993 Loop induced inhibition of spontaneous activity and suppressed an after-depolarising potential, the latter observed to follow responses to depolarising current injection (see FIG. 24).

Wherever possible, the effects of SEQ25+LAT9993 Loop were tested on dorsal root afferent-media ted synaptic inputs. SEQ25+LAT9993 Loop suppressed dorsal root-evoked excitatory posts-synaptic potentials (EPSPs) in one neurone.

TABLE 6

Summary data of changes in membrane potential and input resistance associated with LAT9993 Loop + SEQ 25-induced responses in dorsal horn neurons from Chung models of neuropathic pain.

|  | Rest | SEQ25 + LAT9993 Loop 1 μM | ΔVm |
|---|---|---|---|
|  | Membrane Potential (mV) | | |
| Mean | −52.5 | −49.1 | −3.4 |
| SEM | 3.6 | 3.0 | 0.9 |
| n | 3 | 3 | 3 |
| P |  | 0.069 |  |
|  | Normalised Membrane Potential | | |
| Mean | 100 | 93.7 | 6.3 |
| SEM |  | 1.6 | 1.6 |
| n | 3 | 3 | 3 |
| P |  | 0.059 |  |
|  | Control | SEQ25 + LAT9993 Loop 1 μM | ΔIR |
|  | Input Resistance (MΩ) | | |
| Mean | 338.2 | 339.6 | −1.4 |
| SEM | 96.7 | 97.6 | 18.2 |
| n | 3 | 3 | 3 |
| P |  | 0.944 |  |
|  | Normalised Input Resistance | | |
| Mean | 100 | 101.7 | −1.7 |
| SEM |  | 5.6 | 5.6 |
| n | 3 | 3 | 3 |
| P |  | 0.785 |  |

E. The Effects of LAT9993 SLoop A4 on Dorsal Horn Neurons

The effects of LAT9993 SLoop A4 (1 μM) were investigated on 4 dorsal horn neurons in spinal cord slices prepared from Chung models of neuropathic pain, recorded ipsilateral to the site of injury. In these neurons, LAT9993 SLoop A4 induced a membrane hyperpolarisation and inhibition of activity in 1 neurone and induced membrane depolarisation in 3 neurons.

Figure 25:
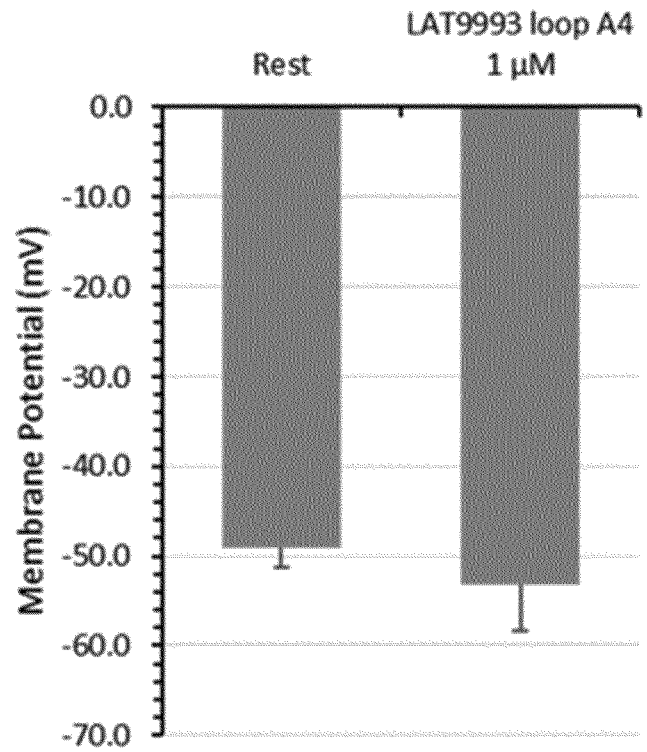
Figure 25:
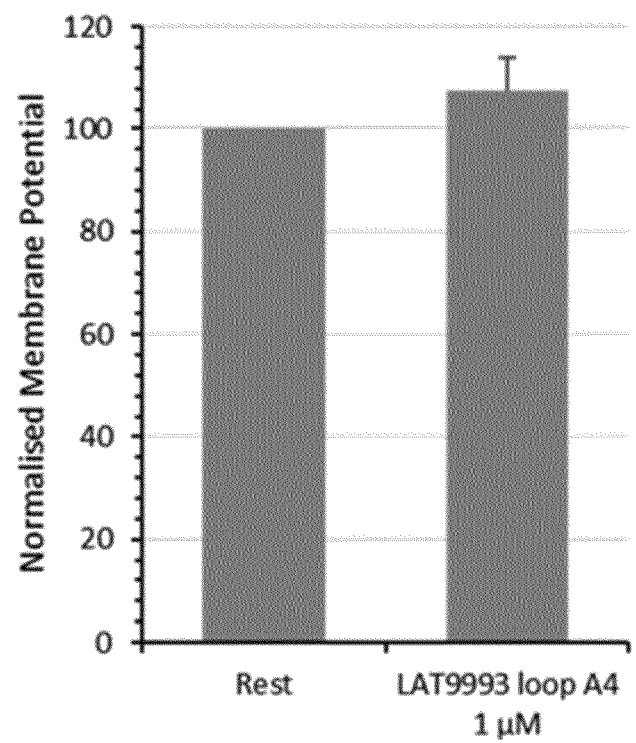
Figure 25:
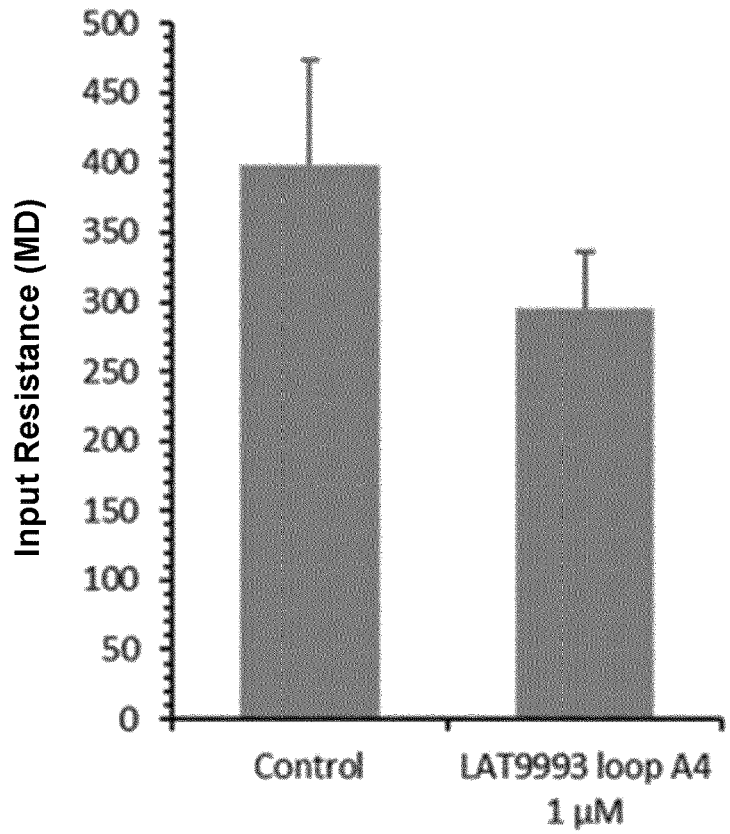
Figure 25:
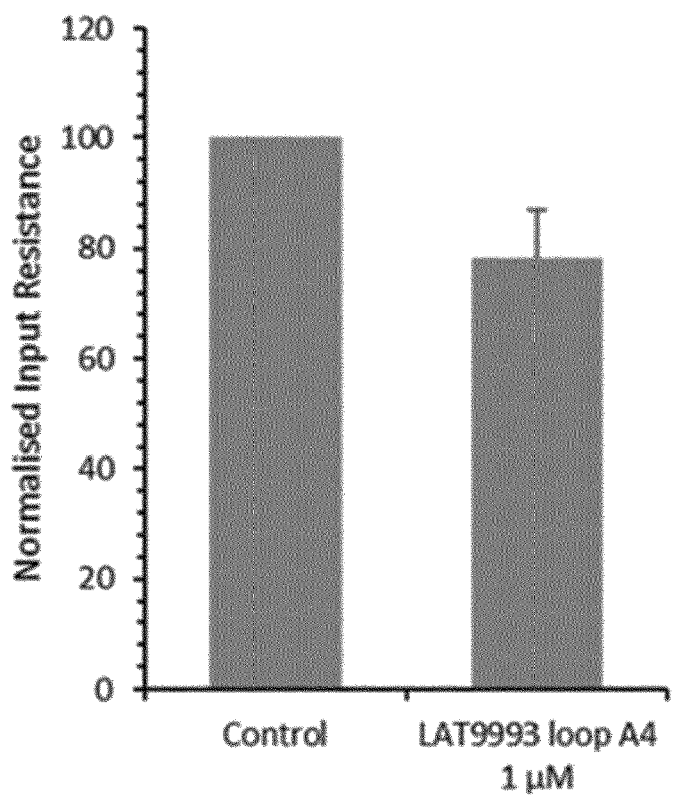
Figure 26:
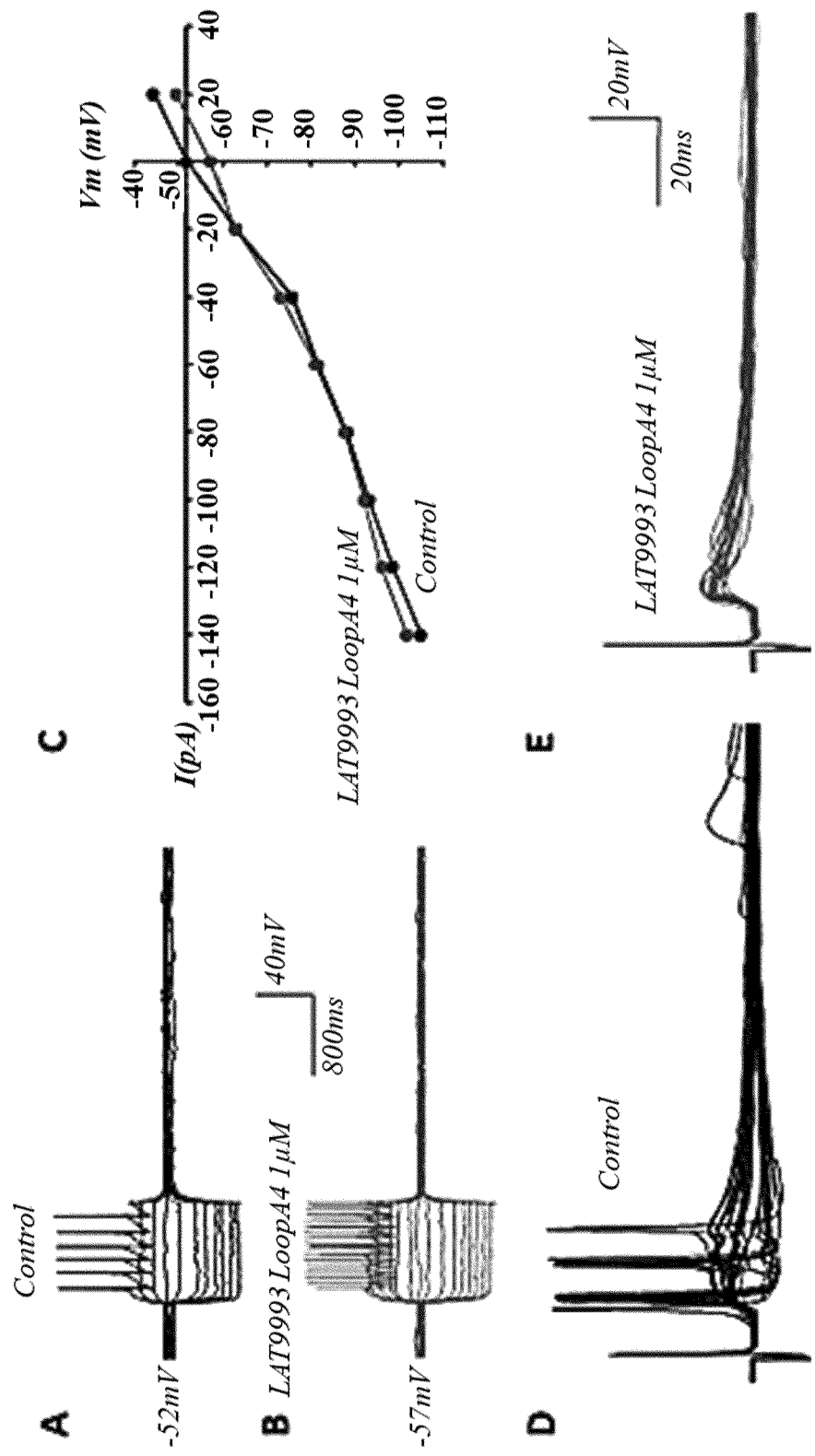

Data for all cells (n=4) showed LAT9993 SLoop A4 induced membrane hyperpolarisation from a mean resting membrane potential of −49.1±2.2 mV to a new steady-state resting potential of −53.3±5.1 mV, amounting to a 4.2±3.1 mV change in membrane potential (n=4, P=0.261, Table 7). LAT9993 SLoop A4-induced responses were associated overall with a reduction in neuronal input resistance, indicated by the fall in amplitude of electrotonic potentials evoked in response to constant amplitude rectangular-wave current pulses (0.1 Hz; 10-600 pA; 0.5 to 1 s duration) and from the reduction in slope of plots of VI relations. Neuronal input resistance was reduced from a mean control resting level of 397.7±76.5 MΩ to 294.6±40.7 MΩ (n=4, P=0.160) in the presence of LAT9993 SLoop A4, amounting to a 103.1±55.5 MΩ reduction in neuronal input resistance. FIG. 25 summarises the effects of LAT9993 SLoop A4 on membrane properties of dorsal horn neurons (see also Table 7). LAT9993 SLoop A4 induced responses could be associated with both an enhancement in inward rectification and/or activation of a chloride conductance (see FIG. 26).

Wherever possible, the effects of LAT9993 SLoop A4 were tested on dorsal root afferent-mediated synaptic inputs. LAT9993 SLoop A4 suppressed dorsal root-evoked excitatory posts-synaptic potentials (EPSPs; FIG. 25).

TABLE 7

Summary data of changes in membrane potential and input resistance associated with LAT9993 SLoop A4-induced responses in dorsal horn neurons from Chung models of neuropathic pain.

|  | Rest | LAT9993 Sloop A4 1 μM | ΔVm |
|---|---|---|---|
|  | Membrane Potential (mV) | | |
| Mean | −49.1 | −53.3 | 4.2 |
| SEM | 2.2 | 5.1 | 3.1 |
| n | 4 | 4 | 4 |
| P |  | 0.267 |  |
|  | Normalised Membrane Potential | | |
| Mean | 100 | 107.7 | −7.7 |
| SEM |  | 6.2 | 6.2 |
| n | 4 | 4 | 4 |
| P |  | 0.304 |  |
|  | Control | LAT9993 Sloop A4 1 μM | ΔIR |
|  | Input Resistance (MΩ) | | |
| Mean | 397.7 | 294.6 | 103.1 |
| SEM | 76.5 | 40.7 | 55.5 |
| n | 4 | 4 | 4 |
| P |  | 0.160 |  |
|  | Normalised Input Resistance | | |
| Mean | 100 | 78.3 | 21.7 |
| SEM |  | 8.8 | 8.8 |
| n | 4 | 4 | 4 |
| P |  | 0.089 |  |

The Effects of LAT9993 SLoop A7 on Dorsal Horn Neurons

The effects of LAT9993 SLoop A7 (1 μM) were investigated on 3 dorsal horn neurons in spinal cord slices prepared from Chung models of neuropathic pain, recorded ipsilateral to the site of injury. In these neurons, LAT9993 SLoop A7 induced a membrane hyperpolarisation and inhibition of activity in 1 neurone, induced membrane depolarisation in 1 neurone and had no effect on membrane potential in the remaining neurone.

Figure 27:
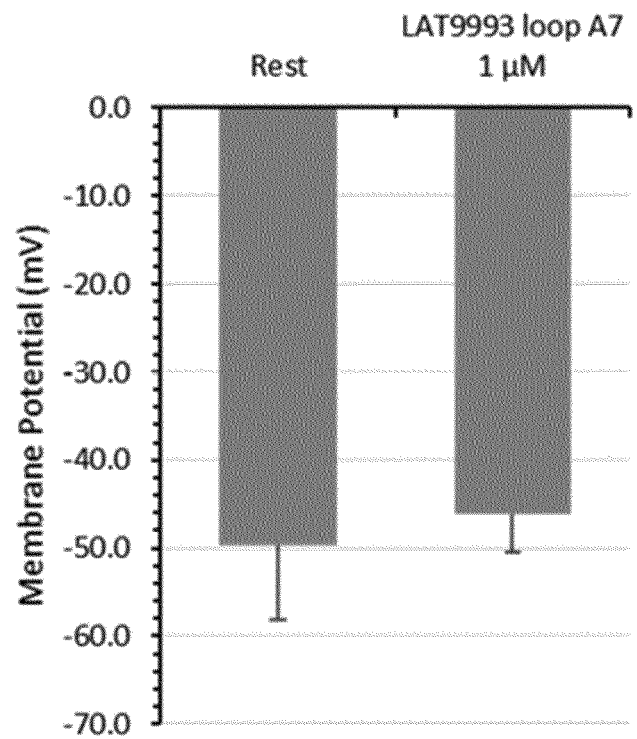
Figure 27:
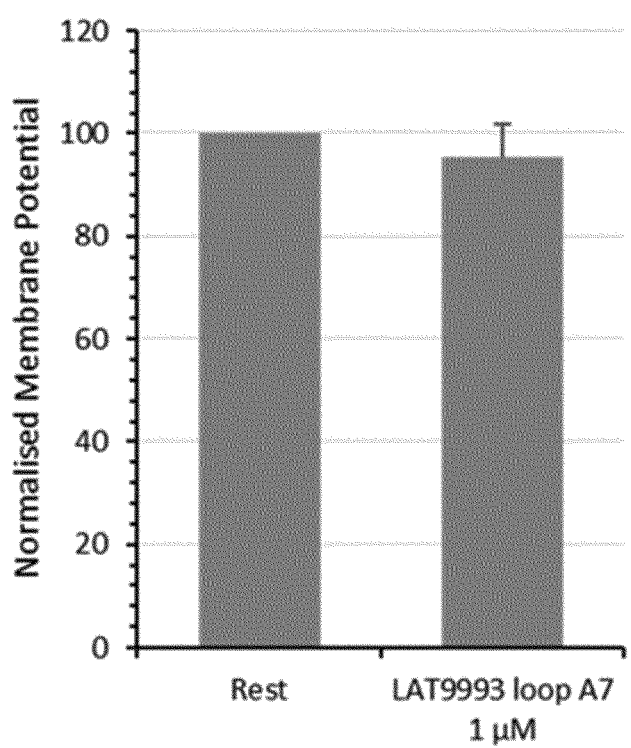
Figure 27:
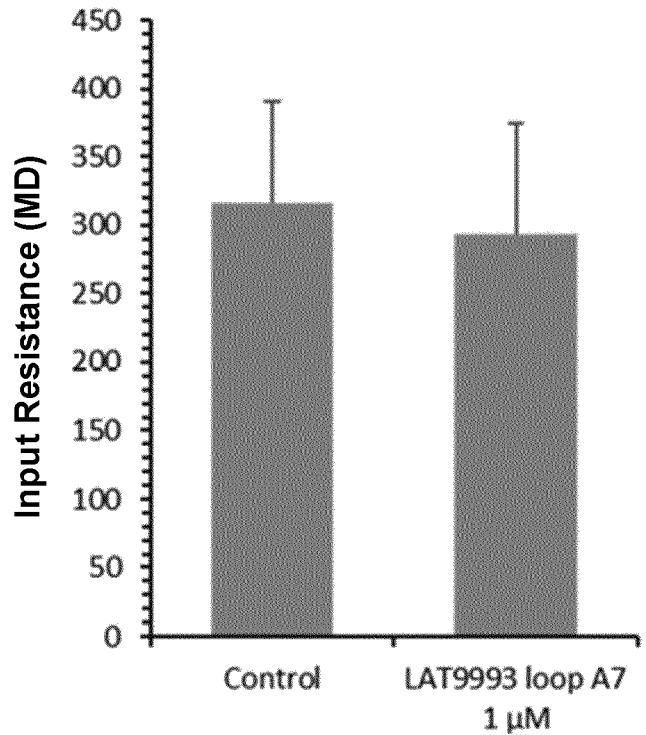
Figure 27:
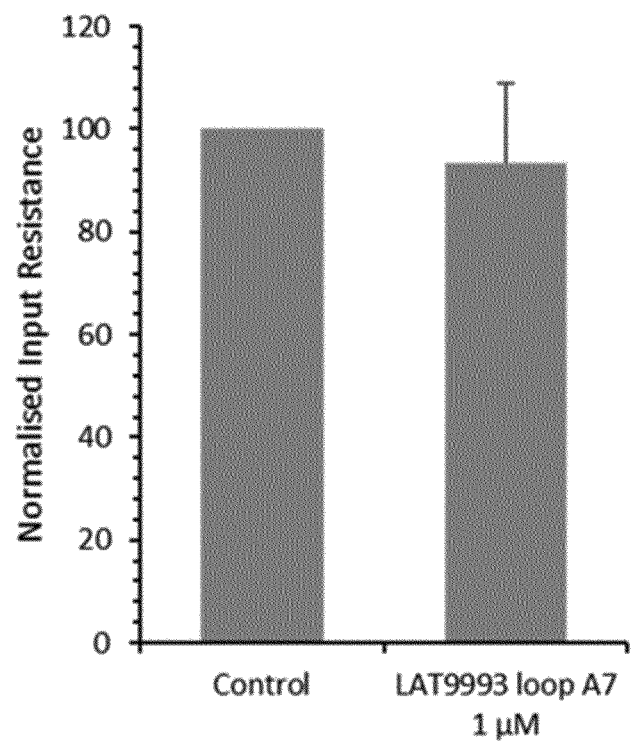
Figure 28:
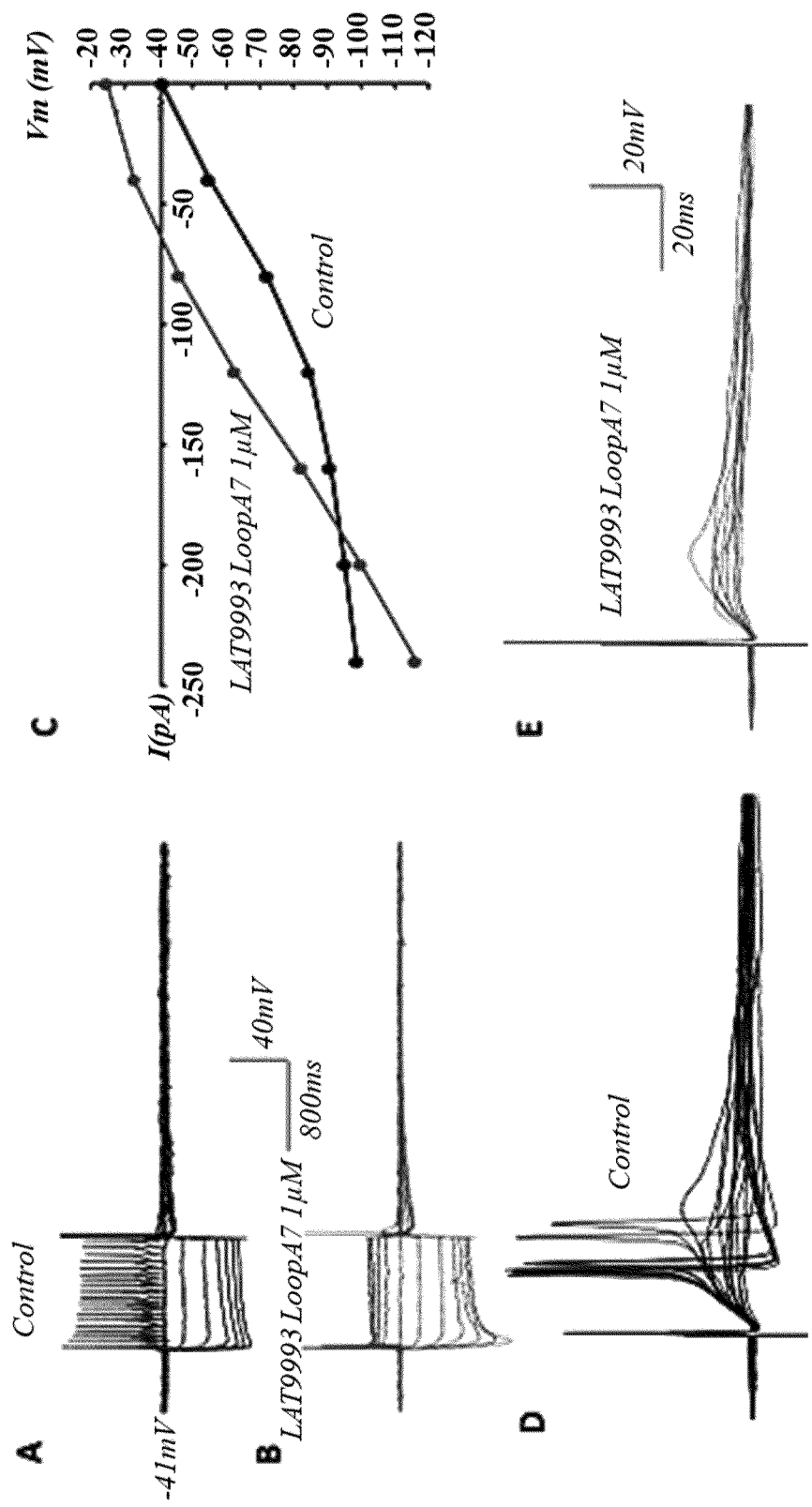

Data for all cells (n=3) showed LAT9993 SLoop A7 induced membrane depolarisation from a mean resting membrane potential of −49.6±8.5 mV to a new steady-state resting potential of −46.2±4.3 mV, amounting to a 3.4±43 mV change in membrane potential (n=3, P=0.502, Table 8). LAT9993 SLoop A7-induced responses were associated overall with a reduction in neuronal input resistance, indicated by the fall in amplitude of electrotonic potentials evoked in response to constant amplitude rectangular-wave current pulses (0.1 Hz; 10-600 pA; 0.5 to 1 s duration) and from the reduction in slope of plots of VI relations. Neuronal input resistance was reduced from a mean control resting level of 315.7±75.4 MΩ to 292.9±81.3 MΩ (n=3, P=0.740) in the presence of LAT9993 SLoop A7, amounting to a 22.8±59.8 MΩ reduction in neuronal input resistance. FIG. 27 summarises the effects of LAT9993 SLoop A7 on membrane properties of dorsal horn neurons (see also Table 8). In one neurone LAT9993 SLoop A7 induced membrane depolarisation associated with an increase in neuronal input resistance via block of a potassium conductance. This response was characterised by inhibition of inward rectification (see FIG. 28).

Wherever possible, the effects of LAT9993 SLoop A7 were tested on dorsal root afferent-mediated synaptic inputs. LAT9993 SLoop A7 suppressed dorsal root-evoked excitatory posts-synaptic potentials (EPSPs) in some neurons (FIG. 27).

TABLE 8

Summary data of changes in membrane potential and input resistance associated with LAT9993 SLoop A7-induced responses in dorsal horn neurons from Chung models of neuropathic pain.

|  | Rest | LAT9993 SLoop A7 1 μM | ΔVm |
|---|---|---|---|
|  | Membrane Potential (mV) | | |
| Mean | −49.6 | −46.2 | −3.4 |
| SEM | 8.5 | 4.3 | 4.3 |
| n | 3 | 3 | 3 |
| P |  | 0.502 |  |
|  | Normalised Membrane Potential | | |
| Mean | 100 | 95.3 | 4.7 |
| SEM |  | 6.7 | 6.7 |
| n | 3 | 3 | 3 |
| P |  | 0.555 |  |
|  | Control | LAT9993 SLoop A7 1 μM | ΔIR |
|  | Input Resistance (MΩ) | | |
| Mean | 315.7 | 292.9 | 22.8 |
| SEM | 75.4 | 81.3 | 59.8 |
| n | 3 | 3 |  |
| P |  | 0.740 |  |
|  | Normalised Input Resistance | | |
| Mean | 100 | 93.3 | 6.7 |
| SEM |  | 15.8 | 15.8 |
| n | 3 | 3 | 3 |
| P | 0 | 0.711 |  |

The Effects of LAT9993 SLoop A3 on Dorsal Horn Neurons

The effects of LAT9993 SLoop A9 (1 μM) were investigated on 3 dorsal horn neurons in spinal cord slices prepared from Chung models of neuropathic pain, recorded ipsilateral to the site of injury. In these neurons, LAT9993 Loop A9 induced a membrane depolarisation in all neurons.

Figure 29:
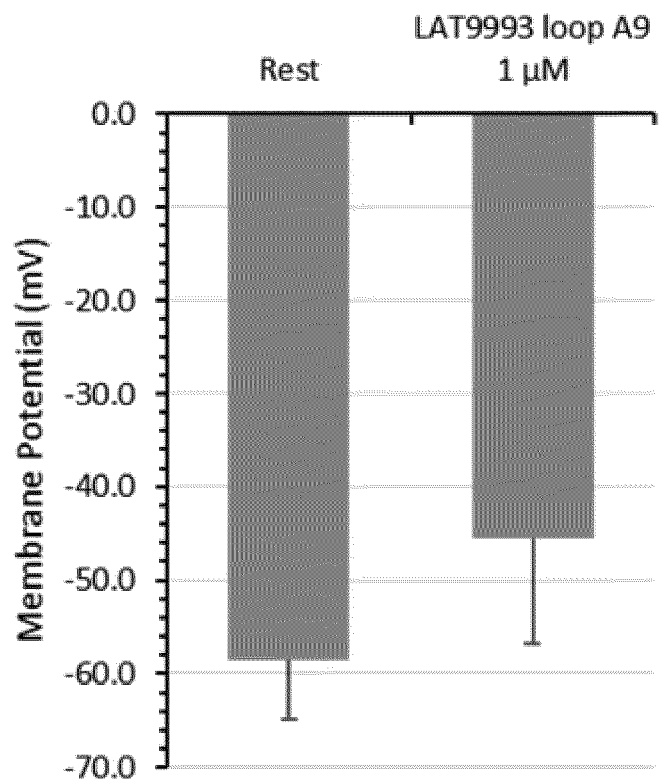
Figure 29:
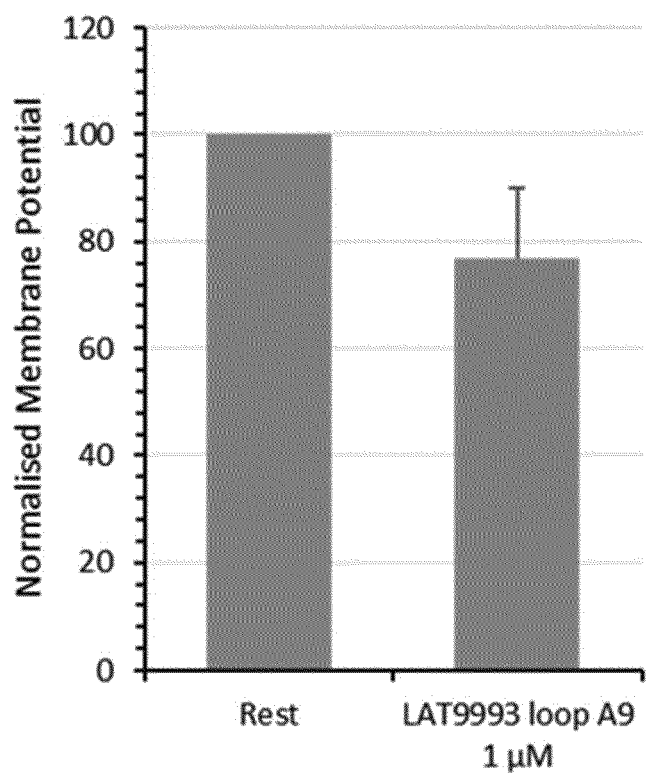
Figure 29:
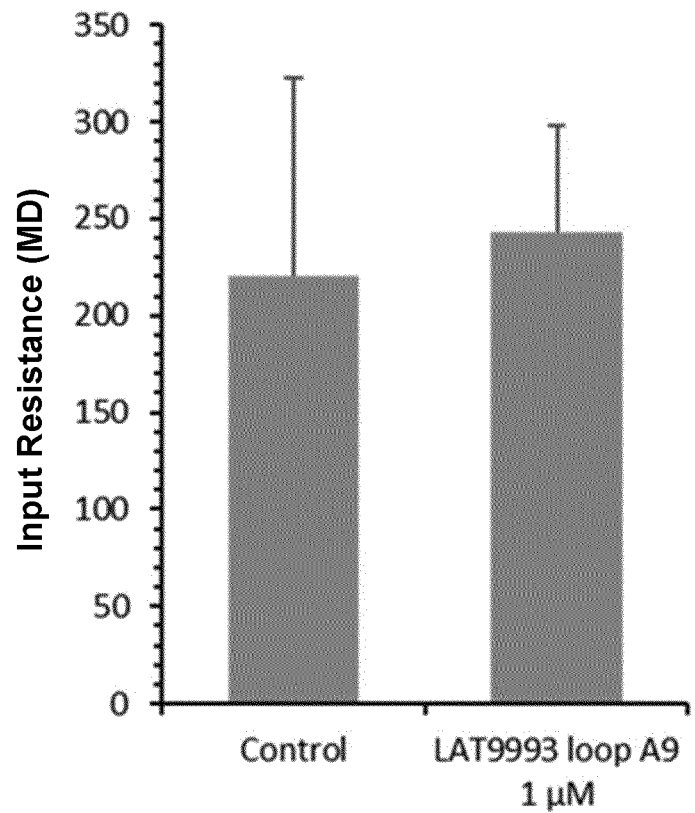
Figure 29:
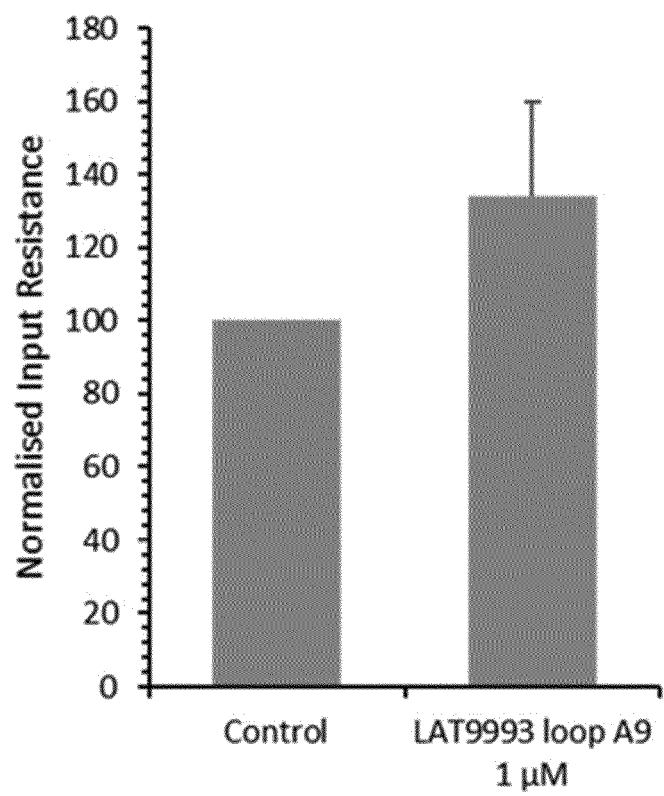
Figure 30:
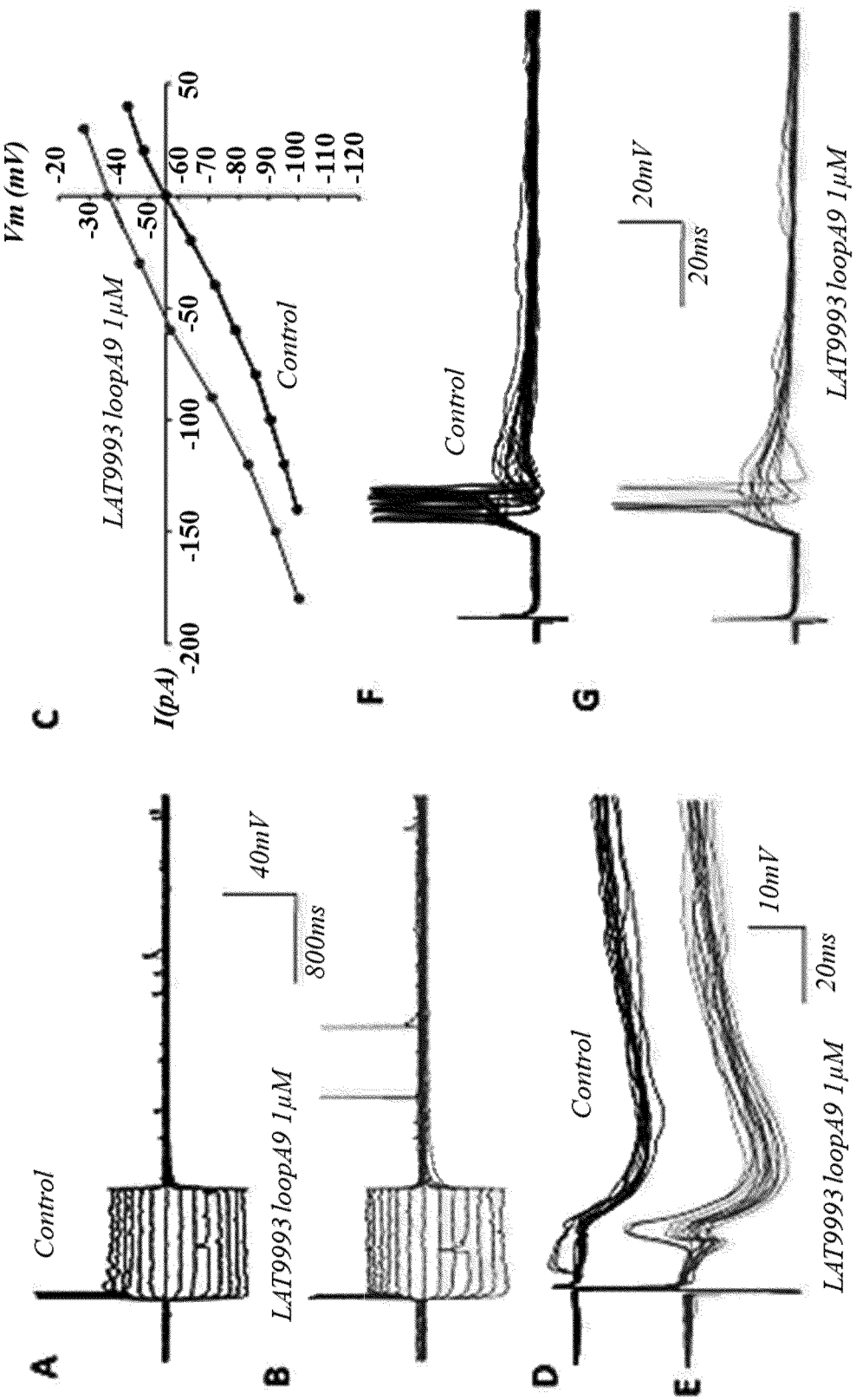

Data for all cells (n=3) showed LAT9993 SLoop A9 induced membrane depolarisation from a mean resting membrane potential of −58.4±6.5 mV to a new steady-state resting potential of −45.6±11.2 mV, amounting to a 12.9±7.3 mV change in membrane potential (n=3, P=0.221, Table 9). LAT9993 SLoop A9-induced responses were associated overall with an increase in neuronal input resistance, indicated by the marginal increase in amplitude of electrotonic potentials evoked in response to constant amplitude rectangular-wave current pulses (0.1 Hz; 10-600 pA; 0.5 to 1 s duration) and from the increase in slope of plots of VI relations. Neuronal input resistance was increased from a mean control resting level of 220.6±101.6 MΩ to 243.1±54.4 MΩ (n=4, P=0.694) in the presence of LAT9993 SLoop A9, amounting to a 22.5±49.6 MΩ increase in neuronal input resistance. FIG. 29 summarises the effects of LAT9993 SLoop A9 on membrane properties of dorsal horn neurons (see also Table 9). VI relations revealed no obvious reversal potentials but did show parallel shifts in the presence of the compound indicating the possible involvement of electrogenic ion pumps (see FIG. 30).

Wherever possible, the effects of LAT9993 SLoop A9 were tested on dorsal root afferent-mediated synaptic inputs. LAT9993 SLoop A9 had little effect on dorsal root-evoked excitatory posts-synaptic potentials (EPSPs) or IPSPs (see FIG. 29).

TABLE 9

Summary data of changes in membrane potential and input resistance associated with LAT9993 SLoop A9-induced responses in dorsal horn neurons from Chung models of neuropathic pain.

|  | Rest | LAT9993 SLoop A9 1 μM | ΔVm |
|---|---|---|---|
|  | Membrane Potential (mV) | | |
| Mean | −58.4 | −45.6 | −12.9 |
| SEM | 6.5 | 11.2 | 7.3 |
| n | 3 | 3 | 3 |
| P |  | 0.221 |  |
|  | Normalised Membrane Potential | | |
| Mean | 100 | 76.9 | 23.1 |
| SEM |  | 13.1 | 13.1 |
| n | 3 | 3 | 3 |
| P |  | 0.220 |  |
|  | Control | LAT9993 SLoop A9 1 μM | ΔIR |
|  | Input Resistance (MΩ) | | |
| Mean | 220.6 | 243.1 | −22.5 |
| SEM | 101.6 | 54.4 | 49.6 |
| n | 3 | 3 | 3 |
| P |  | 0.694 |  |
|  | Normalised Input Resistance | | |
| Mean | 100 | 134.0 | −34.0 |
| SEM |  | 26.0 | 26.0 |
| n | 3 | 3 | 3 |
| P |  | 0.321 |  |

The Effects of LAT9993 SLoop A10 on Dorsal Horn Neurons

The effects of LAT9993 SLoop A10 (1 μM) were investigated on 3 dorsal horn neurons in spinal cord slices prepared from Chung models of neuropathic pain, recorded ipsilateral to the site of injury. In these neurons, LAT9993 Loop A10 induced a membrane hyperpolarisation and inhibition of activity in 2 neurons and induced membrane depolarisation in 1 neurone.

Figure 31:
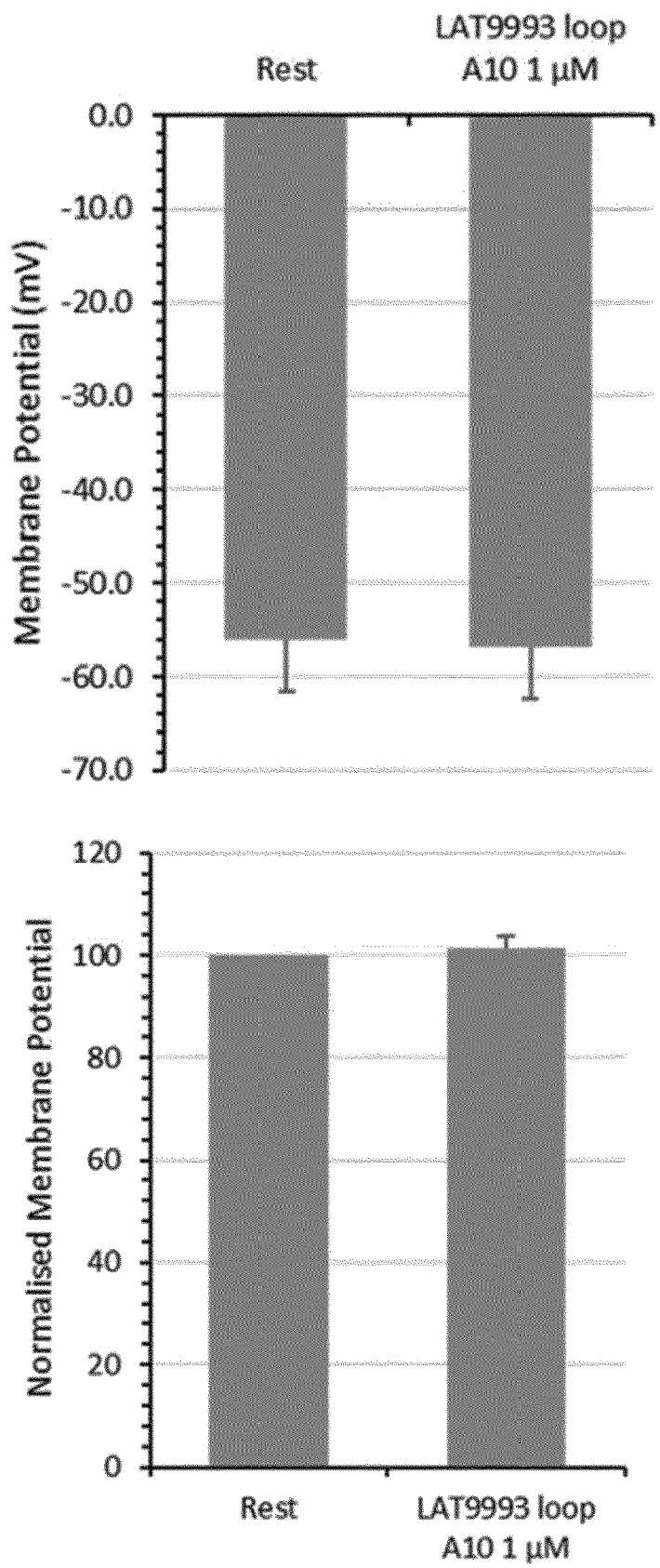
Figure 31:
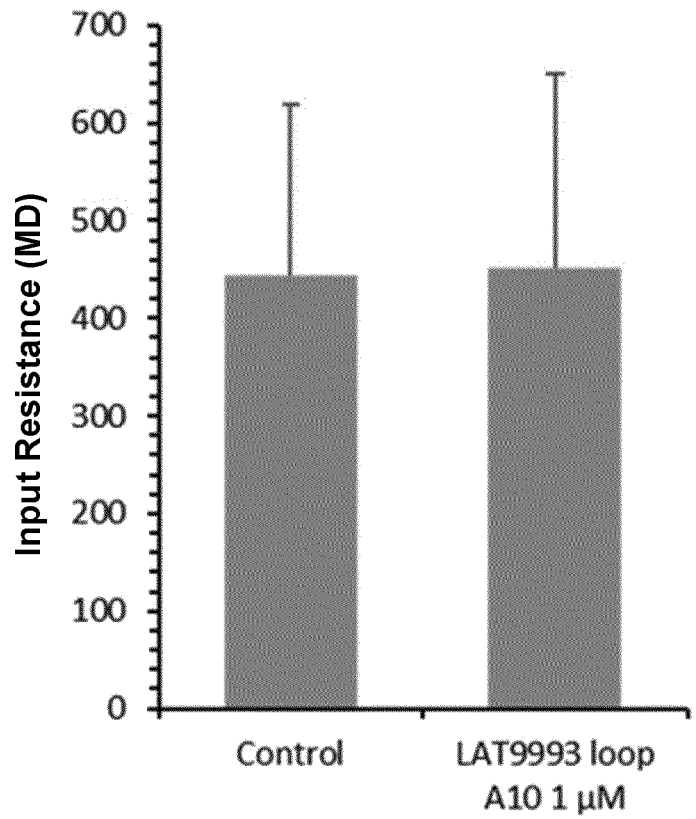
Figure 31:
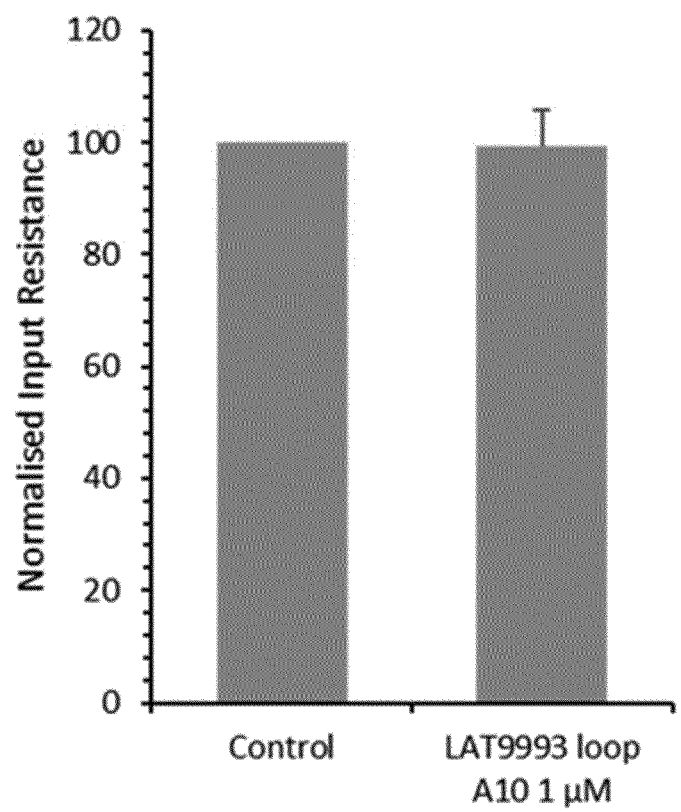

Data for all cells (n=3) showed LAT9993 SLoop A10 induced membrane hyperpolarisation from a mean resting membrane potential of −56.1±5.5 mV to a new steady-state resting potential of −56.8±5.6 mV, amounting to a 0.7±1.2 mV change in membrane potential (n=3, P=0.647, Table 10). LAT9993 SLoop A10-induced responses were associated overall with an increase in neuronal input resistance, indicated by the increase in amplitude of electrotonic potentials evoked in response to constant amplitude rectangular-wave current pulses (0.1 Hz; 10-600 pA; 0.5 to 1 s duration) and from the increase in slope of plots of VI relations. Neuronal input resistance was increased from a mean control resting level of 443.8±175.3 MΩ to 452.3±197.1 MΩ (n=3, P=0.780) in the presence of LAT9993 Loop A10, amounting to an 8.5±26.5 MΩ increase in neuronal input resistance. FIG. 31 summarises the effects of LAT9993 Loop A10 on membrane properties of dorsal horn neurons (see also Table 10). Overall LAT9993 Loop A10 had little effect on dorsal horn neurons.

Figure 32:
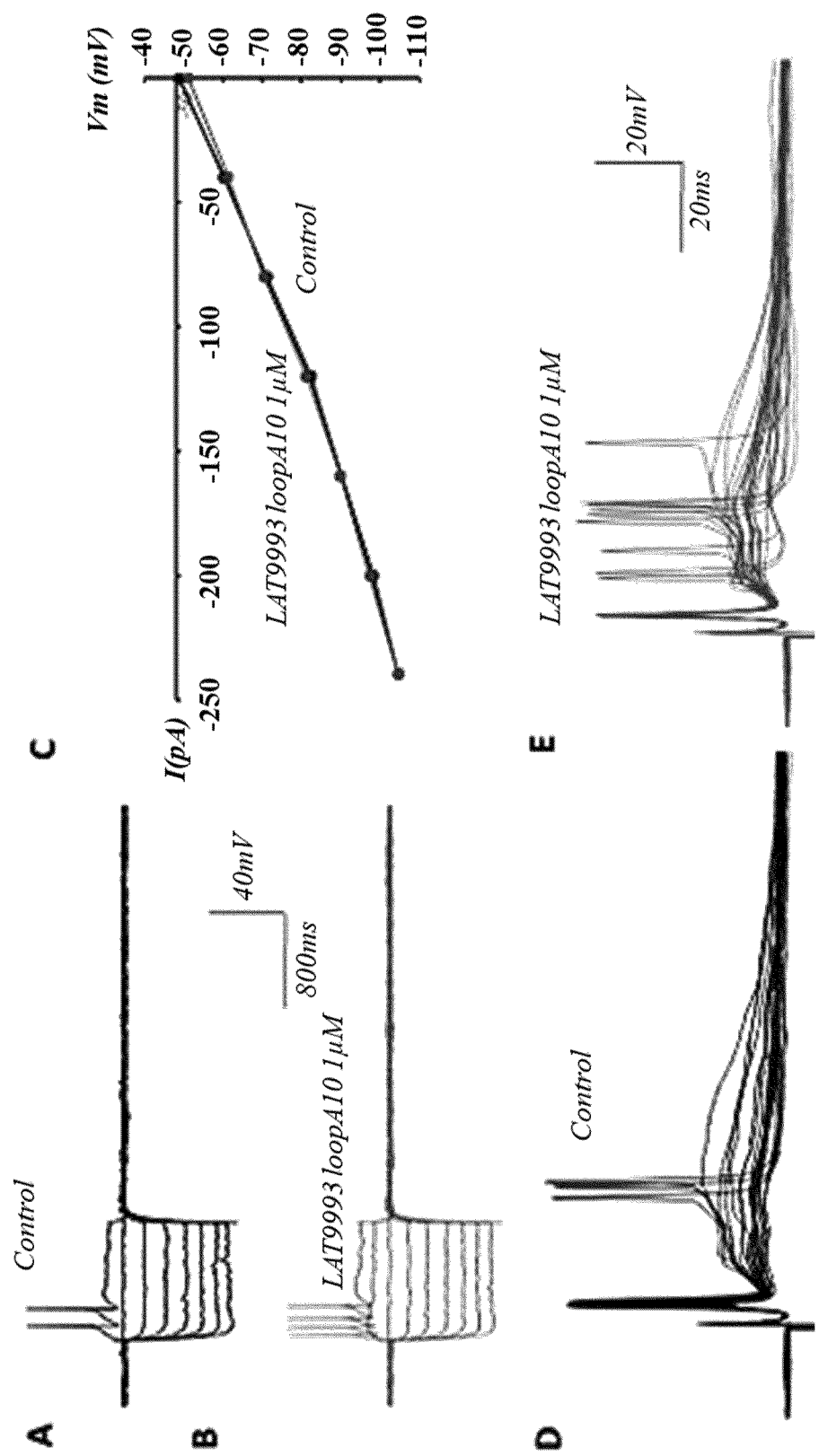

Wherever possible, the effects of LAT9993 SLoop A10 were tested on dorsal root afferent-mediated synaptic inputs. LAT9993 SLoop A10 had little effect on dorsal root-evoked excitatory posts-synaptic potentials (EPSPs; FIG. 32).

TABLE 10

Summary data of changes in membrane potential and input resistance associated with LAT9993 SLoop A10-induced responses in dorsal horn neurons from Chung models of neuropathic pain.

|  | Rest | LAT9993 SLoop A10 1 µM | ΔVm |
|---|---|---|---|
| | | Membrane Potential (mV) | |
| Mean | −56.1 | −56.8 | 0.7 |
| SEM | 5.5 | 5.6 | 1.2 |
| n | 3 | 3 | 3 |
| P | | 0.647 | |
| | | Normalised Membrane Potential | |
| Mean | 100 | 101.2 | −1.2 |
| SEM | | 2.4 | 2.4 |
| n | 3 | 3 | 3 |
| P | | 0.664 | |
| | Control | LAT9993 SLoop A10 1 µM | ΔIR |
| | | Input Resistance (MΩ) | |
| Mean | 443.8 | 452.3 | −8.5 |
| SEM | 175.3 | 197.1 | 26.5 |
| n | 3 | 3 | 3 |
| P | | 0.780 | |
| | | Normalised Input Resistance | |
| Mean | 100 | 99.3 | 0.7 |
| SEM | | 6.4 | 6.4 |
| n | 3 | 3 | 3 |
| P | | 0.923 | |

Discussion

This study investigated the effects of seven variants—LAT9993 LoopS (SEQ ID NO:28), SEQ11+LAT9993 Loop (SEQ ID NO:32; IDPSSEAPGHSCRSRPVESSC), SEQ25+LAT9993 Loop (SEQ ID NO:33; CRSRPVESSCSSKFSWDEYEQYKKE), LAT9993 SLoop A4 (SEQ ID NO:30), LAT9993 SLoop A7 (SEQ ID NO:31), LAT9993 SLoop A9 (SEQ ID NO:34; SCRSRPVEASC) and LAT9993 SLoop A10 (SEQ ID NO:35; SCRSRPVESAC) using an in vitro spinal cord slice with intact dorsal root afferents combined with single-cell whole-cell patch clamp electrophysiological recording technique.

The effects of each of these compounds were tested at a concentration of 1 µM on dorsal horn neurons in spinal cord slices prepared from Chung models of neuropathic pain.

LAT9993 LoopS overall induced a small excitation of dorsal horn associated with a similar small increase in neuronal input resistance. This compound had little effect on dorsal root afferent-mediated excitatory postsynaptic inputs. However, in one neurone LAT9993 Loops induced membrane depolarisation associated with inhibition of inward rectification. This latter observation has similarities to the effects previously seen for LAT9993 (Examples 1 and 2, above).

SEQ11+LAT9993 Loop overall induced membrane hyperpolarisation associated with a reduction in neuronal input resistance, in some cells via activation of a chloride conductance. No obvious effect was observed on dorsal root afferent-mediated synaptic inputs.

SEQ25+LAT9993 Loop overall induced a slight depolarisation of the membrane potential associated with no obvious change in neuronal input resistance, thus the mechanism of action is unclear. However, this compound suppressed spontaneous action potential firing in one neurone, suppressed dorsal root afferent-mediated synaptic inputs and an Afterdepolarising potential in one neurone. These observations have similarities to the effects observed with LAT9993, as described above.

LAT9993 Loop A4 overall induced membrane hyperpolarisation and suppression of activity. The response was associated with a reduction in neuronal input resistance, consistent with opening of ion channels and enhanced inward rectification. This compound also suppressed dorsal root-evoked excitatory synaptic transmission. Taken together, LAT9993 Loop A4 has similar effects to those reported for LAT9993, as described above.

LAT9993 Loop A7 overall induced membrane depolarisation associated with a reduction in neuronal input resistance. These effects are unlike those reported for LAT9993. However, LAT9993 Loop A7 did induce membrane depolarisation associated with a suppression of inward rectification in dorsal horn neurons and suppressed dorsal root afferent-mediated excitatory synaptic inputs. Thus, these latter effects have similarities and may be related to the effects observed for LAT9993 above.

LAT9993 Loop A9, overall was associated with a membrane depolarisation with no clear change in neuronal input resistance or ionic mechanism. This may reflect activity at electrogenic ion pumps/exchangers. Similarly, this compound had no obvious effect on dorsal root afferent-mediated synaptic inputs. Thus, there were few similarities between the effects of this compound and of LAT9993, as described above.

LAT9993 Loop A10 overall had little effect on membrane potential, neuronal input resistance or dorsal root afferent-mediated synaptic inputs. Thus, there was no apparent relationship between the effect of this compound and of LAT9993.

The invention claimed is:

1. A peptide of formula (I), or a pharmaceutically acceptable salt thereof:

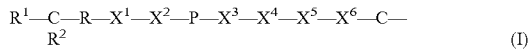
$$R^1-C-R-X^1-X^2-P-X^3-X^4-X^5-X^6-C-R^2 \quad (I)$$

wherein $X^1$, $X^3$, $X^5$, and $X^6$ each is an amino acid residue selected from the group consisting of serine, alanine, valine, leucine, isoleucine and glycine;

$X^2$ is alanine, arginine or lysine;

$X^4$ is glutamic acid or aspartic acid;

$R^1$ is selected from the group consisting of S, HS, GHS, PGHS (SEQ ID NO:4), APGHS (SEQ ID NO:5), EAPGHS (SEQ ID NO:6), SEAPGHS (SEQ ID NO:7), SSEAPGHS (SEQ ID NO:8), PSSEAPGHS (SEQ ID NO:9), and DPSSEAPGHS (SEQ ID NO:10), or $R^1$ is absent; and $R^2$ is selected from the group consisting of S, SS, SSK, SSKF (SEQ ID NO:14), SSKFS (SEQ ID NO:15), SSKFSW (SEQ ID NO:16), SSKFSWD SEQ ID NO:17), SSKFSWDE (SEQ ID NO:18), SSKFSWDEY (SEQ ID NO:19), and SSKFSWDEYE (SEQ ID NO:20), or $R^2$ is absent; and wherein the peptide of formula (I), or the pharmaceutically acceptable salt thereof, is a cyclic peptide formed by a disulphide bond between the two cysteine residues and has a length of no more than 20 amino acid residues.

2. The peptide of claim 1, comprising an amino acid sequence selected from the group consisting of SEQ ID NOs:26-29.

3. The peptide of claim 2, having the amino acid sequence of SEQ ID NO:26.

4. The peptide of claim 2, having the amino acid sequence of SEQ ID NO:27.

5. The peptide of claim 2, having the amino acid sequence of SEQ ID NO:28.

6. The peptide of claim 2, having the amino acid sequence of SEQ ID NO:29.

7. The peptide of claim 1, wherein $X^5$ and $X^6$ each is an amino acid residue selected from the group consisting of serine, valine, leucine, isoleucine and glycine.

8. A pharmaceutical composition comprising the peptide of claim 1, or a pharmaceutically acceptable salt thereof, and at least one pharmaceutically acceptable carrier.

* * * * *

SEQUENCE LISTING

```
<160> NUMBER OF SEQ ID NOS: 35

<210> SEQ ID NO 1
<211> LENGTH: 12
<212> TYPE: PRT
<213> ORGANISM: Homo sapiens
<220> FEATURE:
<221> NAME/KEY: VARIANT
<222> LOCATION: (1)..(1)
<223> OTHER INFORMATION: selected from the group consisting of serine
      and SEQ ID NOs:2-11
```

```
<220> FEATURE:
<221> NAME/KEY: VARIANT
<222> LOCATION: (4)..(4)
<223> OTHER INFORMATION: serine, alanine, valine, leucine, isoleucine or
      glycine
<220> FEATURE:
<221> NAME/KEY: VARIANT
<222> LOCATION: (5)..(5)
<223> OTHER INFORMATION: alanine, arginine or lysine
<220> FEATURE:
<221> NAME/KEY: VARIANT
<222> LOCATION: (7)..(7)
<223> OTHER INFORMATION: serine, alanine, valine, leucine, isoleucine or
      glycine
<220> FEATURE:
<221> NAME/KEY: VARIANT
<222> LOCATION: (8)..(8)
<223> OTHER INFORMATION: glutamic acid or aspartic acid
<220> FEATURE:
<221> NAME/KEY: VARIANT
<222> LOCATION: (9)..(9)
<223> OTHER INFORMATION: serine, alanine, valine, leucine, isoleucine or
      glycine
<220> FEATURE:
<221> NAME/KEY: VARIANT
<222> LOCATION: (10)..(10)
<223> OTHER INFORMATION: serine, alanine, valine, leucine, isoleucine or
      glycine
<220> FEATURE:
<221> NAME/KEY: VARIANT
<222> LOCATION: (12)..(12)
<223> OTHER INFORMATION: selected from the group consisting on serine
      and SEQ ID NOs:12-25

<400> SEQUENCE: 1

Xaa Cys Arg Xaa Xaa Pro Xaa Xaa Xaa Xaa Cys Xaa
1               5                   10

<210> SEQ ID NO 2
<211> LENGTH: 2
<212> TYPE: PRT
<213> ORGANISM: Homo sapiens

<400> SEQUENCE: 2

His Ser
1

<210> SEQ ID NO 3
<211> LENGTH: 3
<212> TYPE: PRT
<213> ORGANISM: Homo sapiens

<400> SEQUENCE: 3

Gly His Ser
1

<210> SEQ ID NO 4
<211> LENGTH: 4
<212> TYPE: PRT
<213> ORGANISM: Homo sapiens

<400> SEQUENCE: 4

Pro Gly His Ser
1

<210> SEQ ID NO 5
<211> LENGTH: 5
<212> TYPE: PRT
<213> ORGANISM: Homo sapiens

<400> SEQUENCE: 5
```

Ala Pro Gly His Ser
1               5

<210> SEQ ID NO 6
<211> LENGTH: 6
<212> TYPE: PRT
<213> ORGANISM: Homo sapiens

<400> SEQUENCE: 6

Glu Ala Pro Gly His Ser
1               5

<210> SEQ ID NO 7
<211> LENGTH: 7
<212> TYPE: PRT
<213> ORGANISM: Homo sapiens

<400> SEQUENCE: 7

Ser Glu Ala Pro Gly His Ser
1               5

<210> SEQ ID NO 8
<211> LENGTH: 8
<212> TYPE: PRT
<213> ORGANISM: Homo sapiens

<400> SEQUENCE: 8

Ser Ser Glu Ala Pro Gly His Ser
1               5

<210> SEQ ID NO 9
<211> LENGTH: 9
<212> TYPE: PRT
<213> ORGANISM: Homo sapiens

<400> SEQUENCE: 9

Pro Ser Ser Glu Ala Pro Gly His Ser
1               5

<210> SEQ ID NO 10
<211> LENGTH: 10
<212> TYPE: PRT
<213> ORGANISM: Homo sapiens

<400> SEQUENCE: 10

Asp Pro Ser Ser Glu Ala Pro Gly His Ser
1               5                   10

<210> SEQ ID NO 11
<211> LENGTH: 11
<212> TYPE: PRT
<213> ORGANISM: Homo sapiens

<400> SEQUENCE: 11

Ile Asp Pro Ser Ser Glu Ala Pro Gly His Ser
1               5                   10

<210> SEQ ID NO 12
<211> LENGTH: 2
<212> TYPE: PRT
<213> ORGANISM: Homo sapiens

<400> SEQUENCE: 12

Ser Ser

<210> SEQ ID NO 13
<211> LENGTH: 3
<212> TYPE: PRT
<213> ORGANISM: Homo sapiens

<400> SEQUENCE: 13

Ser Ser Lys
1

<210> SEQ ID NO 14
<211> LENGTH: 4
<212> TYPE: PRT
<213> ORGANISM: Homo sapiens

<400> SEQUENCE: 14

Ser Ser Lys Phe
1

<210> SEQ ID NO 15
<211> LENGTH: 5
<212> TYPE: PRT
<213> ORGANISM: Homo sapiens

<400> SEQUENCE: 15

Ser Ser Lys Phe Ser
1               5

<210> SEQ ID NO 16
<211> LENGTH: 6
<212> TYPE: PRT
<213> ORGANISM: Homo sapiens

<400> SEQUENCE: 16

Ser Ser Lys Phe Ser Trp
1               5

<210> SEQ ID NO 17
<211> LENGTH: 7
<212> TYPE: PRT
<213> ORGANISM: Homo sapiens

<400> SEQUENCE: 17

Ser Ser Lys Phe Ser Trp Asp
1               5

<210> SEQ ID NO 18
<211> LENGTH: 8
<212> TYPE: PRT
<213> ORGANISM: Homo sapiens

<400> SEQUENCE: 18

Ser Ser Lys Phe Ser Trp Asp Glu
1               5

<210> SEQ ID NO 19
<211> LENGTH: 9
<212> TYPE: PRT
<213> ORGANISM: Homo sapiens

<400> SEQUENCE: 19

Ser Ser Lys Phe Ser Trp Asp Glu Tyr
1               5

<210> SEQ ID NO 20
<211> LENGTH: 10
<212> TYPE: PRT
<213> ORGANISM: Homo sapiens

<400> SEQUENCE: 20

Ser Ser Lys Phe Ser Trp Asp Glu Tyr Glu
1               5                   10

<210> SEQ ID NO 21
<211> LENGTH: 11
<212> TYPE: PRT
<213> ORGANISM: Homo sapiens

<400> SEQUENCE: 21

Ser Ser Lys Phe Ser Trp Asp Glu Tyr Glu Gln
1               5                   10

<210> SEQ ID NO 22
<211> LENGTH: 12
<212> TYPE: PRT
<213> ORGANISM: Homo sapiens

<400> SEQUENCE: 22

Ser Ser Lys Phe Ser Trp Asp Glu Tyr Glu Gln Tyr
1               5                   10

<210> SEQ ID NO 23
<211> LENGTH: 13
<212> TYPE: PRT
<213> ORGANISM: Homo sapiens

<400> SEQUENCE: 23

Ser Ser Lys Phe Ser Trp Asp Glu Tyr Glu Gln Tyr Lys
1               5                   10

<210> SEQ ID NO 24
<211> LENGTH: 14
<212> TYPE: PRT
<213> ORGANISM: Homo sapiens

<400> SEQUENCE: 24

Ser Ser Lys Phe Ser Trp Asp Glu Tyr Glu Gln Tyr Lys Lys
1               5                   10

<210> SEQ ID NO 25
<211> LENGTH: 15
<212> TYPE: PRT
<213> ORGANISM: Homo sapiens

<400> SEQUENCE: 25

Ser Ser Lys Phe Ser Trp Asp Glu Tyr Glu Gln Tyr Lys Lys Glu
1               5                   10                  15

<210> SEQ ID NO 26
<211> LENGTH: 11
<212> TYPE: PRT
<213> ORGANISM: Homo sapiens

<400> SEQUENCE: 26

Ser Cys Arg Ser Arg Pro Val Glu Ser Ser Cys
1               5                   10

<210> SEQ ID NO 27

```
<211> LENGTH: 10
<212> TYPE: PRT
<213> ORGANISM: Homo sapiens

<400> SEQUENCE: 27

Cys Arg Ser Arg Pro Val Glu Ser Ser Cys
1               5                   10

<210> SEQ ID NO 28
<211> LENGTH: 11
<212> TYPE: PRT
<213> ORGANISM: Homo sapiens

<400> SEQUENCE: 28

Cys Arg Ser Arg Pro Val Glu Ser Ser Cys Ser
1               5                   10

<210> SEQ ID NO 29
<211> LENGTH: 12
<212> TYPE: PRT
<213> ORGANISM: Homo sapiens

<400> SEQUENCE: 29

Ser Cys Arg Ser Arg Pro Val Glu Ser Ser Cys Ser
1               5                   10

<210> SEQ ID NO 30
<211> LENGTH: 11
<212> TYPE: PRT
<213> ORGANISM: Homo sapiens

<400> SEQUENCE: 30

Ser Cys Arg Ala Arg Pro Val Glu Ser Ser Cys
1               5                   10

<210> SEQ ID NO 31
<211> LENGTH: 11
<212> TYPE: PRT
<213> ORGANISM: Homo sapiens

<400> SEQUENCE: 31

Ser Cys Arg Ser Arg Pro Ala Glu Ser Ser Cys
1               5                   10

<210> SEQ ID NO 32
<211> LENGTH: 21
<212> TYPE: PRT
<213> ORGANISM: Homo sapiens

<400> SEQUENCE: 32

Ile Asp Pro Ser Ser Glu Ala Pro Gly His Ser Cys Arg Ser Arg Pro
1               5                   10                  15

Val Glu Ser Ser Cys
            20

<210> SEQ ID NO 33
<211> LENGTH: 25
<212> TYPE: PRT
<213> ORGANISM: Homo sapiens

<400> SEQUENCE: 33

Cys Arg Ser Arg Pro Val Glu Ser Ser Cys Ser Ser Lys Phe Ser Trp
1               5                   10                  15

Asp Glu Tyr Glu Gln Tyr Lys Lys Glu
```

```
<210> SEQ ID NO 34
<211> LENGTH: 11
<212> TYPE: PRT
<213> ORGANISM: Homo sapiens

<400> SEQUENCE: 34

Ser Cys Arg Ser Arg Pro Val Glu Ala Ser Cys
1               5                   10

<210> SEQ ID NO 35
<211> LENGTH: 11
<212> TYPE: PRT
<213> ORGANISM: Homo sapiens

<400> SEQUENCE: 35

Ser Cys Arg Ser Arg Pro Val Glu Ser Ala Cys
1               5                   10
```